United States Patent
Thurston et al.

(10) Patent No.: US 10,399,970 B2
(45) Date of Patent: Sep. 3, 2019

(54) PYRRIDINOBENZODIAZEPINE AND BENZOPYRRIDODIAZECINE COMPOUNDS

(71) Applicant: FEMTOGENIX LIMITED, Welwyn Garden City (GB)

(72) Inventors: David Edwin Thurston, Welwyn Garden City (GB); Khondaker Mirazur Rahman, Welwyn Garden City (GB); Paul Joseph Mark Jackson, Welwyn Garden City (GB)

(73) Assignee: Femtogenix Limited (GB)

( * ) Notice: Subject to any disclaimer, the term of this patent is extended or adjusted under 35 U.S.C. 154(b) by 0 days.

(21) Appl. No.: 15/579,148

(22) PCT Filed: Jun. 9, 2016

(86) PCT No.: PCT/GB2016/051701
§ 371 (c)(1),
(2) Date: Dec. 1, 2017

(87) PCT Pub. No.: WO2016/198869
PCT Pub. Date: Dec. 15, 2016

(65) Prior Publication Data
US 2018/0162855 A1    Jun. 14, 2018

(30) Foreign Application Priority Data
Jun. 9, 2015    (GB) .................................. 1510010.0

(51) Int. Cl.
C07D 471/04    (2006.01)
C07D 519/00    (2006.01)

(52) U.S. Cl.
CPC .......... C07D 471/04 (2013.01); C07D 519/00 (2013.01)

(58) Field of Classification Search
CPC ........................... C07D 471/04; C07D 519/00; A61K 31/5513; A61P 35/00; A61P 37/00
(Continued)

(56) References Cited

U.S. PATENT DOCUMENTS

| | | |
|---|---|---|
| 5,366,972 A | 11/1994 | Hargrave et al. |
| 5,418,229 A | 5/1995 | Alker et al. |

(Continued)

FOREIGN PATENT DOCUMENTS

| | | |
|---|---|---|
| EP | 0556947 | 8/1993 |
| EP | 1608650 | 6/2010 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*

(Continued)

Primary Examiner — Deepak R Rao
(74) Attorney, Agent, or Firm — Thomas G. Peterson; Maynard Cooper & Gale

(57) ABSTRACT

The invention relates to pyrridinobenzodiazepines (PDDs) comprising three fused 6-7- 6-membered rings and to benzopyrridodiazecines (BPDs) comprising three fused 6-8- 6-membered rings and, in particular, to PDD or BPD dimers linked together or PDD and BPD monomers linked to aromatic groups, and pharmaceutically acceptable salts thereof, which are useful as medicaments, such as anti-proliferative agents. PDDs and BPDs may be represented by formula (I): and salts or solvates thereof, wherein $R_2$, $R_4$-$R_6$ and $R_8$ are independently selected substituent groups; and either: (i) $R_9$ and $R_{10}$ together form a double bond; (ii) $R_9$ is H and $R_{10}$ is OH; or (iii) $R_9$ is H and $R_{10}$ is $OR^A$ and $R^A$ is $C_{1-6}$ alkyl; wherein each of m, n, u and w may be 0 or 1; where (a) the compound is a dimer with each monomer being the same or different and being of formula (I) where one of $R_1$, $R_2$, $R_3$ and $R_7$ of the first monomer and one of $R'_1$, $R'_2$, $R_3$ and $R'_7$ of the second monomer form together a bridge having the formula —X-L-X'— linking the monomers and m+n+u+w=1; or (b) a dimer and one of $R_1$, $R_2$ and $R_3$ of the first monomer and one of $R'_1$, $R'_2$ and $R_3$ of the second monomer form together a bridge having the formula —X-L-X'— linking the monomers and m=n=u=w=o; or (c) one of $R_1$, $R_2$, $R_3$ and $R_7$ has the formula: —X-L-X'-D or —(CH$_2$)f-O—$R_{14}$ and m+n+u+w=o or 1; or (d) $R_7$ has the formula: —X-L-X'— D or —(CH$_2$)$_g$—O—$_{15}$ and m+n+u+ w=1; and X-L-X'— is a linker group and D has the formula (II) or (III).

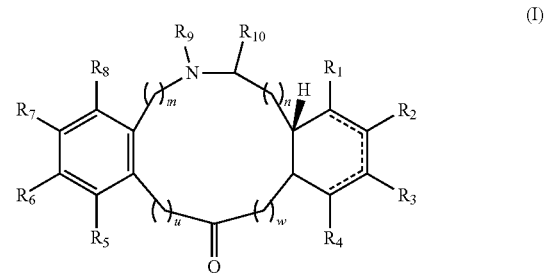

(I)

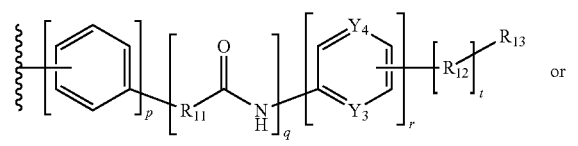

(II) or

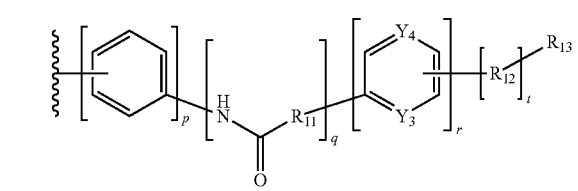

(III)

19 Claims, 3 Drawing Sheets

(58) Field of Classification Search
USPC .................. 540/460, 496; 514/183, 211.04
See application file for complete search history.

(56) References Cited

U.S. PATENT DOCUMENTS

| | | |
|---|---|---|
| 5,650,409 A | 7/1997 | Rogers et al. |
| 5,712,269 A | 1/1998 | McCabe et al. |
| 6,608,193 B2 | 8/2003 | Liu et al. |
| 6,864,250 B1 | 3/2005 | Funamizu et al. |
| 7,067,511 B2 | 6/2006 | Thurston et al. |
| 7,384,934 B2 | 6/2008 | Aicher et al. |
| 7,456,169 B2 | 11/2008 | Hasvold et al. |
| 7,528,128 B2 | 5/2009 | Ahmed et al. |
| 7,709,470 B2 | 5/2010 | Sakaki et al. |
| 8,039,464 B2 | 10/2011 | Schrattenholz |
| 8,426,402 B2 | 4/2013 | Li et al. |
| 8,569,298 B2 | 10/2013 | Barlaam et al. |
| 8,592,576 B2 | 11/2013 | Howard et al. |
| 8,637,664 B2 | 1/2014 | Howard et al. |
| 8,637,665 B2 | 1/2014 | Ahmed et al. |
| 8,642,610 B2 | 2/2014 | Brown |
| 9,006,233 B2 | 4/2015 | Cook et al. |
| 9,315,497 B2 | 4/2016 | Verdecia Reyes et al. |
| 9,376,440 B2 | 6/2016 | Howard et al. |
| 9,518,118 B2 | 12/2016 | Chen et al. |
| 9,526,801 B2 | 12/2016 | McDonald et al. |
| 9,534,000 B2 | 1/2017 | Chari |
| 9,951,133 B2 | 4/2018 | Yu et al. |
| 9,974,864 B2 | 5/2018 | Junutula et al. |
| 2007/0191349 A1 | 8/2007 | Howard et al. |
| 2008/0275023 A1 | 11/2008 | Guidi et al. |
| 2009/0318412 A1 | 12/2009 | Matsumoto et al. |
| 2011/0263574 A1 | 10/2011 | Schrattenholz |
| 2012/0115852 A1 | 5/2012 | Schultz et al. |
| 2013/0210804 A1 | 8/2013 | Anthony et al. |
| 2016/0207949 A1 | 7/2016 | Zhao |
| 2017/0253602 A1 | 9/2017 | Schall et al. |
| 2017/0333442 A1 | 11/2017 | Yin et al. |
| 2017/0362220 A1 | 12/2017 | Fischer et al. |
| 2017/0369453 A1 | 12/2017 | Thomas et al. |
| 2017/0369507 A1 | 12/2017 | Christian et al. |
| 2018/0110873 A1 | 4/2018 | McDonald et al. |

FOREIGN PATENT DOCUMENTS

| | | |
|---|---|---|
| EP | 2421870 | 3/2016 |
| JP | 2009263283 | 11/2009 |
| WO | 199638422 | 12/1996 |
| WO | 2007039752 A1 | 4/2007 |
| WO | WO2010091150 A1 | 8/2010 |
| WO | WO2015028850 A1 | 3/2015 |
| WO | WO2015166289 A1 | 11/2015 |
| WO | 2017032983 A1 | 3/2017 |
| WO | 2017074914 | 5/2017 |
| WO | 2018053552 | 3/2018 |

OTHER PUBLICATIONS

Gura, Systems for identifying new drugs are often faulty, Science, Nov. 7, 1997, 278(5340): 1041-2.*

Johnson et al., Relationships between drug activity in NCI preclinical in vitro and in vivo models and early clinical trials, Br J Cancer. May 18, 2001, 84(10): 1424-31.*

Simone, Introduction, Omenn, Cancer Prevention, Part XIV. Oncology, Cecil Textbook of Medicine, 20th Edition, vol. 1, pp. 1004-1010 (1996).*

Jordan, V.C., Tamoxifen: A most unlikely pioneering medicine, Nature Reviews: Drug Discovery, vol. 2, 2003, pp. 205-213.*

Cole, Natalie, British Search Report (GB1510010.0), dated Feb. 26, 2016.

Pfau, Andrea, Written Opinion of the Int'l Searching Authority (PCT/GB2016/051701), dated Aug. 10, 2016.

Markandeya N et al: "Asymmetric syntheses of piperidinobenzodiazepines through 'cation-pool' host/guest supramolecular approach and their DNA-binding studies",Tetrahedron Asymmetry, vol. 21, No. 21-22, Nov. 25, 2010 (Nov. 25, 2010), pp. 2625-2630.

Tozuka Z et al: "Studies on tomaymycin. III. Syntheses and antitumor activity of tomaymycin analogs",The Journal of Antibiotics, vol. 36, No. 12, Dec. 1, 1983 (Dec. 1, 1983 ), pp. 1699-1708.

Jordan, V. Craig, "Tamoxifen: A Most Unlikely Pioneering Medicine," Nature Reviews: Drug Discovery, vol. 2, Mar. 2003,pp. 205-213.

Vippagunta, Sudha R., et al, "Crystalline Solids," Advanced Drug Delivery Reviews, vol. 48, 2001, pp. 3-26.

Hackam, Daniel G., et al., "Translation of Research Evidence from Animals to Humans," JAMA, vol. 296, No. 14, pp. 1731-1732.

Evans, S. David, "Great Britain Search Report—GB Application No. GB1514928.9" dated Feb. 5, 2016, pp. 1-4.

Sulberg, Anna, Int'l Search Report and Written Opinion (PCT/GB2016/052565), dated Nov. 4, 2016, pp. 1-14.

Baraldi, Pier Giovanni,et al., "Synthesis, in vitro antiproliferative Activity, and DNA-Binding Properties of Hybrid Molecules Containing Pyrrolo[2,1-c][1,4] benzodiazepine and Minor-Groove-Binding Oligopyrrole Carriers," J. Med. Cehm., vol. 42, 1999, pp. 5131-5141.

* cited by examiner

PYRRIDINOBENZODIAZEPINE AND BENZOPYRRIDODIAZECINE COMPOUNDS

CROSS-REFERENCE TO RELATED APPLICATIONS

This application is a national stage under 35 U.S.C. 371 of International Application PCT/GB2016/051701, filed on Jun. 9, 2016 (currently published). International Application PCT/GB2016/051701 cites the priority of British Patent Application No. 1510010.0, filed Jun. 9, 2015 (abandoned).

FIELD OF THE INVENTION

The invention relates to pyrridinobenzodiazepines (PDDs) comprising three fused 6-7- 6-membered rings and to benzopyrridodiazecines (BPDs) comprising three fused 6-8- 6-membered rings. In particular it relates to PDD dimers and BPD dimers linked together, and PDD and BPD monomers linked to aromatic groups, and to pharmaceutically acceptable salts thereof, which are useful as medicaments, in particular as anti-proliferative agents.

BACKGROUND TO THE INVENTION

Pyrridinobenzodiazepines (PDDs) and benzopyrridodiazecines (BPDs) are related structures to pyrrolobenzodiazepines (PBDs). The pyrrolobenzodiazepines (PBDs) are a group of compounds some of which have been shown to be sequence-selective DNA minor-groove binding agents. The PBDs were originally discovered in *Streptomyces* species (1-5). They are tricyclic in nature, and are comprised of fused 6-7-5-membered rings that comprise an anthranilate (A ring), a diazepine (B ring) and a pyrrolidine (C ring) (3). They are characterized by an electrophilic N10=C11 imine group (as shown below) or the hydrated equivalent, a carbinolamine [NH—CH(OH)], or a carbinolamine alkyl ether ([NH—CH(OR, where R=alkyl)] which can form a covalent bond to a C2-amino group of guanine in DNA to form a DNA adduct (6).

attack by the exocyclic C2-amino group of the central guanine occurs to form the covalent adduct (7). Once bound, the PBD remains anchored in the DNA minor groove, avoiding DNA repair by causing negligible distortion of the DNA helix (16). The ability of PBDs to form an adduct in the minor groove and crosslink DNA enables them to interfere with DNA processing and, hence, their potential for use as antiproliferative agents.

A number of monomeric PBD structures have been isolated from *Streptomyces* species, including anthramycin (18) the first PBD, tomamycin (19), and more recently usabamycin (20) from a marine sediment *Streptomyces* species in a marine sediment. This has led to the development of a large range of synthetic analogues which have been reviewed (1, 21). More recently, a number of monomeric PBD structures that are linked through their C8 position to pyrroles and imidazoles have been reported WO 2007/039752, WO 2013/164593 (22-27).

In addition to monomeric PBD structures, a large range of synthetic PBD dimers (i.e. two PBD structures linked via a spacer) have been developed. Early C7- and C8-linked examples (28, 29) were designed to span greater lengths of DNA than the PBD monomers, to have enhanced sequence-selectivity, and to form DNA cross-links that might be more difficult for tumour cells to repair. In particular, the C8 position of the A ring has been extensively utilized for the production of PBD dimers (29, 30). The synthesis of various PBD dimers has been reviewed (1, 21).

WO 2010/091150 discloses dimeric PBD derivatives linked via their aromatic A-rings, in particular, dimers of tetracyclic 6-7-5-6 ring systems. WO 2010/028850 also discloses a dimer of a 6-7-6 ring system linked via their A-rings. WO 2015/028850 discloses PBD dimers that are linked via phosphine oxide containing linkers attached to their aromatic A-rings. In addition, WO 2015/028850 discloses a compound containing a 6-7-6 ring system linked via the key phosphine oxide containing linkers.

Various PBDs have been shown to act as cytotoxic agents in vitro, for example, WO 00/12508, WO 2004/087711, and

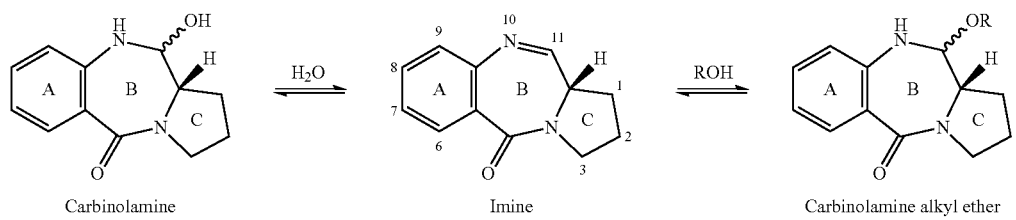

Carbinolamine        Imine        Carbinolamine alkyl ether

The natural products interact in the minor groove of the DNA helix with excellent fit (i.e., good "isohelicity") due to a right-handed longitudinal twist induced by a chiral C11a-position which has the (S)-configuration (6). The DNA adduct has been reported to inhibit a number of biological processes including the binding of transcription factors (7-9) and the function of enzymes such as endonucleases (10, 11) and RNA polymerase (12). PBD monomers (e.g., anthramycin) have been shown by footprinting (6), NMR (13, 14), molecular modeling (15) and X-ray crystallography (16) to span three base pairs and to have a thermodynamic preference for the sequence 5'-Pu-G-Pu-3' (where Pu=purine, and G is the reacting guanine) (17) and a kinetic preference for Py-5-Py (where Py=Pyrimidine).

PBDs are thought to interact with DNA by first locating at a low-energy binding sequence (i.e., a 5'-Pu-G-Pu-3' triplet) through Van der Waals, hydrogen bonding and electrostatic interactions (7). Then, once in place, a nucleophilic as anti-tumour in vivo in animal tumour models, for example, WO 2011/117882, WO 2013/164593. Furthermore, the C8/C8'-linked PBD dimer SJG-136 (29, 32) has completed Phase I clinical trials for leukaemia and ovarian cancer (31) and has shown sufficient therapeutic benefit to progress to Phase II studies.

SJG-136

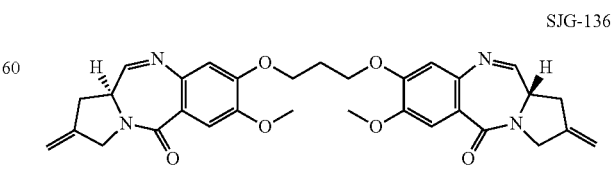

However, results from a Phase I clinical evaluation of SJG-136 revealed that the drug produced several adverse effects including lower-limb edema and fatigue (33).

Thus, there exists a need for further compounds related to PBDs that are therapeutically active for treating a variety of proliferative diseases.

The present application reports pyrridinobenzodiazepines (PDDs) linked by the C-ring. PDDs are related to PBDs but contain an expanded 6-membered C-ring as compared to the 5-membered C-ring of PBDs. The present application also reports benzopyrridodiazecines (BPDs), which have an expanded 8-membered B-ring in addition to the expended 6-membered C-ring. The present invention seeks to alleviate or overcome problem(s) associated with the prior art.

SUMMARY OF THE INVENTION

The present invention provides a compound of formula (I):

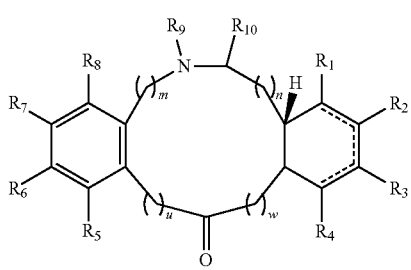

and salts or solvates thereof, wherein:

the dotted lines indicates the optional presence of a double bond between one or more of C1 and C2, C2 and C3, and C3 and C4;

$R_4$ is selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2R$, $CO_2H$, COR, CN;

$R_5$, $R_6$ and $R_8$ are independently selected from H, R, OH, OR, SH, SR, $NH_2$, NHR, NRR', $CO_2H$, $CH_2$—$CO_2H$, $CO_2R$, $CH_2$—$CO_2R$, $NO_2$, $Me_3Sn$ and halo;

each R and R' is independently selected from optionally substituted $C_{1-12}$ alkyl, $C_{3-20}$ heterocyclyl, $C_{3-20}$ heteroaryl, $C_{4-32}$ heteroaralkyl, $C_{5-20}$ aryl groups and $C_{6-32}$ aralkyl;

and either:
(i) $R_9$ and $R_{10}$ together form a double bond;
(ii) $R_9$ is H and $R_{10}$ is OH; or
(iii) $R_9$ is H and $R_{10}$ is $OR^A$ and $R^A$ is $C_{1-6}$ alkyl;
wherein each of m, n, u and w may be 0 or 1; and (a) the compound is a dimer with each monomer being the same or different and being of formula (I) where one of $R_1$, $R_2$, $R_3$ and $R_7$ of the first monomer and one of $R'_1$, $R'_2$, $R'_3$ and $R'_7$ of the second monomer form together a bridge having the formula —X-L-X'— linking the monomers and m+n+u+w=1;

and the remaining of $R_1$, $R_2$ and $R_3$ of the first monomer and the remaining of $R'_1$, $R'_2$ and $R'_3$ of the second monomer that do not form the bridge are independently selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2R$, $CO_2H$, COR, CN, ($C_{1-12}$ alkylene)-C(O)NR", R''' and ($C_{2-12}$ alkenylene)-C(O)NR'R" and halo;

and the remaining of $R_7$ of the first monomer and $R'_7$ of the second monomer that do not form the bridge are independently selected from H, R, OH, OR, $NH_2$, NHR, NRR', $CH_2$—OR, $CH_2$—$CO_2R$, $CH_2$—$CO_2H$, $CH_2$—$SO_2R$, O—$SO_2R$, $CO_2R$, $CO_2H$, COR, CN, ($C_{1-12}$ alkylene)-C(O)NR", R''' and ($C_{2-12}$ alkenylene)-C(O)NR'R" and halo;

or (b) the compound is a dimer with each monomer being the same or different and being of formula (I) where one of $R_1$, $R_2$ and $R_3$ of the first monomer and one of $R'_1$, $R'_2$, and $R'_3$ of the second monomer form together a bridge having the formula —X-L-X'— linking the monomers and m=n=u=w=0;

and the remaining of $R_1$, $R_2$ and $R_3$ of the first monomer and the remaining of $R'_1$, $R'_2$ and $R'_3$ of the second monomer that do not form the bridge are independently selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2R$, $CO_2H$, COR, CN, ($C_{1-12}$ alkylene)-C(O)NR", R''' and ($C_{2-12}$ alkenylene)-C(O)NR'R" and halo;

and that $R_7$ of the first monomer and $R'_7$ of the second monomer are independently selected from H, R, OH, OR, $NH_2$, NHR, NRR', $CH_2$—OR, $CH_2$—$CO_2R$, $CH_2$—$CO_2H$, $CH_2$—$SO_2R$, O—$SO_2R$, $CO_2R$, $CO_2H$, COR, CN, ($C_{1-12}$ alkylene)-C(O)NR", R''' and ($C_{2-12}$ alkenylene)-C(O)NR'R" and halo;

or (c) one of $R_1$, $R_2$ and $R_3$ has the formula:

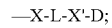
—X-L-X'-D;

or

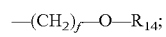
—$(CH_2)_f$—O—$R_{14}$;

wherein $R_{14}$ is selected from H and R; f is 0 or 1;
and m+n+u+w=0 or 1;
and the remaining of $R_1$, $R_2$ and $R_3$ are independently selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2R$, $CO_2H$, COR, CN, ($C_{1-12}$ alkylene)-C(O)NR", R''' and ($C_{2-12}$ alkenylene)-C(O)NR'R" and halo;

and $R_7$ is selected from H, R, OH, OR, $NH_2$, NHR, NRR', $CH_2$—OR, $CH_2$—$CO_2R$, $CH_2$—$CO_2H$, $CH_2$—$SO_2R$, O—$SO_2R$, $CO_2R$, $CO_2H$, COR, CN, ($C_{1-12}$ alkylene)-C(O)NR", R''' and ($C_{2-12}$ alkenylene)-C(O)NR'R" and halo;

or (d) $R_7$ has the formula:

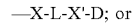
—X-L-X'-D; or

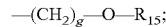
—$(CH_2)_g$—O—$R_{15}$;

wherein $R_{15}$ is selected from H and R; g is 0 or 1;
and m+n+u+w=1;
and $R_1$, $R_2$ and $R_3$ are independently selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2R$, $CO_2H$, COR, CN, ($C_{1-12}$ alkylene)-C(O)NR",R''' and ($C_{2-12}$ alkenylene)-C(O)NR'R" and halo;

wherein:

X is selected from O, S, NR", =CR"—, CR"R''', CR"R'''O, C(=O), C(=O)NR", NR"C(=O), O—C(O) and C(O)—O;

L is selected from an amino acid, a peptide chain having from 2 to 6 amino acids, an alkylene chain containing from 1 to 12 carbon atoms which may contain one or more carbon-carbon double or triple bonds, a paraformaldehyde chain —$(OCH_2)_{1-12}$—, a polyethylene glycol chain —(OCH$_2$CH$_2$)$_{1-6}$—, which chains may be interrupted by one or more hetero-atoms and/or C$_{3-20}$ heteroaryl and/or C$_{5-20}$ aryl groups;

X' is selected from O, S, NR", =CR"—, CR"R"', CR"R"'O, C(=O), C(=O)NR', NR"C(=O), O—C(O) and C(O)—O or is absent; and D has the formula (II) or (III):

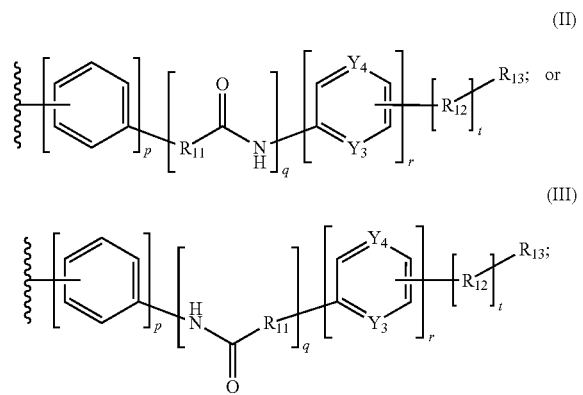

p is 0 or 1;
q is 1, 2, 3, 4, 5 or 6;
r is 0 or 1;
t is 0 or 1
Y$_3$ is N or CH;
Y$_4$ is N or CH; wherein at least one of Y$_3$ and Y$_4$ is CH;
R$_{13}$ is H, Z—R", Z—CO$_2$R", Z—C(=O)—NH—(CH$_2$)$_{1-6}$—NR"R"', and Z—C(=O)—NH—(CH$_2$)$_{1-6}$—C(=NH)NR"R"';

Z is absent or is selected from C$_{3-20}$ heteroaryl, C$_{1-6}$ alkyl substituted C$_{3-20}$ heteroaryl, —(CH$_2$)$_k$—C$_{3-20}$ heterocyclyl, and —O—(CH$_2$)$_k$—C$_{3-20}$ heterocyclyl group;

k is 0, 1, 2, 3 or 4;
each R" and R"' is independently selected from H, and optionally substituted C$_{1-12}$ alkyl;
R$_{11}$ is an optionally substituted C$_{3-20}$ heteroaryl; and
R$_{12}$ is an optionally substituted C$_{3-20}$ heteroaryl.

Hence, all of the compounds of formula (I) contain a 6-membered C-ring and may contain either a 7-membered or 8-membered B-ring.

In a further aspect, there is provided a compound of the present invention for use in a method of therapy.

In a further aspect, there is provided a compound of the present invention for use in the treatment of a proliferative disease.

In a further aspect, there is provided a pharmaceutical composition comprising a compound of the present invention and a pharmaceutically acceptable carrier or diluent.

In a further aspect, the present invention provides the use of a compound of the present invention in the manufacture of a medicament for treating a proliferative disease.

In a further aspect, the compound of formula (I) and salts or solvates thereof, may be linked, either directly or indirectly, to a targeting agent (e.g., antibody, antibody fragment, hormone, etc.) to provide a targeted conjugate. The target conjugates of the present disclosure may contain one or multiple compounds of formula (I) (or salts and solvates thereof). A variety of target conjugates are known in the art and may be used with a compound of formula (I) and salts or solvates thereof. For example, in a particular aspect the target conjugate is an antibody-drug conjugate, wherein one or more compounds of formula (I) are linked, directly or indirectly, to the antibody. Therefore, the compound of formula (I) and salts or solvates thereof, may be used as a payload on a targeted conjugate.

Definitions

The following abbreviations are used throughout the specification: Ac acetyl; Alloc allyloxycarbonyl; BAIB bis (acetoxy)iodobenzene/(diacetoxyiodo)benzene; Boc tert-butoxycarbonyl; BPDs benzopyrridodiazecines; CBz benzyloxycarbonyl; DBU 1,8-diazabicyclo[5.4.0]undec-7-ene; DHP dihydropyran; DMAP 4-dimethylaminopyridine; DMF dimethylformamide; DMSO dimethylsulfoxide; EDCl 1-Ethyl-3-(3-dimethylaminopropyl)carbodiimide; Et ethyl; Et$_2$O diethyl ether; EtOAc ethyl acetate; EtOH ethanol; HATU (1-[Bis(dimethylamino)methylene]-1H-1,2,3-triazolo[4,5-b]pyridinium 3-oxid hexafluorophosphate); HMDST hexamethyldisilathiane; iBu iso-butyl; KOtBu potassium t-butoxide; L-Selectride Lithium tri-sec-butyl(hydride)borate; Me methyl; MeOH methanol; PBDs pyrrolo [2,1-c][1,4]benzo-diazepines; PDDs pyrridinobenzodiazepines; PIFA phenyliodine (III) bis[trifluoroacetate]; Ph phenyl; p-TSA/PTSA p-Toluenesulfonic acid; Pyr pyridine; TBAF tetrabutylammonium fluoride; TBS-Cl/TBDMSCl tert-butyldimethylsilyl chloride; TEA triethylamine; TEMPO (2,2,6,6-tetramethyl-piperidin-1-yl)oxyl; TFA trifluoroacetic acid; THF tetrahydrofuran; THP tetrahydropyranyl; Troc 2,2,2-Trichloroethyl carbonate and Ts (tosylate) p-toluene sulfonic acid.

"Optionally substituted" refers to a parent group which may be unsubstituted or which may be substituted with one or more substituents. Suitably when optional substituents are present the optional substituted parent group comprises from one to three optional substituents.

"Substituted", when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

"Independently selected" is used in the context of statement that, for example, "R and R' are independently selected from C$_{1-12}$ alkyl, C$_{2-12}$ alkenyl, etc." and means that each instance of the functional group R or R' is selected from the listed options independently of any other instance of R or R' in the compound. Hence, for example, a C$_{1-12}$ alkyl may be selected for the first instance of R in the compound and a C$_{2-12}$ alkenyl may be selected for the next instance of R in the compound.

Examples of optional substituents include C$_{1-7}$ alkyl, C$_{2-7}$ alkenyl, C$_{2-7}$ alkynyl, C$_{5-20}$ aryl, C$_{3-10}$ cycloalkyl, C$_{3-10}$ cycloalkenyl, C$_{3-10}$ cycloalkynyl, C$_{3-20}$ heterocyclyl, C$_{3-20}$ heteroaryl, acetal, acyl, acylamido, acyloxy, amidino, amido, amino, aminocarbonyloxy, azido, carboxy, cyanato, cyano, disulphide, ether, formyl, guanidino, halo, hemiacetal, hemiketal, hydroxamic acid, hydroxyl, imidic acid, imino, isocyano, isocyanato, isothiocyano, ketal, nitro, nitroso, oxo, oxycarbonyl, oxycarboyloxy, phosphate, phosphino, phosphinyl, phosphite, phospho, phosphonate, phosphono, phosphonooxy, phosphorous acid, phosphoramidate, phosphoramidite, sulfamino, sulfamyl, sulfate, sulfhydryl, sulfinamino, sulfinate, sulfino, sulfinyl, sulfinyloxy, sulfo, sulfonamido, sulfonamino, sulfonate, sulfonyl, sulfonyloxy, thioamido, thiocarboxy, thiocyano, thioether, thiolocarboxy, thione, thionocarboxy, uredio, hydroxyl protecting groups and nitrogen protecting groups.

More suitably, the optional substituents may be selected from C$_{1-7}$ alkyl, C$_{2-7}$ alkenyl, C$_{2-7}$ alkynyl, C$_{5-20}$ aryl, C$_{3-10}$ cycloalkyl, $C_{3-10}$ cycloalkenyl, $C_{3-10}$ cycloalkynyl, $C_{3-20}$ heterocyclyl, $C_{3-20}$ heteroaryl, acetal, acyl, acylamido, acyloxy, amidino, amido, amino, aminocarbonyloxy, azido, carboxy, cyano, ether, formyl, guanidino, halo, hemiacetal, hemiketal, hydroxamic acid, hydroxyl, imidic acid, imino, ketal, nitro, nitroso, oxo, oxycarbonyl, oxycarboyloxy, sulfamino, sulfamyl, sulfate, sulfhydryl, sulfinamino, sulfinate, sulfino, sulfinyl, sulfinyloxy, sulfo, sulfonamido, sulfonamino, sulfonate, sulfonyl, sulfonyloxy, uredio, hydroxyl protecting groups and nitrogen protecting groups.

Examples of substituents are described in more detail below.

$C_{1-12}$ alkyl: refers to straight chain and branched saturated hydrocarbon groups, generally having from 1 to 12 carbon atoms; more suitably $C_{1-7}$ alkyl; more suitably $C_{1-6}$ alkyl. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like.

"Alkylene" refers to a divalent radical derived from an alkane which may be a straight chain or branched, as exemplified by —$CH_2CH_2CH_2CH_2$—.

$C_{2-12}$ alkenyl: refers to a hydrocarbon radical having from 2 to 12 carbon atoms and at least one double bond including, but not limited to, ethenyl, 1-propenyl, 2-propenyl, isopropenyl, 1-butenyl, 2-butenyl, 3-butenyl, pentenyl and hexenyl and the like.

The term "alkenylene" refers to a divalent radical derived from an alkenyl which may be a straight chain or branched, containing one or more double bonds, as exemplified by, —$CH_2CH=CH$—, or —$CH_2CH(CH_3)CH=CH$—$CH_2$—.

$C_{2-12}$ alkynyl: refers to a hydrocarbon radical having from to 2 to 12 carbon atoms and at least one triple bond including, but not limited to, ethynyl, 2-propynyl, 1-butynyl, 2-butynyl and the like.

$C_{5-20}$ aryl: refers to fully unsaturated monocyclic, bicyclic and polycyclic aromatic hydrocarbons having at least one aromatic ring and having a specified number of carbon atoms that comprise their ring members (e.g., $C_{6-14}$ aryl refers to an aryl group having 6 to 14 carbon atoms as ring members). The aryl group may be attached to a parent group or to a substrate at any ring atom and may include one or more non-hydrogen substituents unless such attachment or substitution would violate valence requirements. Examples of aryl groups include phenyl, biphenyl, cyclobutabenzenyl, naphthalenyl, benzocycloheptenyl, azulenyl, biphenylenyl, anthracenyl, phenanthrenyl, naphthacenyl, pyrenyl, groups derived from cycloheptatriene cation, and the like. Examples of aryl groups which comprise fused rings, at least one of which is an aromatic ring, include, but are not limited to, groups derived from indanyl, indenyl, isoindenyl, tetralinyl, acenaphthenyl, fluorenyl, phenalenyl, acephenanthrenyl and aceanthrenyl.

$C_{3-10}$ cycloalkyl: refers to saturated monocyclic and bicyclic hydrocarbon groups, having from 3 to 10 carbon atoms that comprise the ring or rings. Thus, a cycloalkyl represents a cyclic version of an "alkyl". Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached to a parent group or to a substrate at any ring atom unless such attachment would violate valence requirements. Suitably the $C_{3-10}$ cycloalkyl is a monocyclic cycloalkyl group, more suitably a $C_{3-7}$ cycloalkyl is a monocyclic cycloalkyl group.

Examples of monocyclic cycloalkyl groups include cyclopropyl, cyclobutyl, cyclopentyl, cyclohexyl, cycloheptyl, methylcyclopropyl, dimethylcyclopropyl, methylcyclobutyl, dimethylcyclobutyl, methylcyclopentyl, dimethylcyclopentyl and methylcyclohexyl and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, etc.

$C_{3-10}$ cycloalkenyl: represents a cycloalkyl that contains at least one double bond, including unsaturated monocyclic hydrocarbon compounds such as cyclopropenyl, cyclobutenyl, cyclopentenyl, cyclohexenyl, methylcyclopropenyl, dimethylcyclopropenyl, methylcydobutenyl, dimethylcydobutenyl, methylcydopentenyl, dimethylcydopentenyl and methylcydohexenyl $C_{3-10}$ cycloalkynyl: represents a cycloalkyl that contains at least one triple bond, including unsaturated monocyclic hydrocarbon compounds such as cyclopropynyl, cyclobutynyl, cyclopentynyl, cyclohexynyl and the like.

"$C_{3-20}$ heterocyclyl": refers to saturated or partially unsaturated monocyclic, bicyclic or polycyclic groups having ring atoms composed of 3 to 20 ring atoms, whether carbon atoms or heteroatoms, of which from 1 to 10 are ring heteroatoms. Suitably, each ring has from 3 to 7 ring atoms and from 1 to 4 ring heteroatoms (e.g., suitably $C_{3-5}$ heterocyclyl refers to a heterocyclyl group having 3 to 5 ring atoms and 1 to 4 heteroatoms as ring members). The ring heteroatoms are independently selected from nitrogen, oxygen, and sulphur.

As with bicyclic cycloalkyl groups, bicyclic heterocyclyl groups may include isolated rings, spiro rings, fused rings, and bridged rings. The heterocyclyl group may be attached to a parent group or to a substrate at any ring atom and may include one or more non-hydrogen substituents unless such attachment or substitution would violate valence requirements or result in a chemically unstable compound.

Examples of monocyclic heterocyclyl groups include, but are not limited to, those derived from:

$N_1$: aziridine, azetidine, pyrrolidine, pyrroline, 2H-pyrrole or 3H-pyrrole, piperidine, dihydropyridine, tetrahydropyridine, azepine;

$O_1$: oxirane, oxetane, tetrahydrofuran, dihydrofuran, tetrahydropyran, dihydropyran, pyran, oxepin;

$S_1$: thiirane, thietane, tetrahydrothiophene, tetrahydrothiopyran, thiepane;

$O_2$: dioxoiane, dioxane, and dioxepane;

$O_3$: trioxane;

$N_2$: imidazoiidine, pyrazolidine, imidazoline, pyrazoline, piperazine;

$N_1O_1$: tetrahydrooxazole, dihydrooxazole, tetrahydroisoxazole, dihydroisoxazole, morpholine, tetrahydrooxazine, dihydrooxazine, oxazine;

$N_1S_1$: thiazoline, thiazolidine, thiomorpholine;

$N_2O_1$: oxadiazine;

$O_1S_1$: oxathiole and oxathiane (thioxane); and $N_1O_1S_1$: oxathiazine.

Examples of substituted monocyclic heterocyclyl groups include those derived from saccharides, in cyclic form, for example, furanoses, such as arabinofuranose, lyxofuranose, ribofuranose, and xylofuranse, and pyranoses, such as aliopyranose, altropyranose, glucopyranose, mannopyranose, gulopyranose, idopyranose, galactopyranose, and talopyranose.

"$C_{3-20}$ Heteroaryl": refers to unsaturated monocyclic, bicyclic or polycylic aromatic groups comprising from 3 to 20 ring atoms, whether carbon or heteroatoms, of which from 1 to 10 are ring heteroatoms. Suitably, each ring has from 3 to 7 ring atoms and from 1 to 4 ring heteroatoms. Suitably each ring heteroatom is independently selected from nitrogen, oxygen, and sulfur. The bicyclic and polycyclic may include any bicyclic or polycyclic group in which any of the above-listed monocyclic heterocycles are fused to a benzene ring. The heteroaryl group may be attached to a parent group or to a substrate at any ring atom and may include one or more non-hydrogen substituents unless such attachment or substitution would violate valence requirements or result in a chemically unstable compound.

Examples of monocyclic heteroaryl groups include, but are not limited to, those derived from:

$N_1$: pyrrole, pyridine;

$O_1$: furan;

$S_1$: thiophene;

$N_1O_1$: oxazole, isoxazole, isoxazine;

$N_2O_1$: oxadiazole (e.g. 1-oxa-2,3-diazolyl, 1-oxa-2,4-diazolyl, 1-oxa-2,5-diazolyl, 1-oxa-3,4-diazolyl);

$N_3O_1$: oxatriazole;

$N_1S_1$: thiazole, isothiazole;

$N_2$: imidazole, pyrazole, pyridazine, pyrimidine (e.g., cytosine, thymine, uracil), pyrazine;

$N_3$: triazole, triazine; and, $N_4$: tetrazole.

Examples of heteroaryl which comprise fused rings, include, but are not limited to, those derived from:

$O_1$: benzofuran, isobenzofuran, chromene, isochromene, chroman, isochroman, dibenzofuran, xanthene;

$N_1$: indole, isoindole, indolizine, isoindoline, quinoline, isoquinoline, quinolizine, carbazole, acridine, phenanthridine;

$S_1$: benzothiofuran, dibenzothiophene, thioxanthene;

$N_1O_1$: benzoxazole, benzisoxazole, benzoxazine, phenoxazine;

$N_1S_1$: benzothiazole, phenothiazine;

$O_1S_1$: phenoxathiin;

$N_2$: benzimidazole, indazole, benzodiazine, pyridopyridine, quinoxaline, quinazoline, cinnoline, phthalazine, naphthyridine, benzodiazepine, carboline, perimidine, pyridoindole, phenazine, phenanthroline, phenazine;

$O_2$: benzodioxole, benzodioxan, oxanthrene;

$S_2$: thianthrene $N_2O_1$: benzofurazan;

$N_2S_1$: benzothiadiazole $N_3$: benzotriazole $N_4$: purine (e.g., adenine, guanine), pteridine.

The optional substituents $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, whether alone or part of another substituent, may themselves optionally be substituted with one or more groups (suitably, optionally substituted with from one to three) selected from themselves and from acetal, acyl, acylamido, acyloxy, amidino, amido, amino, aminocarbonyloxy, azido, carboxy, cyanato, cyano, disulphide, ether, formyl, guanidino, halo, hemiacetal, hemiketal, hydroxamic acid, hydroxyl, imidic acid, imino, isocyano, isocyanato, isothiocyano, ketal, nitro, nitroso, oxo, oxycarbonyl, oxycarboyloxy, phosphate, phosphino, phosphinyl, phosphite, phospho, phosphonate, phosphono, phosphonooxy, phosphorous acid, phosphoramidate, phosphoramidite, sulfamino, sulfamyl, sulfate, sulfhydryl, sulfinamino, sulfinate, sulfino, sulfinyl, sulfinyloxy, sulfo, sulfonamido, sulfonamino, sulfonate, sulfonyl, sulfonyloxy, thioamido, thiocarboxy, thiocyano, thioether, thiolocarboxy, thione, thionocarboxy, uredio, hydroxyl protecting groups and nitrogen protecting groups.

For example, when an alkyl group is optionally substituted with one or more aryl groups it forms aralkyl group. Suitably a $C_{6-32}$ aralkyl where the alkyl group and aryl group(s) combined have from 6 to 32 carbon atoms. Similarly, when an alkyl group is optionally substituted with one or more heteroaryl groups it forms heteroaralkyl group.

Suitably a $C_{4-32}$ heteroaralkyl group where number of ring atoms in the heteroaryl group plus the number of carbon atoms in the alkyl group is from 4 to 32.

Examples of substituents are described in more detail below.

Acetal: —CHC(OR$^{X1}$)(OR$^{X2}$), wherein R$^{X1}$ and R$^{X2}$ are independently acetal substituents, for example, a $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, suitably a $C_{1-7}$ alkyl, or, in the case of a "cyclic" acetal group, R$^{X1}$ and R$^{X2}$, taken together with the two oxygen atoms to which they are attached, and the carbon atoms to which they are attached, form a heterocyclic ring having from 4 to 8 ring atoms. Examples of acetal groups include, but are not limited to, —CH(OCH$_3$)$_2$, —CH(OCH$_2$CH$_3$)$_2$, and —CH(OCH$_3$)(O CH$_2$CH$_3$).

Acyl: —C(=O)R$^{X3}$, wherein R$^{X3}$ is an acyl substituent, for example, a $C_{1-7}$ alkyl (also referred to as $C_{1-7}$ alkylacyl or $C_{1-7}$ alkanoyl), $C_{2-7}$ alkenyl, $C_{2-7}$ alkynyl, $C_{5-20}$ aryl (also referred to as $C_{5-20}$ arylacyl), $C_{3-10}$ cycloalkyl, $C_{3-10}$ cycloalkenyl, $C_{3-10}$ cycloalkynyl, $C_{3-20}$ heterocyclyl (also referred to as $C_{3-20}$ heterocyclyl acyl), $C_{3-20}$ heteroaryl (also referred to as $C_{3-20}$ heteroarylacyl), more suitably a $C_{1-7}$ alkyl. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Acylamido: —NR$^{X4}$C(=O)R$^{X5}$, wherein R$^{X4}$ and R$^{X5}$ are suitably independently selected from a hydrogen, a $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, suitably a hydrogen or a $C_{1-7}$ alkyl, or, in the case of a "cyclic" acylamido group, R$^{X4}$ and R$^{X5}$, taken together with the nitrogen atom to which they are attached, and the carbon atoms to which they are attached, form a heterocyclic ring having from 4 to 8 ring atoms. Examples of acylamido groups include, but are not limited to, —NHC(=O)CH$_3$, —NHC(=O)CH$_2$CH$_3$, —NHC(=O)Ph; and the cyclic groups succinimidyl, maleimidyl, and phthalimidyl:

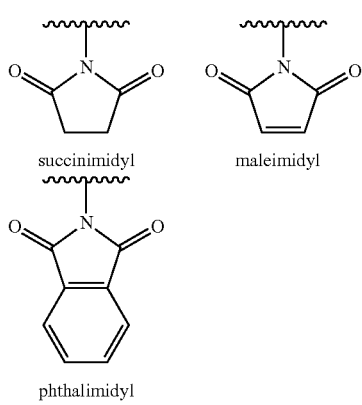

succinimidyl    maleimidyl phthalimidyl

Acyloxy (reverse ester): —OC(=O)$R^{X3}$, wherein $R^{X3}$ is an acyloxy substituent and suitably has any of the options listed above with regard to acyl groups. Examples of acyloxy groups include, but are not limited to, —OC(=O)$CH_3$ (acetoxy), —OC(=O)$CH_2CH_3$, —OC(=O)C($CH_3$)$_3$, —OC(=O)Ph, and —OC(=O)$CH_2$Ph.

Amidino: —C(=$NR^{X6}$)$NR^{X4}R^{X5}$, wherein $R^{X4}$ and $R^{X5}$ are suitably independently selected from the groups as listed above for acylamido, and wherein $R^{X6}$ is selected from a hydrogen, a $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, suitably a hydrogen or a $C_{1-7}$ alkyl. Examples of amidine groups include, but are not limited to, —C(=NH)$NH_2$, —C(=NH)N($CH_3$)$_2$ and —C(=$NCH_3$)N($CH_3$)$_2$.

Amido: —C(=O)$NR^{X4}R^{X5}$, wherein $R^{X4}$ and $R^{X5}$ are suitably independently selected from the groups as listed above for acylamido. Examples of amido groups include, but are not limited to, —C(=O)$NH_2$, —C(=O)$NHCH_3$, —C(=O)N($CH_3$)$_2$, —C(=O)$NHCH_2CH_3$, and —C(=O)N($CH_2CH_3$)$_2$, as well as amido groups in which $R^{X4}$ and $R^{X5}$, together with the nitrogen atom to which they are attached, form a heterocyclic structure as in, for example, piperidinocarbonyl, morpholinocarbonyl, thiomorpholinocarbonyi, and piperazinocarbonyl.

Amino: —$NR^{X4}R^{X5}$, wherein $R^{X4}$ and $R^{X5}$ are suitably independently selected from the groups as listed above for acylamido. Amino groups may be primary (both $R^{X4}$ and $R^{X5}$ are H), secondary (only one of $R^{X4}$ and $R^{X5}$ is H), or tertiary (neither $R^{X4}$ and $R^{X5}$ is H), and in cationic form, may be quaternary (—$^+NR^{X4}R^{X5}R^{X6}$ wherein $R^{X6}$ is suitably selected from the same groups as listed above for amidino). Examples of amino groups include, but are not limited to, —$NH_2$, —$NHCH_3$, —NHC($CH_3$)$_2$, —N($CH_3$)$_2$—N($CH_2CH_3$)$_2$, and —NHPh. Examples of cyclic amino groups include, but are not limited to, aziridino, azetidino, pyrrolidino, piperidino, piperazino, morpholino, and thiomorpholino.

Aminocarbonyloxy: —OC(=O)$NR^{X4}R^{X5}$, wherein $R^{X4}$ and $R^{X5}$ are suitably independently selected from the groups as listed above for acylamido. Examples of aminocarbonyloxy groups include, but are not limited to, —OC(=O)$NH_2$, —OC(=O)$NHCH_3$, —OC(=O)N($CH_3$)$_2$, and —OC(=O)N($CH_2CH_3$)$_2$.

Azido: —$N_3$.
Carboxy: —C(=O)OH
Cyanato: —OCN.
Cyano: —CN.

Disulfide: —SS—$R^{X3}$, wherein $R^{X3}$ is suitably selected from the groups as listed above for acyl. Examples of disulphide groups include $C_{1-7}$ alkyl disulfide groups which include, but are not limited to, —$SSCH_3$ and —$SSCH_2CH_3$.

Ether: —$OR^{X3}$, wherein $R^{X3}$ is suitably selected from the groups as listed above for acyl. More suitably, $R^{X3}$ is an alkyl group, for example, a $C_{1-7}$ alkyl group, resulting in —$OR^{X3}$ being an alkoxy group. Examples of $C_{1-7}$ alkoxy groups include, but are not limited to, —$OCH_3$ (methoxy), —$OCH_2CH_3$ (ethoxy), —$OCH_2CH_2CH_3$ (n-propoxy), —$OCH_2(CH_3)_2$ (isopropoxy), —$OCH_2CH_2CH_2CH_3$ (n-butoxy), —O(OCH($CH_3$)—$CH_2CH_3$ (sec-butoxy), —$OCH_2CH(CH_3)_2$ (isobutoxy), and —OC($CH_3$)$_3$ (tert-butoxy).

Formyl: —C(=O)H.
Guanidino: —NH—C(=NH)$NH_2$.
Halo: —F, —Cl, —Br, and —I.
Hemiacetal: —CH(OH)(O$R^{X3}$), wherein $R^{X3}$ is suitably selected from the groups as listed above for acyl. Examples of hemiacetal groups include, but are not limited to, —CH(OH)(O$CH_3$) and —CH(OH)(O$CH_2CH_3$).

Hemiketal: —C$R^{X3}$(OH)(O$R^{X3}$), wherein each $R^{X3}$ is suitably independently selected from the groups as listed above for acyl. Examples of hemiketal groups include, but are not limited to, —C($CH_3$)(OH)(O$CH_3$), —C($CH_2CH_3$)(OH)(O$CH_3$), —C($CH_3$)(OH)(O$CH_2CH_3$), and —C($CH_2CH_3$)(OH)(O$CH_2CH_3$).

Hydroxamic acid: —C(=NOH)OH.
Hydroxyl: —OH.
Imidic acid: —C(=NH)OH.
Imino: =$NR^{X4}$, wherein $R^{X4}$ is suitably selected from the groups as listed above for acylamido. Examples of imino groups include, but are not limited to, =NH, =$NCH_3$, =$NCH_2CH_3$, and =NPh.

Isocyano: —NC.
Isocyanato: —NCO.
Isothiocyano: —NCS.
Ketal: —C$R^{X3}$(O$R^{X1}$)(O$R^{X2}$), where $R^{X1}$ and $R^{X2}$ are suitably selected from the groups as listed above for acetals, and $R^{X3}$ is suitably selected from the groups as listed above for acyl. Examples ketal groups include, but are not limited to, —C($CH_3$)(O$CH_3$)$_2$, —C($CH_3$)(O$CH_2CH_3$)$_2$, —C($CH_3$)(O$CH_3$)(O$CH_2CH_3$), —C($CH_2CH_3$)(O$CH_3$)$_2$, —C($CH_2CH_3$)(O $CH_2CH_3$)$_2$, and —C($CH_2CH_3$)(O$CH_3$) (O$CH_2CH_3$).

Nitro: —$NO_2$.
Nitroso: —NO.
Oxo: =O.
Oxycarbonyl (ester): —C(=O)O$R^{X3}$, wherein $R^{X3}$ is suitably selected from the groups as listed above for acyl. Examples of ester groups include, but are not limited to, —C(=O)O$CH_3$, —C(=O)O$CH_2CH_3$, —C(=O)OC($CH_3$)$_3$, and —C(=O)OPh.

Oxycarboyloxy: —OC(=O)O$R^{X3}$, where $R^{X3}$ is suitably selected from the groups as listed above for acyl. Examples of oxycarboyloxy groups include, but are not limited to, —OC(=O)O$CH_3$, —OC(=O)O$CH_2CH_3$, —OC(=O)OC($CH_3$)$_3$, and —OC(=O)OPh.

Phosphate: OP(=O)(O$R^{X7}$)(O$R^{X8}$), wherein $R^{X7}$ and $R^{X8}$ are suitably independently selected from hydrogen, $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, suitably hydrogen, $C_{1-7}$ alkyl, $C_{5-20}$ aryl or $C_{3-20}$ heteroaryl. Examples of phosphate groups include, but are not limited to, —OP(=O)(O$CH_3$)$_2$, —OP(=O)(O$CH_2CH_3$)$_2$, —OP(=O)[OC($CH_3$)$_3$]$_2$ and —OP(=O)(OPh)$_2$.

Phosphino: —PR$^{X7}$R$^{X8}$, wherein R$^{X7}$ and R$^{X8}$ are suitably selected from the groups as listed above for phosphate. Examples of phosphino groups include, but are not limited to, —PH$_2$, —P(CH$_3$)$_2$, —P(CH$_2$CH$_3$)$_2$, —P(C(CH$_3$)$_3$)$_2$, and —P(Ph)$_2$.

Phosphinyl: P(=O)R$^{X9}$R$^{X10}$), wherein R$^{X9}$ and R$^{X10}$ are suitably independently selected from C$_{1-7}$ alkyl, C$_{2-7}$ alkenyl, C$_{2-7}$ alkynyl, C$_{5-20}$ aryl, C$_{3-10}$ cycloalkyl, C$_{3-10}$ cycloalkenyl, C$_{3-10}$ cycloalkynyl, C$_{3-20}$ heterocyclyl, C$_{3-20}$ heteroaryl, suitably C$_{1-7}$ alkyl, C$_{5-20}$ aryl or C$_{3-20}$ heteroaryl. Examples of phosphinyl groups include, but are not limited to, —P(=O)(CH$_3$)$_2$, —P(=O)(CH$_2$CH$_3$)$_2$, —P(=O)[C(CH$_3$)$_3$]$_2$ and —P(=O)(Ph)$_2$.—

Phosphite: —OP(OR$^{X7}$)(OR$^{X8}$), wherein R$^{X7}$ and R$^{X8}$ are suitably selected from the groups as listed above for phosphate. Examples of phosphite groups include, but are not limited to, —OP(OCH$_3$)$_2$, —OP(OCH$_2$CH$_3$)$_2$, —OP[OC(CH$_3$)$_3$]$_2$ and —OP(OPh)$_2$.—

Phospho: —P(=O)$_2$.

Phosphonate: —P(=O(OR$^{X7}$)(OR$^{X8}$), wherein R$^{X7}$ and R$^{X8}$ are suitably selected from the groups as listed above for phosphate. Examples of phosphonate groups include, but are not limited to, —P(=O)(OCH$_3$)$_2$, —P(=O)(OCH$_2$CH$_3$)$_2$, —P(=O)[OC(CH$_3$)$_3$]$_2$ and —P(=O)(OPh)$_2$.

Phosphono: —P(=O)(OH)$_2$.

Phosphonooxy: —OP(=O)(OH)$_2$.

Phosphorous acid: —OP(OH)$_2$.

Phosphoramidate: —OP(=O)(OR$^{X11}$)—NR$^{X12}$R$^{X13}$, where R$^{X11}$, R$^{X12}$ and R$^{X13}$ are phosphoramidate substituents, for example, H, C$_{1-7}$ alkyl (optionally substituted), C$_{2-7}$ alkenyl (optionally substituted), C$_{2-7}$ alkynyl (optionally substituted), C$_{5-20}$ aryl, C$_{3-10}$ cycloalkyl, C$_{3-10}$ cycloalkenyl, C$_{3-10}$ cycloalkynyl, C$_{3-20}$ heterocyclyl, C$_{3-20}$ heteroaryl, suitably H, C$_{1-7}$ alkyl, a C$_{5-20}$ aryl or a C$_{3-20}$ heteroaryl. Examples of phosphoramidate groups include, but are not limited to, —OP(=O)(OCH$_2$CH$_3$)—N(CH$_3$)$_2$, —OP(=O)(OCH$_2$CH$_3$)—N[CH(CH$_3$)$_2$]$_2$, and —OP(=O)(OCH$_2$CH$_2$CN)—N[CH(CH$_3$)$_2$]$_2$.

Phosphoramidite: —OP(OR$^{X11}$)—NR$^{X12}$R$^{X13}$, where R$^{X11}$, R$^{X12}$ and R$^{X13}$ are suitably selected from the groups as listed above for phosphoramidate. Examples of phosphoramidite groups include, but are not limited to, —OP(OCH$_2$CH$_3$)—N(CH$_3$)$_2$, —OP(OCH$_2$CH$_3$)—N[CH(CH$_3$)$_2$]$_2$, and —OP(OCH$_2$CH$_2$CN)—N[CH(CH$_3$)$_2$]$_2$.

Sulfamino: —NR$^{X3}$S(=O)$_2$OH, wherein R$^{X3}$ is suitably selected from the groups as listed above for acyl groups. Examples of sulfamino groups include, but are not limited to, —NHS(=O)$_2$OH and —N(CH$_3$)S(=O)$_2$OH.

Sulfamyl: —S(=O)NR$^{X4}$R$^{X5}$, wherein R$^{X4}$ and R$^{X5}$ are suitably independently selected from the groups as listed above for acylamido. Examples of sulfamyl groups include, but are not limited to, —S(=O)NH$_2$, —S(=O)NHCH$_3$, —S(=O)N(CH$_3$)$_2$, —S(=O)NHCH$_2$CH$_3$, —S(=O)N(CH$_2$CH$_3$)$_2$, and —S(=O)NHPh.

Sulfate: —OS(=O)$_2$OR$^{X3}$; wherein R$^{X3}$ is suitably selected from the groups as listed above for acyl groups. Examples of sulfate groups include, but are not limited to, —OS(=O)$_2$OCH$_3$ and —OS(=O)$_2$OCH$_2$CH$_3$.

Sulfhydryl: —SH.

Sulfinamino: —NR$^{X3}$S(=O)R$^{X4}$, wherein R$^{X3}$ is suitably selected from the groups as listed above for acyl groups, and R$^{X4}$ is suitably selected from the groups as listed above for acylamido. Examples of sulfinamino groups include, but are not limited to, —NHS(=O)CH$_3$ and —N(CH$_3$)S(=O)Ph.

Sulfinate: —S(=O)OR$^{X3}$; wherein R$^{X3}$ is suitably selected from the groups as listed above for acyl groups. Examples of sulfinate groups include, but are not limited to, —S(=O)OCH$_3$ and —S(=O)OCH$_2$CH$_3$.

Sulfino: —S(=O)OH, —SO$_2$H.

Sulfinyl: —S(=O)R$^{X3}$; wherein R$^{X3}$ is suitably selected from the groups as listed above for acyl groups. Examples of sulfinyl groups include, but are not limited to, —S(=O)CH$_3$ and —S(=O)CH$_2$CH$_3$.

Sulfinyloxy: —OS(=O)R$^{X3}$; wherein R$^{X3}$ is suitably selected from the groups as listed above for acyl groups. Examples of sulfinyloxy groups include, but are not limited to, —OS(=O) CH$_3$ and —OS(=O)CH$_2$CH$_3$.

Sulfo: —S(=O)$_2$OH, —SO$_3$H.

Sulfonamido: —S(=O)$_2$NR$^{X4}$R$^{X5}$, wherein R$^{X4}$ and R$^{X5}$ are suitably independently selected from the groups as listed above for acylamido. Examples of sulfonamido groups include, but are not limited to, —S(=O)$_2$NH$_2$, —S(=O)$_2$NHCH$_3$, —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfonamino: —NR$^{X4}$S(=O)$_2$R$^{X3}$, where R$^{X3}$ is suitably selected from the groups as listed above for acyl groups and R$^{X4}$ is suitably selected from the groups as listed above for acylamido. Examples of sulfonamino groups include, but are not limited to, —NHS(=O)$_2$CH$_3$ and —N(CH$_3$)S(=O)$_2$Ph.

Sulfonate: —S(=O)$_2$R$^{X3}$, where R$^{X3}$ is suitably selected from the groups as listed above for acyl groups. Examples of sulfonate groups include, but are not limited to, —S(=O)$_2$OCH$_3$ and —S(=O)$_2$OCH$_2$CH$_3$.

Sulfonyl: —S(=O)$_2$R$^{X3}$, where R$^{X3}$ is suitably selected from the groups as listed above for acyl groups. More suitably R$^{X3}$ is a C$_{1-7}$ alkyl group, including, for example, a fluorinated or perfluorinated C$_{1-7}$ alkyl group. Examples of sulfone groups include, but are not limited to, —S(=O)$_2$CH$_3$, —S(=O)$_2$CF$_3$, —S(=O)$_2$CH$_2$CH$_3$, —S(=O)$_2$C$_4$F$_9$, —S(=O)$_2$CH$_2$CF$_3$, —S(=O)$_2$CH$_2$CH$_2$NH$_2$, —S(=O)$_2$Ph, 4-methylphenylsulfonyl (tosyl), 4-chlorophenyl-sulfonyl (closyl), 4-bromophenylsulfonyl (brosyl), 4-nitrophenyl (nosyl), 2-naphthalenesulfonate (napsyl), and 5-dimethylaminonaphthalen-1-ylsulfonate (dansyl).

Sulfonyloxy: —OS(=O)$_2$R$^{X3}$, where R$^{X3}$ is suitably selected from the groups as listed above for acyl groups. Examples of sulfonyloxy groups include, but are not limited to, —OS(=O)$_2$CH$_3$ and —OS(=O)$_2$ CH$_2$CH$_3$.

Thioamido: —C(=S)NR$^{X4}$R$^{X5}$, where R$^{X4}$ and R$^{X5}$ are suitably independently selected from the groups as listed above for acylamido. Examples of amido groups include, but are not limited to, —C(=S)NH$_2$, —C(=S)NHCH$_3$, —C(=S)N(CH$_3$)$_2$, —C(=S)NHCH$_2$CH$_3$, and —C(=S)N(CH$_2$CH$_3$)$_2$.

Thiocarboxy: —C(=S)SH.

Thiocyano: —SCN.

Thioether: —SR$^{X3}$, wherein R$^{X3}$ is suitably selected from the groups as listed above for acyl. Examples of thioether groups include, but are not limited to, —SCH$_3$ and —SCH$_2$CH$_3$.

Thiolocarboxy: —C(=O)SH.

Thione: =S.

Thionocarboxy: —C(=S)OH.

Ureido: —N(R$^{X6}$)CONR$^{X4}$R$^{X5}$, wherein R$^{X4}$ and R$^{X5}$ are suitably independently selected from the groups as listed above for acylamido, and R$^{X6}$ is suitably selected from the groups listed above for amidino. Examples of ureido groups include, but are not limited to, —NHCONH$_2$, —NHCONHCH$_3$, —NHCONHCH$_2$CH$_3$, NHCON(CH$_3$)$_2$, NHCON(CH$_2$CH$_3$)$_2$, —NCH$_3$CONH$_2$, —NCH$_3$CONHCH$_3$, —NCH$_3$CONHCH$_2$CH$_3$, —NCH$_3$CON(CH$_3$)$_2$, and —NCH$_3$CON(CH$_2$CH$_3$)$_2$.

Nitrogen Protecting Groups

Nitrogen protecting groups are well known in the art. Preferred nitrogen protecting groups are carbamate protecting groups that have the general formula:

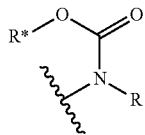

A large number of possible carbamate nitrogen protecting groups are listed on pages 706 to 771 of Wuts, P. G. M. and Greene, T. W., Protective Groups in Organic Synthesis, 4$^{th}$ Edition, Wiley-lnterscience, 2007, and in P. Kocienski, *Protective Groups,* 3rd Edition (2005) which are incorporated herein by reference.

Particularly preferred protecting groups include Alloc (allyloxycarbonyl), Troc (2,2,2-Trichloroethyl carbonate), Teoc [2-(Trimethylsilyl)ethoxycarbony], BOC (tert-butyloxycarbonyl), Doc (2,4-dimethylpent-3-yloxycarbonyl), Hoc (cyclohexyloxy-carbonyl), TcBOC (2,2,2-trichloro-tert-butyloxycarbonyl), Fmoc (9-fluorenylmethyloxycarbonyl), 1-Adoc (1-Adamantyloxycarbonyl) and 2-Adoc (2-adamantyloxycarbonyl).

Hydroxyl Protecting Groups

Hydroxyl protecting groups are well known in the art, a large number of suitable groups are described on pages 16 to 366 of Wuts, P. G. M. and Greene, T. W., Protective Groups in Organic Synthesis, 4$^{th}$ Edition, Wiley-lnterscience, 2007, and in P. Kocienski, *Protective Groups,* 3rd Edition (2005) which are incorporated herein by reference.

Classes of particular interest include silyl ethers, methyl ethers, alkyl ethers, benzyl ethers, esters, benzoates, carbonates, and sulfonates.

Particularly preferred protecting groups include THP (tetrahydropyranyl ether).

"Drug", "drug substance", "active pharmaceutical ingredient", and the like, refer to a compound (e.g., compounds of Formula 1 and compounds specifically named above) that may be used for treating a subject in need of treatment.

"Excipient" refers to any substance that may influence the bioavailability of a drug, but is otherwise pharmacologically inactive.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Pharmaceutical composition" refers to the combination of one or more drug substances and one or more excipients.

The term "subject" as used herein refers to a human or non-human mammal. Examples of non-human mammals include livestock animals such as sheep, horses, cows, pigs, goats, rabbits and deer; and companion animals such as cats, dogs, rodents, and horses.

"Therapeutically effective amount" of a drug refers to the quantity of the drug or composition that is effective in treating a subject and thus producing the desired therapeutic, ameliorative, inhibitory or preventative effect. The therapeutically effective amount may depend on the weight and age of the subject and the route of administration, among other things.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating", as defined immediately above.

As used herein the term "comprising" means "including at least in part of" and is meant to be inclusive or open ended. When interpreting each statement in this specification that includes the term "comprising", features, elements and/or steps other than that or those prefaced by the term may also be present. Related terms such as "comprise" and "comprises" are to be interpreted in the same manner.

The present invention relates to a compound of formula (I):

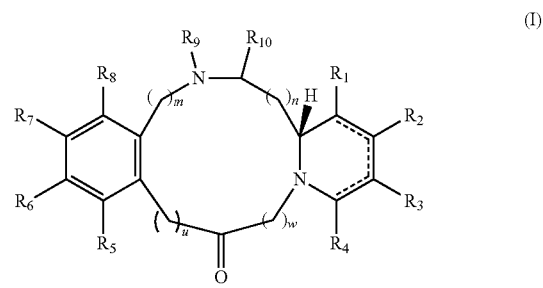

and salts or solvates thereof.

In some aspects, the compound of formula (I) is a compound with the following structure:

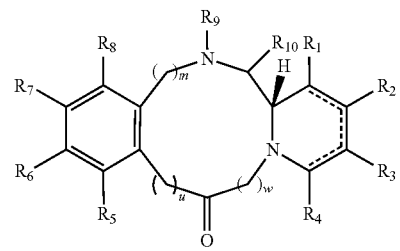

and salts or solvates thereof.

$R_4$

Suitably $R_4$ are independently selected from H, $C_{1-12}$ alkyl, $C_{2-12}$ alkenyl, OH, O—$C_{1-12}$ alkyl, $NH_2$, NHR, NRR', $CH_2$—$CO_2C_{1-12}$ alkyl, $CO_2H$, $CH_2$—$CO_2H$, $CO_2C_{1-12}$ alkyl, $COC_{1-12}$ alkyl and CN.

Suitably $R_4$ is selected from H, $C_{1-6}$ alkyl, $C_{2-12}$ alkenyl, OH, O—$C_{1-6}$ alkyl, $NH_2$, NH($C_{1-6}$ alkyl), $CO_2C_{1-6}$ alkyl, $CH_2$—$CO_2C_{1-6}$ alkyl, $CO_2H$ and $CH_2$—$CO_2H$.

More suitably $R_4$ is selected from H, $NH_2$, NH($C_{1-6}$ alkyl), $CO_2C_{1-6}$ alkyl, $CH_2$—$CO_2C_{1-6}$ alkyl, $CO_2H$ and $CH_2$—$CO_2H$.

$R_5$

Suitably $R_5$ is selected from H, R, OH, OR, $NH_2$, NHR, NRR', $CO_2H$, $CH_2$—$CO_2H$, $CO_2R$, $CH_2$—$CO_2R$ and halo.

Suitably $R_5$ is selected from H, $C_{1-12}$ alkyl, $C_{3-20}$ heteroaryl, $C_{4-32}$ heteroaralkyl, $C_{5-20}$ aryl groups, $C_{7-32}$ aralkenyl, OH, O—$C_{1-12}$ alkyl, $NH_2$, NHR, $CO_2H$, $CH_2$—$CO_2H$, $CO_2R$, $CH_2$—$CO_2R$ and halo.

More suitably $R_5$ is selected from H, $NH_2$, NH($C_{1-6}$ alkyl), $C_{1-6}$ alkyl, $C_{3-8}$ heteroaryl, $C_{6-12}$ aryl groups, O—$C_{1-6}$ alkyl, $CO_2H$, $CH_2$—$CO_2H$, $CO_2(C_{1-6}$ alkyl) and $CH_2$—$CO_2(C_{1-6}$ alkyl).

More suitably $R_5$ is selected from H, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl). More suitably, $R_5$ is H.

$R_6$

Suitably $R_6$ is selected from H, R, OH, OR, $NH_2$, NHR, NRR', $CO_2H$, $CH_2$—$CO_2H$, $CO_2R$, $CH_2$—$CO_2R$ and halo.

Suitably $R_6$ is selected from H, $C_{1-12}$ alkyl, OH, O—$C_{1-12}$ alkyl, $OCH_2Ph$, $NH_2$, NHR, $CO_2H$, $CH_2$—$CO_2H$, $CO_2R$, $CH_2$—$CO_2R$ and halo.

More suitably $R_6$ is selected from H, $C_{1-6}$ alkyl, OH, O—$C_{1-6}$ alkyl, $OCH_2Ph$, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

More suitably $R_6$ is selected from H, O—$C_{1-6}$ alkyl, $OCH_2Ph$, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl). More suitably, $R_5$ is selected from H, $C_{1-12}$ alkyl, O—$C_{1-12}$ alkyl, $OCH_2Ph$.

$R_8$

Suitably $R_8$ is selected from H, R, OH, OR, $NH_2$, NHR, NRR', $CO_2H$, $CH_2$—$CO_2H$, $CO_2R$, $CH_2$—$CO_2R'$ and halo.

Suitably $R_8$ is selected from H, $C_{1-12}$ alkyl, OH, O—$C_{1-12}$ alkyl, $NH_2$, NHR, $CO_2H$, $CH_2$—$CO_2H$, $CO_2R$, $CH_2$—$CO_2R$ and halo.

More suitably $R_8$ is selected from H, $C_{1-6}$ alkyl, O—$C_{1-6}$ alkyl, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

More suitably $R_8$ is selected from H, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl). More suitably $R_8$ is selected from H.

R and R'

Suitably R and R' are independently selected from optionally substituted $C_{1-8}$ alkyl, $C_{2-8}$ alkenyl, $C_{3-15}$ heterocyclyl, $C_{4-16}$ heterocyclalkyl, $C_{5-17}$ heterocyclalkenyl, $C_{3-10}$ heteroaryl, $C_{4-22}$ heteroaralkyl, $C_{5-23}$ heteroaralkenyl, $C_{5-16}$ aryl groups $C_{6-22}$ aralkyl and $C_{7-22}$ aralkenyl.

Suitably R and R' are independently selected from optionally substituted $C_{1-8}$ alkyl, $C_{2-8}$ alkenyl, $C_{3-12}$ heterocyclyl, $C_{3-10}$ heteroaryl, $C_{4-22}$ heteroaralkyl, $C_{6-14}$ aryl groups and $C_{6-22}$ aralkyl.

More suitably R and R' are independently selected from optionally substituted $C_{1-6}$ alkyl, $C_{2-6}$ alkenyl, $C_{3-11}$ heterocyclyl, $C_{3-8}$ heteroaryl, $C_{4-14}$ heteroaralkyl, $C_{6-12}$ aryl groups and $C_{6-18}$ aralkyl. More suitably, R and R' are independently selected from $C_{1-6}$ alkyl groups.

$R_1$, $R_2$, $R_3$ and $R_4$

In an embodiment (c) one of $R_1$, $R_2$ and $R_3$ has the formula:

—X-L-X'-D; or —$(CH_2)_f$—O—$R_{14}$.

wherein $R_{14}$ is selected from H and R; and f is 0 or 1.

Suitably $R_{14}$ is selected from H and $C_{1-12}$ alkyl; more suitably, $R_{14}$ is selected from H and $C_{1-6}$ alkyl.

Where $R_1$ has the formula —X-L-X-D the resulting compound may be represented by the following formula (C1):

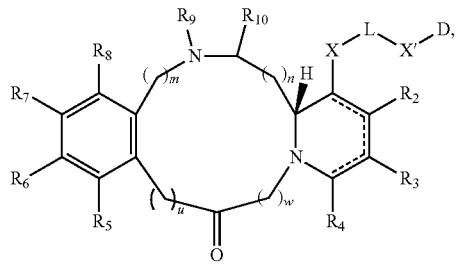

(C1)

or where $R_2$ has the formula —X-L-X-D by the following formula (C2):

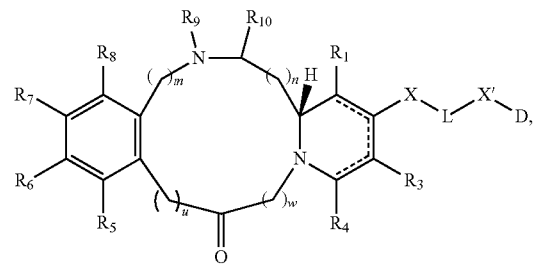

(C2)

or where $R_3$ has the formula —X-L-X-D by the following formula (C3):

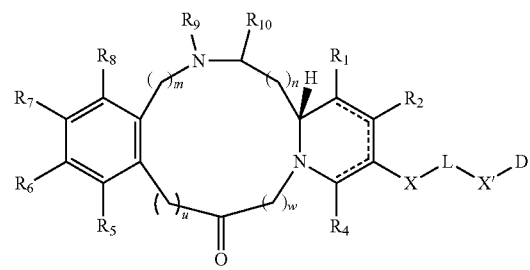

(C3)

and the remaining of $R_1$, $R_2$ and $R_3$ are independently selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2H$, $CO_2R$, COR, CN, ($C_{1-12}$ alkylene)-C(O)NR",R'" and ($C_{2-12}$ alkenylene)-C(O)NR'R" and halo;

and $R_7$ selected from H, R, OH, OR, $NH_2$, NHR, NRR', $CH_2$—OR, $CH_2$—$CO_2R$, $CH_2$—$CO_2H$, $CH_2$—$SO_2R$, O—$SO_2R$, $CO_2H$, $CO_2R$, COR, CN, ($C_{1-12}$ alkylene)-C(O)NR",R'" and ($C_{2-12}$ alkenylene)-C(O)NR'R" and halo.

In this embodiment (c), suitably the remaining of $R_1$, $R_2$ and $R_3$ are independently selected from H, R, OR, $NH_2$, NHR, $CH_2$—OR, =O, =CH—R, =$CH_2$, $CH_2$—$CO_2R$, $CO_2H$, $CO_2R$, COR, ($C_{1-12}$ alkylene)-C(O)NR",R'" and ($C_{2-12}$ alkenylene)-C(O)NR'R" and halo.

In this embodiment (c), suitably $R_7$ is selected from H, R, OH, OR $NH_2$, NHR, NRR', $CO_2H$, $CH_2$—$CO_2H$, $CO_2R$, $CH_2$—$CO_2R$ and halo. More suitably $R_7$ is selected from H, $C_{1-6}$ alkyl, OH, O—$C_{1-6}$ alkyl, $OCH_2Ph$ $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl). More suitably $R_7$ is selected from H, O—$C_{1-6}$ alkyl, $OCH_2Ph$, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

Suitably, in embodiment (c) m+n+u+w=0. Hence, suitably formulas (C1), (C2) and (C3) comprise a 6-7-6 ring system.

The possible options for the presence or absence of double bonds in the C-ring and for stereoisomers of the above compounds (C1), (C2) and (C3) are set out below as structures (IX) to (XXXXIV) in the suitable structures section.

In a further embodiment (d) $R_7$ has the formula: —X-L-X'-D; or —$(CH_2)_g$—O—$R_5$. wherein $R_{15}$ is selected from H and R; and g is 0 or 1.

Suitably, $R_{15}$ is selected from H and $C_{1-12}$ alkyl; more suitably, $R_{15}$ is selected from H and $C_{1-6}$ alkyl.

and where $R_7$ has the formula —X-L-X'-D, the resulting compound may be represented by the following formula (C3):

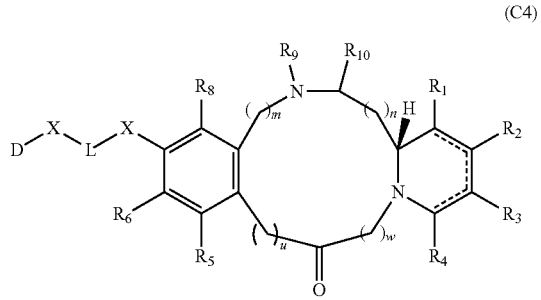

(C4)

and $R_1$, $R_2$ and $R_3$ are independently selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2H$, $CO_2R$, COR, CN, ($C_{1-12}$ alkylene)-C(O)NR''',R'' and ($C_{2-12}$ alkenylene)-C(O)NR'R'' and halo.

In this embodiment (d), suitably $R_1$, $R_2$ and $R_3$ are independently selected from H, R, OR, $NH_2$, NHR, $CH_2$—OR, =O, =CH—R, =$CH_2$, $CH_2$—$CO_2R$, $CO_2H$, $CO_2R$, COR, ($C_{1-12}$ alkylene)-C(O)NR'',R''' and ($C_{2-12}$ alkenylene)-C(O)NR'R'' and halo.

The possible options for the presence or absence of double bonds in the C-ring and for stereoisomers of the above compounds (C4) are set out below as structures (IX) to (XXXXIV) in the suitable structures section.

R'' and R'''

Suitably R'' and R''' are independently selected from H and optionally substituted $C_{1-8}$ alkyl. More suitably, R'' and R''' are independently selected from H and optionally substituted $C_{1-6}$ alkyl; more suitably, from H and methyl, ethyl, propyl and butyl.

X

Suitably X is selected from O, NR'', =CR'''—, CR''R'''O, C(=O), C(=O)NR'', NR''C(=O), O—C(O) and C(O)—O.

Suitably, X is selected from O, =CR'''—, C(=O)NR'' and NR''C(=O).

More suitably X is selected from O, =CH—, C(=O)NH and NHC(=O).

More suitably X is O.

X'

Suitably X, is selected from O, NR'', =CR'''—, CR''R'''O, C(=O), C(=O)NR'', NR''C(=O), O—C(O) and C(O)—O or is absent.

Suitably X' is selected from O, =CR'''—, C(=O)NR'' and NR''C(=O).

More suitably X is selected from O, =CH—, C(=O)NH and NHC(=O).

Suitably X is the same as X'.

More suitably X' is O.

L

Suitably, any of the peptide chain, alkylene chain, paraformaldehyde chain or polyethylene glycol chain is interrupted by one or more hetero-atoms (e.g., N, O and S) and/or one or more $C_{3-20}$ heteroaryl groups (e.g., pyrrolyl, pyrazolyl, pyrazolyl, 1,2,3-triazolyl, pyridinyl) and/or one or more $C_{5-20}$ aryl groups (e.g. phenyl). More suitably, the chains may be interrupted by from one to three hetero-atoms and/or from one to three $C_{3-20}$ heteroaryl groups and/or from one to three $C_{5-20}$ aryl groups.

Suitably L is selected from a peptide chain having from 2 to 5 amino acids, from 2 to 4 amino acids, from 2 to 3 amino acids; an alkylene chain containing from 1 to 11 carbon atoms, from 1 to 10 carbon atoms, from 1 to 9 carbon atoms, from 1 to 8 carbon atoms, from 1 to 7 carbon atoms, from 1 to 6 carbon atoms, from 1 to 5 carbon atoms, which may contain one or more carbon-carbon double or triple bonds; a paraformaldehyde chain —$(OCH_2)_{1-12}$—, —$(OCH_2)_{1-11}$—, —$(OCH_2)_{1-10}$—, —$(OCH_2)_{1-9}$—, —$(OCH_2)_{1-8}$—, —$(OCH_2)_{1-7}$—, —$(OCH_2)_{1-6}$—, —$(OCH_2)_{1-5}$—, —$(OCH_2)_{1-4}$—, —$(OCH_2)_{1-3}$-a polyethylene glycol chain-$(OCH_2CH_2)_{1-5}$—, chain —$(OCH_2CH_2)_{1-4}$—, chain —$(OCH_2CH_2)_{1-3}$—; which chain may be interrupted by one or more hetero-atoms and/or $C_{3-20}$ heteroaryl groups and/or $C_{5-20}$ aryl groups.

More suitably, L may be selected from an alkylene chain containing from 1 to 12 carbon atoms which may contain one or more carbon-carbon double or triple bonds. More suitably, L may be selected from CH=CH, $CH_2$, $CH_2CH_2CH_2$, $CH_2CH_2CH_2CH_2$ and $CH_2CH_2CH_2CH_2CH_2$.

D

Suitably D has the formula (II) or (III) and $R_{11}$ is selected from N-methylpyrrolylene, furanylene, thiophenylene, N-methylimidazolylene, oxazolylene, thiazolylene, indolylene, N-methylindolylene, benzofuranylene, benzothiophenylene, benzimidazolylene, N-methylbenzoimidazolylene, benzooxazolylene and benzothiazolylene.

In an embodiment, suitably D has the formula (II) or (III) and $R_{11}$ is selected from N-methylpyrrolylene, furanylene, thiophenylene, N-methylimidazolylene, oxazolylene and thiazolylene.

In an alternative embodiment, suitably D has the formula (II) or (III) and $R_{11}$ is selected from indolylene, N-methylindolylene, benzofuranylene, benzothiophenylene, benzimidazolylene, N-methylbenzoimidazolylene, benzooxazolylene and benzothiazolylene.

Suitably D has the formula (II) or (III) and $R_{12}$ is selected from N-methylpyrrolylene, furanylene, thiophenylene, N-methylimidazolylene, oxazolylene, thiazolylene, indolylene, N-methylindolylene, benzofuranylene, benzothiophenylene, benzimidazolylene, N-methylbenzoimidazolylene, benzooxazolylene and benzothiazolylene.

In an embodiment, suitably D has the formula (II) or (III) and $R_{12}$ is selected from N-methylpyrrolylene, furanylene, thiophenylene, N-methylimidazolylene, oxazolylene and thiazolylene.

In an alternative embodiment, suitably D has the formula (II) or (III) and $R_{12}$ is selected from indolylene, N-methylindolylene, benzofuranylene, benzothiophenylene, benzimidazolylene, N-methylbenzoimidazolylene, benzooxazolylene and benzothiazolylene.

Suitably D is selected from formula (D1):

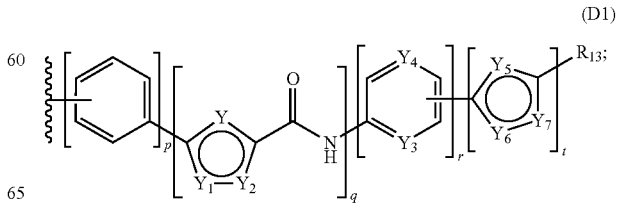

(D1)

(D2)

formula (D3):

(D3)

and formula (D4):

(D4)

wherein:
p is 0 or 1;
q is 1, 2, 3, 4, 5 or 6;
r is 0 or 1;
t is 0 or 1
$Y$, $Y_1$ and $Y_2$ are selected from CH, CH and N—$CH_3$; CH, N—$CH_3$ and CH; N, CH and N—$CH_3$; N, N—$CH_3$ and CH; CH, S and CH; CH, CH and S; N, S and CH; N, CH and S; N, O and CH; N, CH and O; CH, CH and O; CH O and CH; COH, N—$CH_3$ and CH; and COH, CH and N—$CH_3$;
$Y_3$ is N or CH;
$Y_4$ is N or CH; wherein at least one of $Y_3$ and $Y_4$ is CH.
$Y_5$, $Y_6$ and $Y_7$ are selected from CH, CH and N—$CH_3$; CH, N—$CH_3$ and CH; N, CH and N—$CH_3$; N, N—$CH_3$ and CH; CH, S and CH; CH, CH and S; N, S and CH; N, CH and S; N, O and CH; N, CH and O; CH, CH and O; CH O and CH; COH, N—$CH_3$ and CH; and COH, CH and N—$CH_3$;
$Y_8$ is selected from O, S, NH and N—$CH_3$;
$Y_9$ is selected from CH and N;
$Y_{10}$ is selected from O, S, NH and N—$CH_3$;
$Y_{11}$ is selected from CH and N;
$R_{13}$ is H, Z—R'', Z—$CO_2$R'', Z—C(=O)—NH—$(CH_2)_{1-6}$—NR''R''', and Z—C(=O)—NH—$(CH_2)_{1-6}$—C(=NH)NR''R''';
Z is absent or is selected from $C_{3-20}$ heteroaryl, $C_{1-6}$ alkyl substituted $C_{3-20}$ heteroaryl, —$(CH_2)_k$—$C_{3-20}$ heterocyclyl, and —O—$(CH_2)_k$—$C_{3-20}$ heterocyclyl group; and
k is 0, 1, 2, 3 or 4.

Hence, the heteroaryl rings containing Y, $Y_1$ and $Y_2$ and $Y_5$, $Y_6$ and $Y_7$ are independently selected from one of the following groups:

-continued lp;1p and

Hence, the heteroaryl rings containing $Y_8$ and $Y_9$, $Y_{10}$ and $Y_{11}$ are independently selected from one of the following groups:

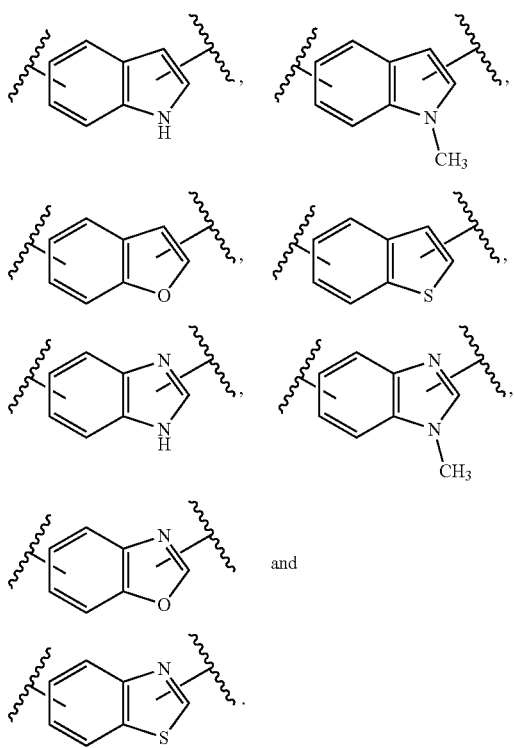

Suitably heteroaryl groups containing the $Y_8$ and $Y_9$ groups and those containing $Y_{10}$ and $Y_{11}$ groups are attached to the rest of the compound at the C-2 and C-5 positions as shown below:

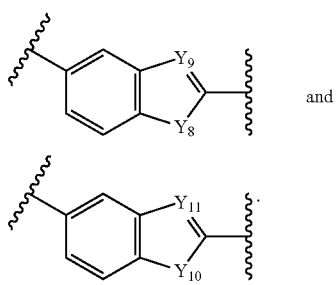

The aromatic ring containing $Y_3$ and $Y_4$ is a phenylene or pyridinylene group.

In an embodiment, suitably D is of formula (D1) or (D2) and p is 0, such that D may be represented by formula (D5) or (D6):

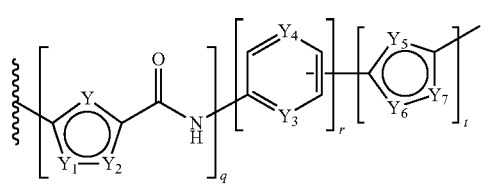

(D5)

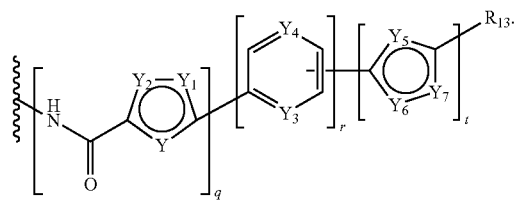

(D6)

Suitably, $Y_1$ and $Y_2$ are selected from CH, CH and N—$CH_3$; CH, N—$CH_3$ and CH; N, CH and N—$CH_3$; N, N—$CH_3$ and CH. Suitably Y, $Y_1$ and $Y_2$ are selected from CH, N—$CH_3$ and CH; and N, N—$CH_3$ and CH.

Suitably r is 1 and $Y_3$ and $Y_4$ are CH.

Suitably $Y_5$, $Y_6$ and $Y_7$ are selected from CH, CH and N—$CH_3$; CH, N—$CH_3$ and CH; N, CH and N—$CH_3$; N, N—$CH_3$ and CH. Suitably $Y_5$, $Y_6$ and $Y_7$ is CH, N—$CH_3$ and CH.

Suitably, $R_{13}$ is H, Z—R" and Z—$CO_2$R". Suitably, $R_{13}$ is H, Z—H, Z—$C_{1-6}$ alkyl, Z—$CO_2$H and Z—$CO_2C_{1-6}$ alkyl.

Suitably, Z is selected from $C_{3-20}$ heteroaryl and $C_{1-6}$ alkyl substituted $C_{3-20}$ heteroaryl; suitably, Z is selected from $C_{3-10}$ heteroaryl and $C_{1-6}$ alkyl substituted $C_{3-10}$ heteroaryl; suitably, Z is selected from $C_{3-9}$ heteroaryl and $C_{1-6}$ alkyl substituted $C_{3-9}$ heteroaryl.

More suitably, Z is a $C_{3-9}$ heteroaryl or a methyl substituted $C_{3-9}$ heteroaryl selected from benzofuranylene, benzothiophenylene, indolylene, N-methyl indolylene, N-methylbenzimidazolylene, benzoxazolylene and benzothiazolylene.

More suitably Z is absent and $R_{13}$ is $CO_2$R".

More suitably Z is absent and $R_{13}$ is $CO_2C_{1-6}$ alkyl.

More suitably D is formula (D7):

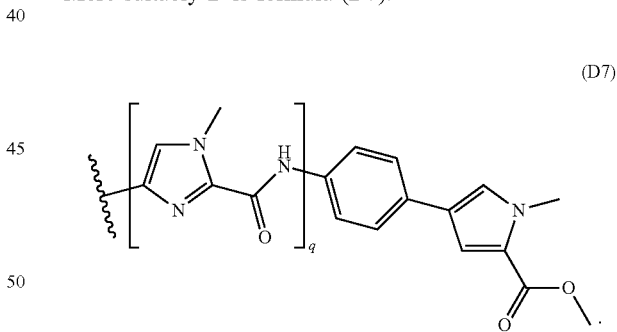

(D7)

In another embodiment, suitably D is of formula (D3) or (D4) and p is 0, such that D may be represented by formula (D8) or (D9):

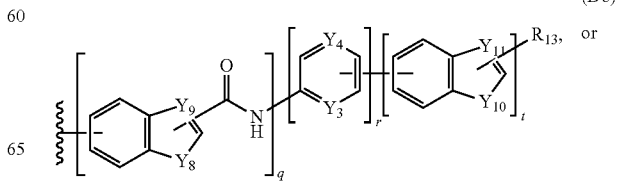

(D8) or

-continued

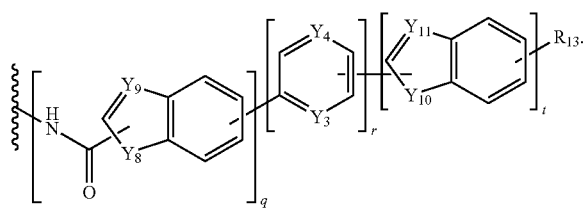
(D9)

Suitably $Y_8$ and $Y_9$ are selected from NH and CH; NH and N; N—CH$_3$ and CH; N—CH$_3$ and N; O and CH; O and N. Suitably $Y_8$ and $Y_9$ are N—CH$_3$ and CH.

Suitably $Y_{10}$ and $Y_{11}$ are selected from NH and CH; NH and N; N—CH$_3$ and CH; N—CH$_3$ and N; O and CH; and O and N. Suitably $Y_{10}$ and $Y_{11}$ are N—CH$_3$ and CH.

Suitably r is 1 and $Y_3$ and $Y_4$ are CH.

Suitably, $R_{13}$ is H, Z—R'' and Z—CO$_2$R''.

Suitably, $R_{13}$ is H, Z—H, Z—C$_{1-6}$ alkyl, Z—CO$_2$H and Z—CO$_2$C$_{1-6}$ alkyl.

Suitably, Z is selected from C$_{3-20}$ heteroaryl and C$_{1-6}$ alkyl substituted C$_{3-20}$ heteroaryl; suitably, Z is selected from C$_{3-10}$ heteroaryl and C$_{1-6}$ alkyl substituted C$_{3-10}$ heteroaryl; suitably, Z is selected from C$_{3-9}$ heteroaryl and C$_{1-6}$ alkyl substituted C$_{3-9}$ heteroaryl.

More suitably, Z is a C$_{3-9}$ heteroaryl or a methyl substituted C$_{3-9}$ heteroaryl selected from benzofuranylene, benzothiophenylene, indolylene, N-methyl indolylene, N-methylbenzimidazolylene, benzoxazolylene and benzothiazolylene.

More suitably Z is absent and $R_{13}$ is CO$_2$R''.

More suitably Z is absent and $R_{13}$ is CO$_2$C$_{1-6}$ alkyl.

In an embodiment, suitably D is of formula (D1) or (D2) and p is 0; r is 0; and t is 0; such that D may be represented by formula (D10) or (D11):

(D10)

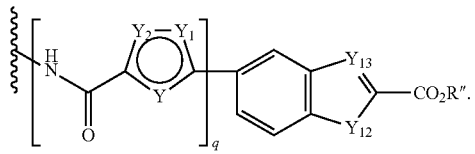
(D11)

Suitably Y, $Y_1$ and $Y_2$ are selected from CH, CH and N—CH$_3$; CH, N—CH$_3$ and CH; N, CH and N—CH$_3$; N, N—CH$_3$ and CH. Suitably Y, $Y_1$ and $Y_2$ are selected from CH, N—CH$_3$ and CH; and N, N—CH$_3$ and CH.

Suitably $Y_{12}$ is selected from O, S, NH and N—CH$_3$.

Suitably $Y_{13}$ is selected from CH and N;

Suitably, R'' is selected from H and C$_{1-6}$ alkyl.

m, n, u and w

In one aspect, m+n+u+w=1. This aspect includes compounds of formula (I) according to embodiments (a), (c) and (d).

More suitably, in a further aspect, m+n+u+w=0. This further aspect includes compounds of formula (I) according to embodiments (b) and (c). Suitably, in this further aspect, m+n+u+w=0 and the compound of formula (I) is a dimer according to embodiment (b). More suitably, in this further aspect, m+n+u+w=0 and the compound of formula (I) is a monomer according to embodiment (c).

Combination of Substituents

Suitably, at least 3 of $R_1$ to $R_8$ are H. Suitably, at least 4 of $R_1$ to $R_8$ are H. Suitably, at least 5 of $R_1$ to $R_8$ are H.

In one aspect, one of $R_1$ to $R_8$ is selected from NH$_2$, NH(C$_{1-6}$ alkyl), CO$_2$(C$_{1-6}$ alkyl), CH$_2$—CO$_2$(C$_{1-6}$ alkyl), CO$_2$H and CH$_2$—CO$_2$H; and at least 4 of the remaining of $R_1$ to $R_8$ are independently selected from H, C$_{1-6}$ alkyl and O—C$_{1-6}$ alkyl.

Suitable Structures

In one aspect, the compound of formula (I) has no double bonds in the C-ring and may be represented by the formula (IX):

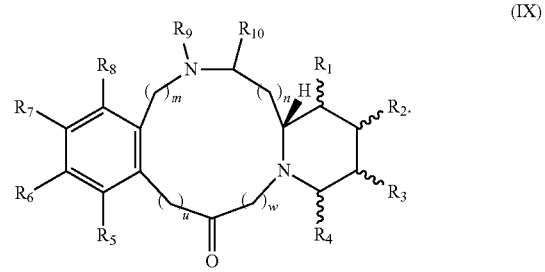
(IX)

Suitably, the compound of formula (IX) may be prepared with controlled stereochemistry and may be selected from:

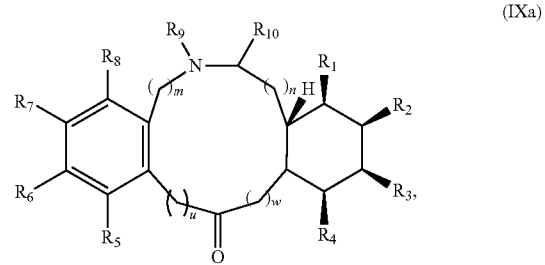
(IXa)

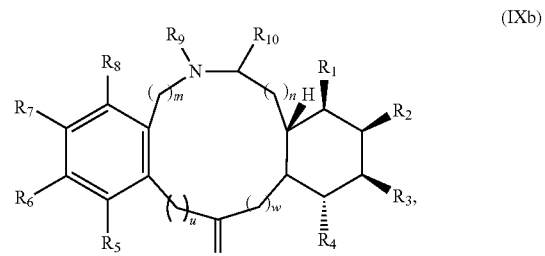
(IXb)

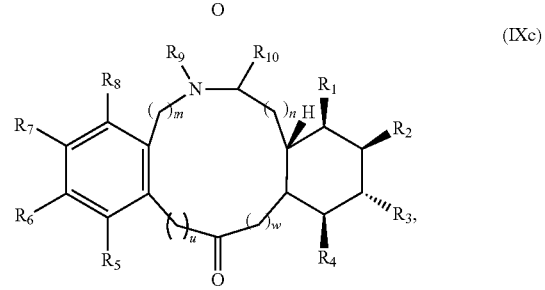
(IXc)

(IXd)
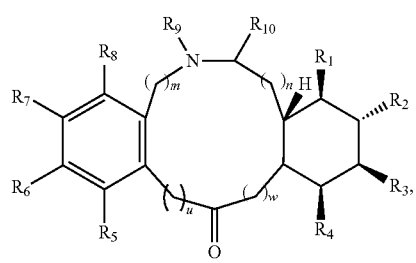
(IXe)
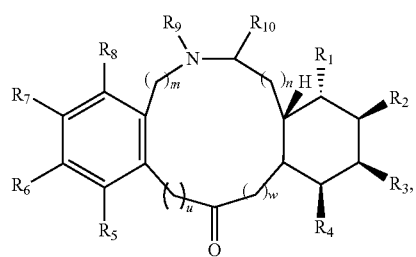
(IXf)
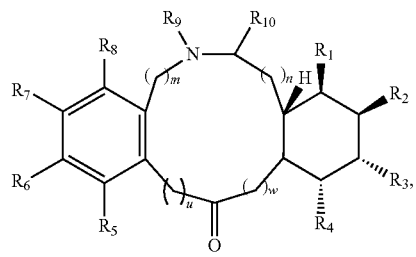
(IXg)
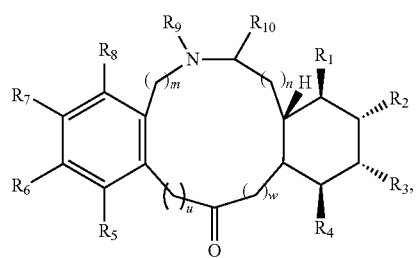
(IXh)
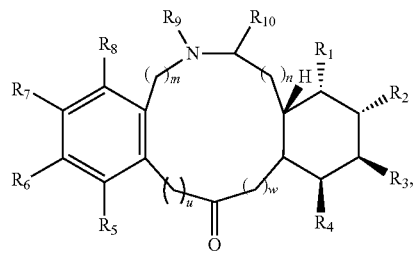
(IXi)
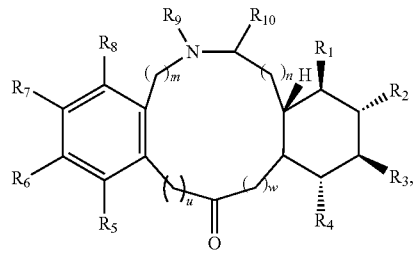
(IXj)
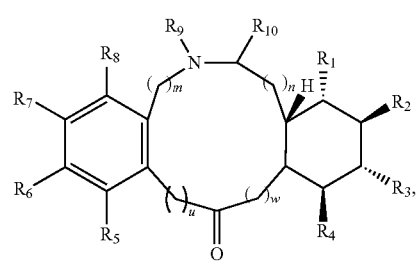
(IXk)
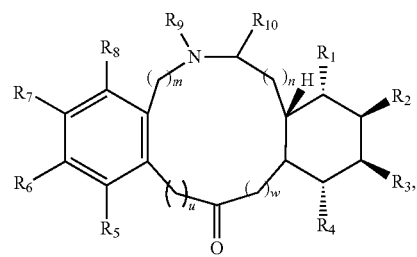
(IXl)
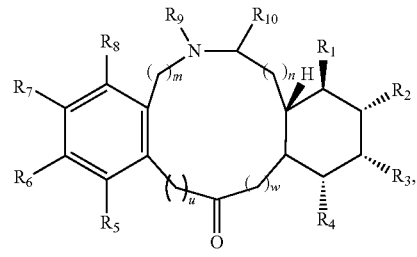
(IXm)
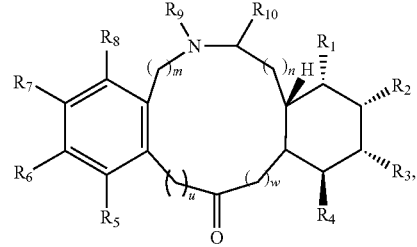
(IXn)
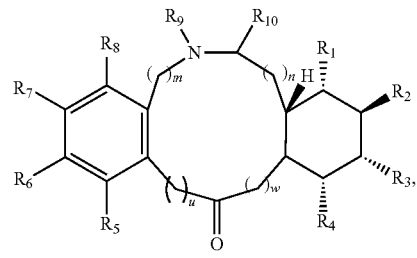
(IXo)
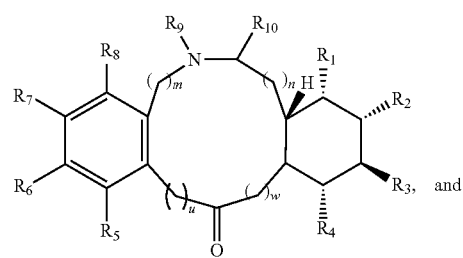
and

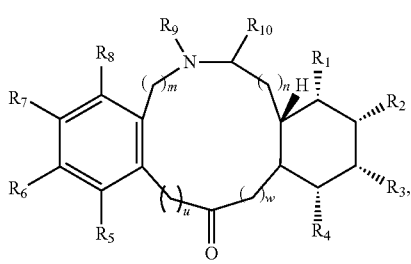
(IXp)

In one aspect, the compound of formula (I) has a double bond between $C_1$ and $C_2$ and may be represented by the formula (X):

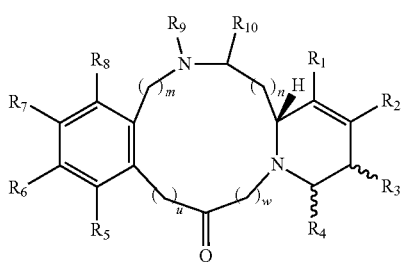
(X)

Suitably, the compound of formula (X) may be prepared with controlled stereochemistry and may be selected from:

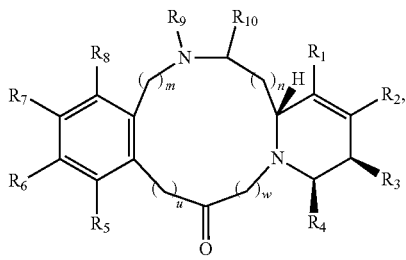
(Xa)

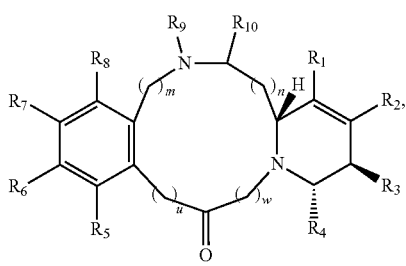
(Xb)

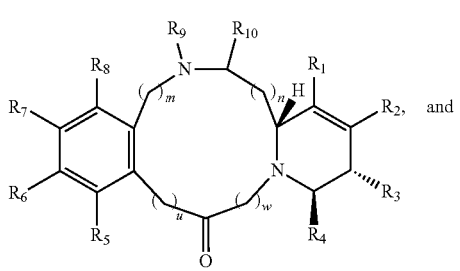
(Xc)

and

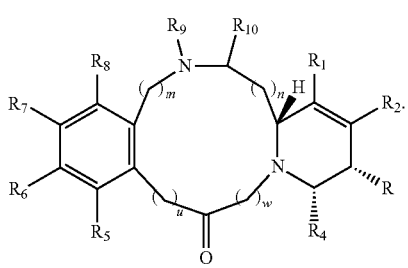
(Xd)

In another aspect, the compound of formula (I) has a double bond between $C_2$ and $C_3$ and may be represented by the formula (XI):

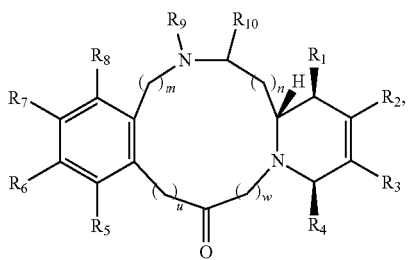
(XI)

Suitably, the compound of formula (XI) may be prepared with controlled stereochemistry and may be selected from:

(XIa)

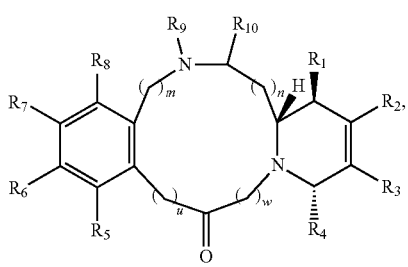
(XIb)

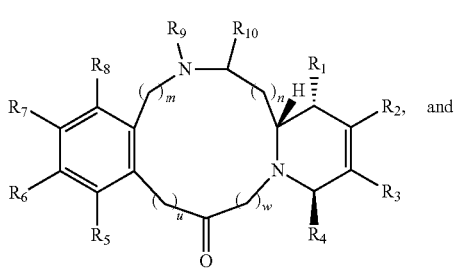
(XIc)

and

-continued

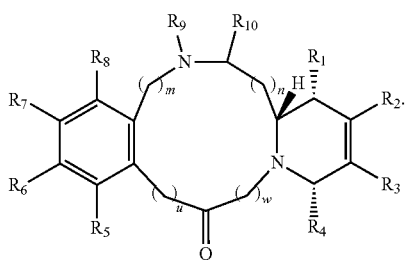
(XId)

In another aspect, the compound of formula (I) has a double bond between C3 and C4 and may be represented by the formula (XII):

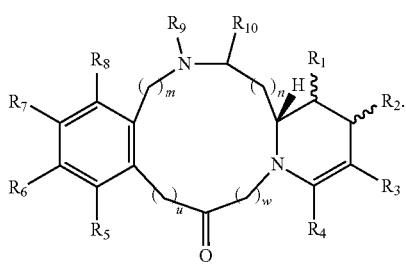
(XII)

Suitably, the compound of formula (XII) may be prepared with controlled stereochemistry and may be selected from:

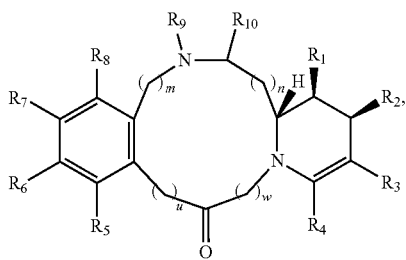
(XIIa)

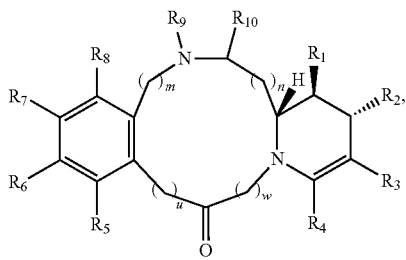
(XIIb)

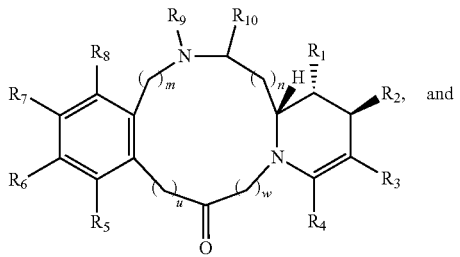
(XIIc)

-continued

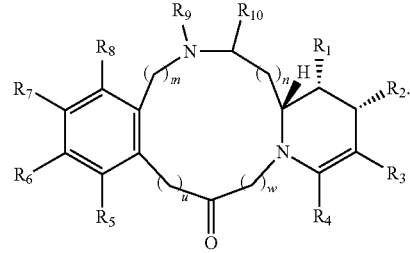
(XIId)

In another aspect, the compound of formula (I) has a double bond between C1 and C2 and another double bond between C3 and C4 and may be represented by the formula (XIII):

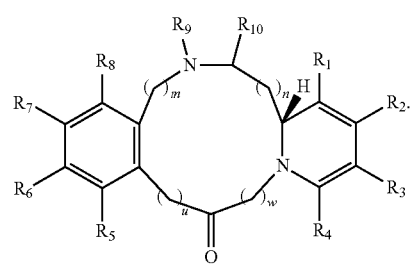
(XIII)

Suitably the compound of formula (I) has $R_3=R_4=R_5=R_8=H$ and may be represented by the following structure (XIV):

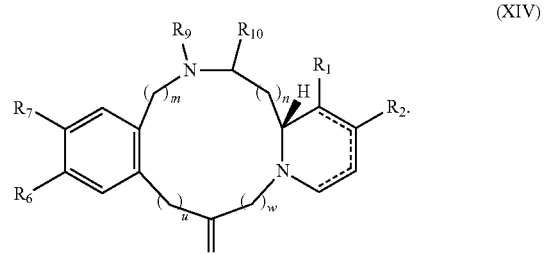
(XIV)

In an embodiment according to (b) or (c), more suitably the compound is a compound of formula (I) wherein $m=n=u=w=0$ and may be represented by formula (IV):

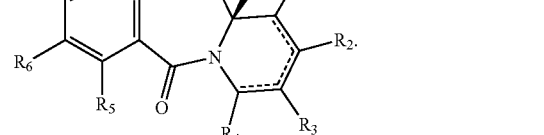
(IV)

More suitably, the compound of formula (IV) above has no double bonds in the C-ring and may be represented by the formula (XV):

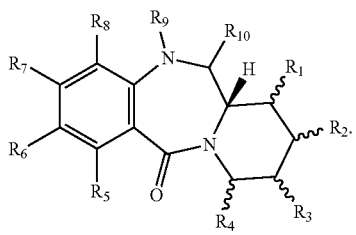

(XV)

The possible options for stereoisomers of the C-ring for the compound of formula (XV) are set out above as structures (IXa)-(IXp) in the suitable structures section.

More suitably, the compound of formula (IV) above may have a double bond between C1 and C2 and may be represented by the formula (XVI):

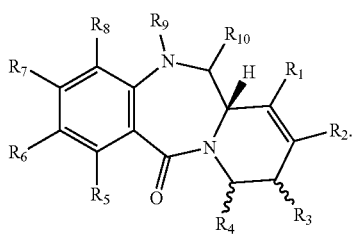

(XVI)

The possible options for stereoisomers of the C-ring for the compound of formula (XVI) are set out above as structures (Xa)-(Xd) in the suitable structures section.

More suitably, the compound of formula (IV) above may have a double bond between C2 and C3 and may be represented by the formula (XVII):

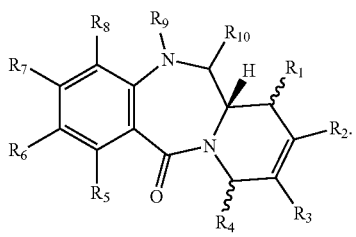

(XVII)

The possible options for stereoisomers of the C-ring for the compound of formula (XVII) are set out above as structures (XIa)-(XId) in the suitable structures section.

More suitably, the compound of formula (IV) above may have a double bond between C3 and C4 and may be represented by the formula (XVIII):

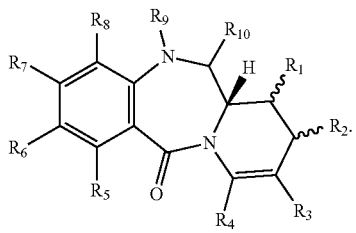

(XVIII)

The possible options for stereoisomers of the C-ring for the compound of formula (XVIII) are set out above as structures (XIIa)-(XIId) in the suitable structures section.

More suitably, the compound of formula (IV) above may have a double bond between C1 and C2 and another double bond between C3 and C4 and may be represented by the formula (XIX):

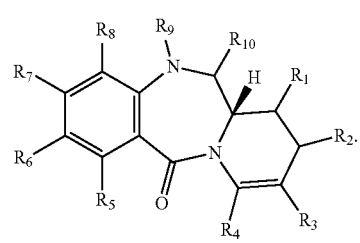

(XIX)

Most suitably the compound of formula (IV) has $R_3=R_4=R_5=R_8=H$ and may be represented by the following structure (XX):

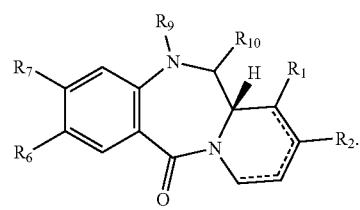

(XX)

In an embodiment according to (a), (c) or (d), suitably the compound is a compound of formula (I) wherein $m=u=w=0$ and $n=1$ and wherein the compound is represented by formula (V):

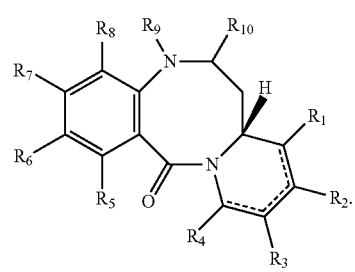

(V)

More suitably, the compound of formula (V) above has no double bonds in the C-ring and may be represented by the formula (XXI):

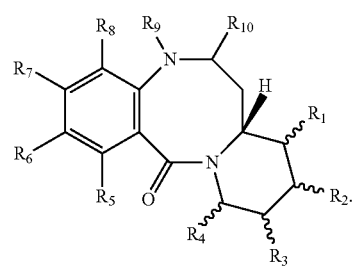

(XXI)

The possible options for stereoisomers of the C-ring for the compound of formula (XXI) are set out above as structures (IXa)-(IXp) in the suitable structures section.

Suitably the compound of formula (V) above may have a double bond between C1 and C2 and may be represented by the formula (XXII):

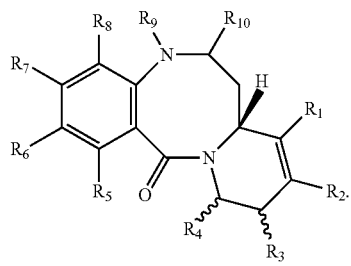

(XXII)

The possible options for stereoisomers of the C-ring for the compound of formula (XXII) are set out above as structures (Xa)-(Xd) in the suitable structures section.

Suitably the compound of formula (V) above may have a double bond between C2 and C3 and may be represented by the formula (XXIII):

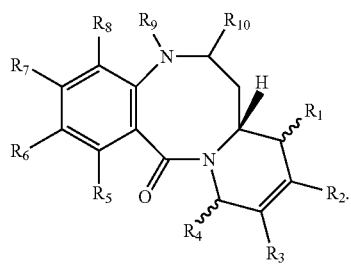

(XXIII)

The possible options for stereoisomers of the C-ring for the compound of formula (XXIII) are set out above as structures (XIa)-XId in the suitable structures section.

Suitably the compound of formula (V) above may have a double bond between C3 and C4 and may be represented by the formula (XXIV):

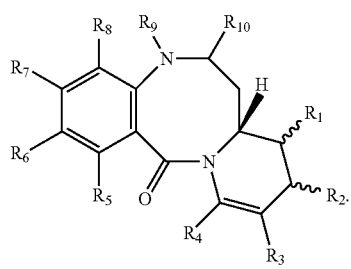

(XXIV)

The possible options for stereoisomers of the C-ring for the compound of formula (XXIV) are set out above as structures (XIIa)-(XIId) in the suitable structures section.

Suitably the compound of formula (V) above may have a double bond between C1 and C2 and another double bond between C3 and C4 and may be represented by the (XXV):

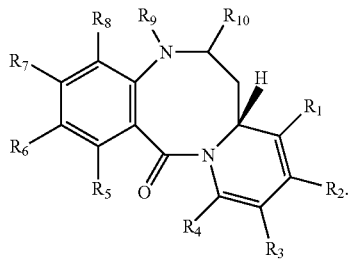

(XXV)

More suitably the compound of formula (V) has $R_3=R_4=R_5=R_8=H$ and may be represented by the following structure (XXVI):

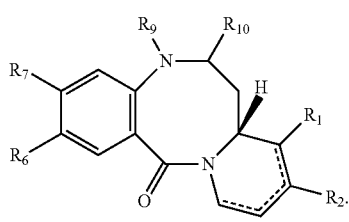

(XXVI)

In an embodiment according to (a), (c) or (d), suitably the compound is a compound of formula (I) wherein n=u=w=0 and m=1 and wherein the compound is represented by formula (VI):

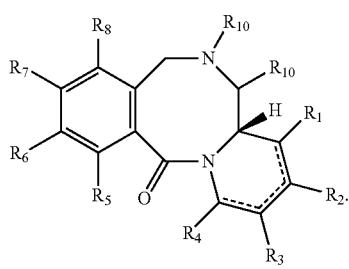

(VI)

More suitably, the compound of formula (VI) above has no double bonds in the C-ring and may be represented by the formula (XXVII):

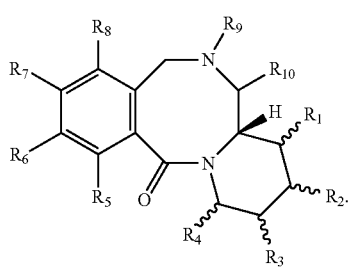

(XXVII)

The possible options for stereoisomers of the C-ring for the compound of formula (XXVII) are set out above as structures (IXa)-(IXp) in the suitable structures section.

Suitably, the compound of formula (VI) above may have a double bond between C1 and C2 and may be represented by the formula (XXVIII):

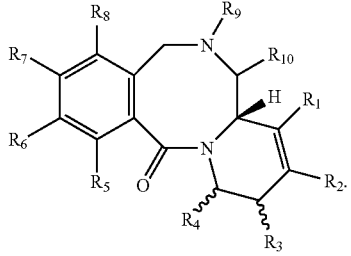

(XXVIII)

The possible options for stereoisomers of the C-ring for the compound of formula (XXVIII) are set out above as structures (Xa)-(Xd) in the suitable structures section.

Suitably, the compound of formula (VI) above may have a double bond between C2 and C3 and may be represented by the formula (XXIX):

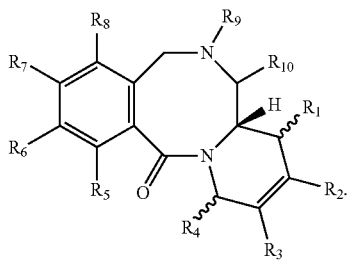

(XXIX)

The possible options for stereoisomers of the C-ring for the compound of formula (XXIX) are set out above as structures (XIa)-(XId) in the suitable structures section.

Suitably, the compound of formula (VI) above may have a double bond between C3 and C4 and may be represented by the formula (XXX):

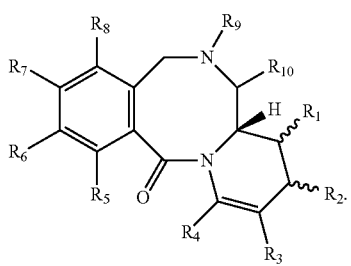

(XXX)

The possible options for stereoisomers of the C-ring for the compound of formula (XXX) are set out above as structures (XIIa)-(XIId) in the suitable structures section.

Suitably, the compound of formula (VI) above may have a double bond between C1 and C2 and another double bond between C3 and C4 and may be represented by the formula (XXXI):

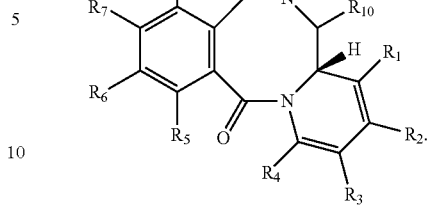

(XXXI)

More suitably the compound of formula (VI) has $R_3=R_4=R_5=R_8=H$ and may be represented by the following structure (XXXII):

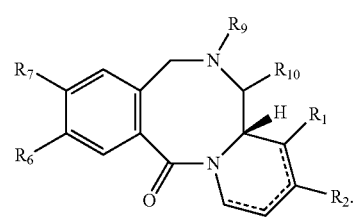

(XXXII)

In an embodiment according to (a), (c) or (d), suitably the compound is a compound of formula (I) wherein $m=n=w=0$ and $u=1$ and wherein the compound is represented by formula (VII):

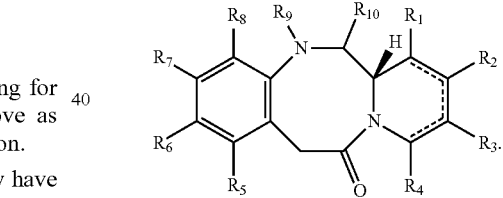

(VII)

More suitably, the compound of formula (VII) above has no double bonds in the C-ring and may be represented by the formula (XXXIII):

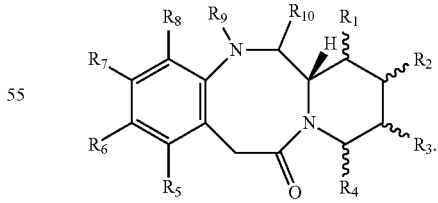

(XXXIII)

The possible options for stereoisomers of the C-ring for the compound of formula (XXXIII) are set out above as structures (IXa)-(IXp) in the suitable structures section.

Suitably, the compound of formula (VII) above may have a double bond between C1 and C2 and may be represented by the formula (XXXIV):

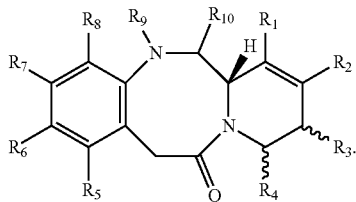

(XXXIV)

The possible options for stereoisomers of the C-ring for the compound of formula (XXXIV) are set out above as structures (Xa)-(Xd) in the suitable structures section.

Suitably, the compound of formula (VII) above may have a double bond between C2 and C3 and may be represented by the formula (XXXV):

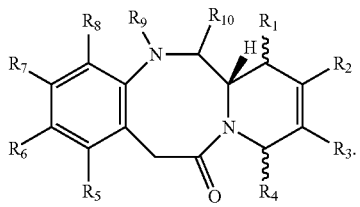

(XXXV)

The possible options for stereoisomers of the C-ring for the compound of formula (XXXV) are set out above as structures (XIa)-(XId) in the suitable structures section.

Suitably, the compound of formula (VII) above may have a double bond between C3 and C4 and may be represented by the formula (XXXVI):

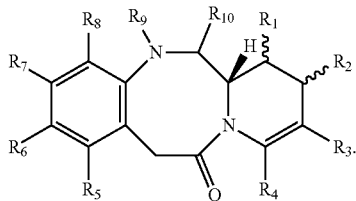

(XXXVI)

The possible options for stereoisomers of the C-ring for the compound of formula (XXXVI) are set out above as structures (XIIa)-(XIId) in the suitable structures section.

Suitably, the compound of formula (VII) above may have a double bond between C1 and C2 and another double bond between C3 and C4 and may be represented by the formula (XXXVII):

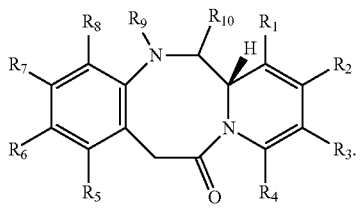

(XXXVII)

More suitably the compound of formula (VII) has $R_3=R_4=R_5=R_8=H$ and may be represented by the following structure (XXXVIII):

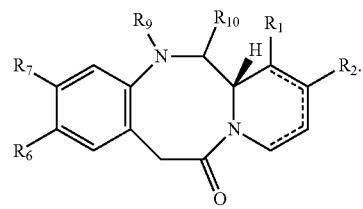

(XXXVIII)

In an embodiment according to (a), (c) or (d), suitably the compound is a compound of formula (I) wherein $m=n=u=0$ and $w=1$ and wherein the compound is represented by formula (VIII):

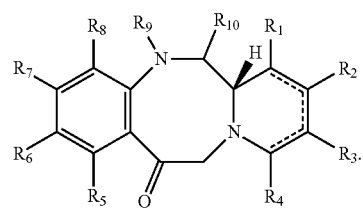

(VIII)

More suitably, the compound of formula (VIII) above has no double bonds in the C-ring and may be represented by the formula (XXXIX):

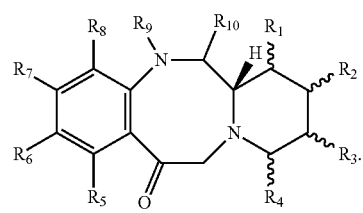

(XXXIX)

The possible options for stereoisomers of the C-ring for the compound of formula (XXXIX) are set out above as structures (IXa)-(IXp) in the suitable structures section.

Suitably, the compound of formula (VIII) above may have a double bond between C1 and C2 and may be represented by the formula (XXXX):

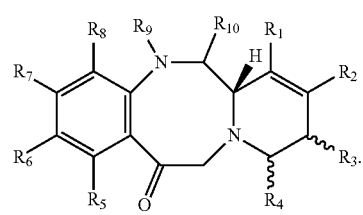

(XXXX)

The possible options for stereoisomers of the C-ring for the compound of formula (XXXX) are set out above as structures (Xa)-(Xd) in the suitable structures section.

Suitably, the compound of formula (VIII) above may have a double bond between C2 and C3 and may be represented by the formula (XXXXI):

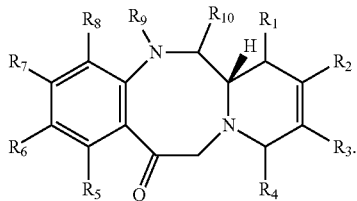

(XXXXI)

The possible options for stereoisomers of the C-ring for the compound of formula (XXXXI) are set out above as structures (XIa)-(XId) in the suitable structures section.

Suitably, the compound of formula (VIII) above may have a double bond between C3 and C4 and may be represented by the formula (XXXXII):

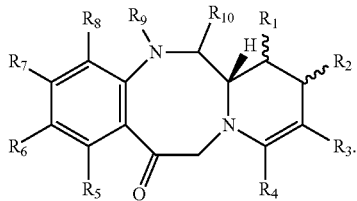

(XXXXII)

The possible options for stereoisomers of the C-ring for the compound of formula (XXXXII) are set out above as structures (XIIa)-(XIId) in the suitable structures section.

Suitably, the compound of formula (VIII) above may have a double bond between C1 and C2 and another double bond between C3 and C4 and may be represented by the (XXXXIII):

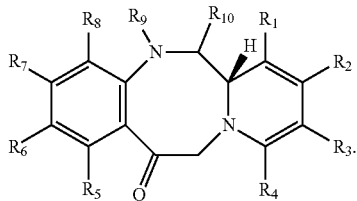

(XXXXIII)

More suitably the compound of formula (VIII) has $R_3=R_4=R_5=R_8=H$ and may be represented by the following structure (XXXXIV):

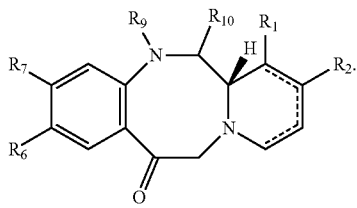

(XXXXIV)

Further Embodiments

In a further embodiment, the compound of formula (I) has the following structure:

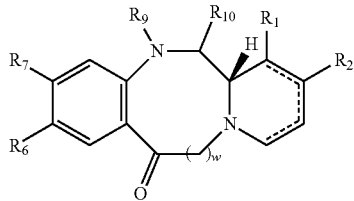

and salts or solvates thereof, wherein:

the dotted lines indicates the optional presence of a double bond between one or more of C1 and C2, C2 and C3, and C3 and C4;

$R_6$ is selected from H, $C_{1-12}$ alkyl, $C_{2-12}$ alkenyl, OH, O—$C_{1-12}$ alkyl, $OCH_2Ph$, $NH_2$, $NH(C_{1-12}$ alkyl), =O, =CH—$C_{1-12}$ alkyl, =$CH_2$, $CO_2H$, C(O)—O—$C_{1-12}$ alkyl;

and either:
(i) $R_9$ and $R_{10}$ together form a double bond;
(ii) $R_9$ is H and $R_{10}$ is OH; or
(iii) $R_9$ is H and $R_{10}$ is O—$C_{1-6}$ alkyl;

wherein w may be 0 or 1; and (a) the compound is a dimer with each monomer being the same or different and being of formula (I) where one of $R_1$, $R_2$ and $R_7$ of the first monomer and one of $R'_1$, $R'_2$ and $R'_7$ of the second monomer form together a bridge having the formula —X-L-X'— linking the monomers and w=1;

and the remaining of $R_1$ and $R_2$ of the first monomer and the remaining of $R'_1$, and $R'_2$ of the second monomer that do not form the bridge are independently selected from H, $C_{1-12}$ alkyl, $C_{2-12}$ alkenyl, OH, O—$C_{1-12}$ alkyl, $NH_2$, $NH(C_{1-12}$ alkyl), =O, =CH—$C_{1-12}$ alkyl, =$CH_2$, $CO_2H$ and C(O)—O—$C_{1-12}$ alkyl;

and the remaining of $R_7$ of the first monomer and $R'_7$ of the second monomer that do not form the bridge are independently selected from H, $C_{1-12}$ alkyl, $C_{2-12}$ alkenyl, OH, O—$C_{1-12}$ alkyl, $OCH_2Ph$, $NH_2$, $NH(C_{1-12}$ alkyl), $CO_2H$ and C(O)—O—$C_{1-12}$ alkyl;

or (b) the compound is a dimer with each monomer being the same or different and being of formula (I) where one of $R_1$ and $R_2$ of the first monomer and one of $R'_1$ and $R'_2$ of the second monomer form together a bridge having the formula —X-L-X'— linking the monomers and w=0;

and the remaining of $R_1$, and $R_2$ of the first monomer and the remaining of $R'_1$ and $R'_2$ of the second monomer that do not form the bridge are independently selected from H, $C_{1-12}$ alkyl, $C_{2-12}$ alkenyl, OH, O—$C_{1-12}$ alkyl, $NH_2$, $NH(C_{1-12}$ alkyl), =O, =CH—$C_{1-12}$ alkyl, =$CH_2$, $CO_2H$ and C(O)—O—$C_{1-12}$ alkyl;

and that $R_7$ of the first monomer and $R'_7$ of the second monomer are independently selected from H, $C_{1-12}$ alkyl, $C_{2-12}$ alkenyl, OH, O—$C_{1-12}$ alkyl, $OCH_2Ph$, $NH_2$, $NH(C_{1-12}$ alkyl), $CO_2H$ and C(O)—O—$C_{1-12}$ alkyl;

or (c) one of $R_1$ and $R_2$ has the formula:
—X-L-X'-D;

or

—$(CH_2)_f$—O—$R_{14}$;

wherein R$_{14}$ is selected from H and C$_{1-12}$ alkyl; f is 0 or 1;
and w is 0 or 1;
and the remaining of R$_1$ and R$_2$ is selected from H, C$_{1-12}$ alkyl, C$_{2-12}$ alkenyl, OH, O—C$_{1-12}$ alkyl, NH$_2$, NH(C$_{1-12}$ alkyl), =O, =CH—C$_{1-12}$ alkyl, =CH$_2$, CO$_2$H and C(O)—O—C$_{1-12}$ alkyl;
and R$_7$ is selected from H, C$_{1-12}$ alkyl, C$_{2-12}$ alkenyl, OH, O—C$_{1-12}$ alkyl, OCH$_2$Ph, NH$_2$, NH(C$_{1-12}$ alkyl), CO$_2$H and C(O)—O—C$_{1-12}$ alkyl;
or
(d) R$_7$ has the formula:
—X-L-X'-D;
or —(CH$_2$)$_g$—O—R$_5$;
wherein R$_{15}$ is selected from H and C$_{1-12}$ alkyl; g is 0 or 1;
and m+n+u+w=1;

formula (D2):

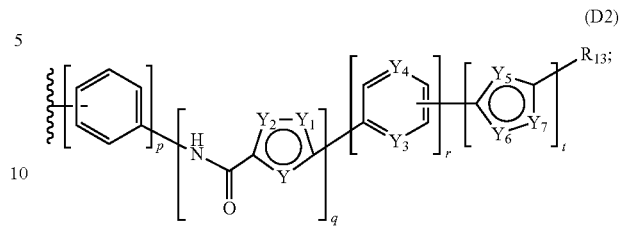

formula (D3):

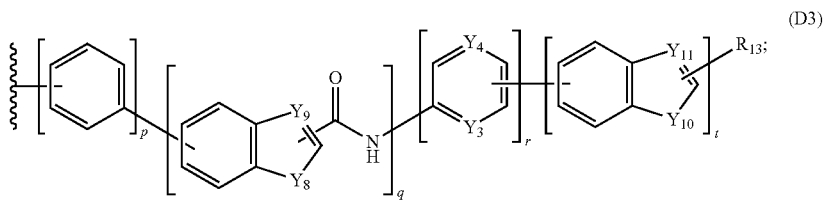

and formula (D4):

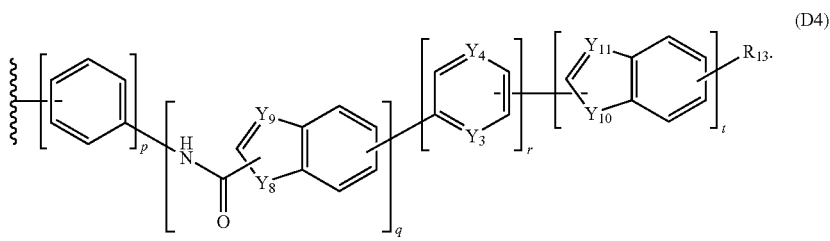

and R$_1$ and R$_2$ are independently selected from H, C$_{1-12}$ alkyl, C$_{2-12}$ alkenyl, OH, O—C$_{1-12}$ alkyl, NH$_2$, NH(C$_{1-12}$ alkyl), =O, =CH—C$_{1-12}$ alkyl, =CH$_2$, CO$_2$H and C(O)—O—C$_{1-12}$ alkyl;
wherein:
X is selected from O, =CH—, C(=O)NH and NHC(=O);
L is selected from a peptide chain having from 2 to 6 amino acids, an alkylene chain containing from 1 to 12 carbon atoms which may contain one or more carbon-carbon double or triple bonds, —(OCH$_2$)$_{1-12}$—, and —OCH$_2$CH$_2$)$_{1-6}$—;
X' is selected from O, =CH—, C(=O)NH and NHC(=O) or is absent; and
D is selected from formula (D1):

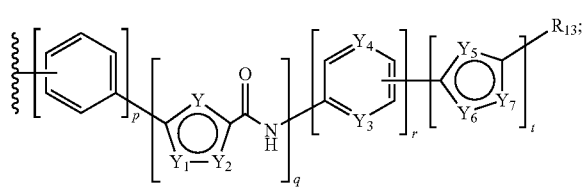

p is 0 or 1;
q is 1, 2, 3, 4, 5 or 6;
r is 0 or 1;
t is 0 or 1;
Y, Y$_1$ and Y$_2$ are selected from CH, CH and N—CH$_3$; CH, N—CH$_3$ and CH; N, CH and N—CH$_3$; N, N—CH$_3$ and CH; CH, S and CH; CH, CH and S; N, S and CH; N, CH and S; N, O and CH; N, CH and O; CH, CH and O; CH O and CH; COH, N—CH$_3$ and CH; and COH, CH and N—CH$_3$;
Y$_3$ is N or CH;
Y$_4$ is N or CH; wherein at least one of Y$_3$ and Y$_4$ is CH.
Y$_5$, Y$_6$ and Y$_7$ are selected from CH, CH and N—CH$_3$; CH, N—CH$_3$ and CH; N, CH and N—CH$_3$; N, N—CH$_3$ and CH; CH, S and CH; CH, CH and S; N, S and CH; N, CH and S; N, O and CH; N, CH and O; CH, CH and O; CH O and CH; COH, N—CH$_3$ and CH; and COH, CH and N—CH$_3$;
Y$_8$ is selected from O, S, NH and N—CH$_3$;
Y$_9$ is selected from CH and N;
Y$_{10}$ is selected from O, S, NH and N—CH$_3$;
Y$_{11}$ is selected from CH and N;
R$_{13}$ is H, Z—R", Z—CO$_2$R", Z—C(=O)—NH—(CH$_2$)$_{1-6}$—NR"R''', and Z—C(=O)—NH—(CH$_2$)$_{1-6}$—C(=NH)NR"R''';

Z is absent or is selected from or is selected from benzofuranylene, benzothiophenylene, indolylene, N-methyl indolylene, N-methylbenzimidazolylene, benzoxazolylene and benzothiazolylene;

k is 0, 1, 2, 3 or 4; and each R" and R'" is independently selected from H, and $C_{1-12}$ alkyl.

More suitably, in the above further embodiment w=0.

In a further embodiment, the compound of formula (I) has the following structure:

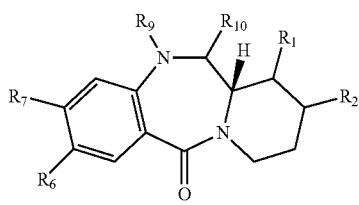

or is a dimer with the following structure:

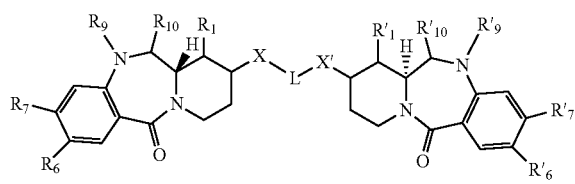

and salts or solvates thereof, wherein:

$R_1$ and $R'_1$ are independently selected from H, $C_{1-12}$ alkyl, $C_{2-12}$ alkenyl, OH, O—$C_{1-12}$ alkyl, $NH_2$, $NH(C_{1-12}$ alkyl), =O, =CH—$C_{1-12}$ alkyl, =$CH_2$, $CO_2H$ and C(O)—O—$C_{1-12}$ alkyl;

$R_6$, $R_7$, $R'_6$, and $R'_7$ are independently selected from H, $C_{1-12}$ alkyl, O—$C_{1-12}$ alkyl, $OCH_2Ph$;

and either:
(i) $R_9$ and $R_{10}$ together form a double bond, and $R'_9$ and $R'_{10}$ together form a double bond;
(ii) $R_9$ is H and $R_{10}$ is OH, and $R'_9$ is H and $R'_{10}$ is OH; or
(iii) $R_9$ is H and $R_{10}$ is $OR^A$ and $R^A$ is $C_{1-6}$ alkyl, and $R'_9$ is H and $R'_{10}$ is O—$C_{1-6}$ alkyl;

wherein:

$R_2$ has the formula:

—X-L-X'-D;

or

—$(CH_2)_f$—O—$R_{14}$;

$R_{14}$ is selected from H and $C_{1-12}$ alkyl; f is 0 or 1;

X is selected from O, =CH—, C(=O)NH and NHC(=O);

L is selected from a peptide chain having from 2 to 5 amino acids; an alkylene chain containing from 1 to 11 carbon atoms which may contain one or more carbon-carbon double or triple bonds; —$(OCH_2)_{1-12}$— and —$(OCH_2CH_2)_{1-5}$—;

X' is selected O, =CH—, C(=O)NH and NHC(=O) or is absent;

D is:

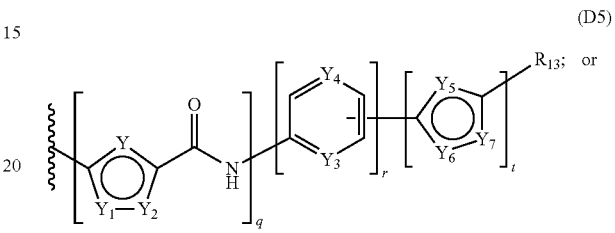

(D5)

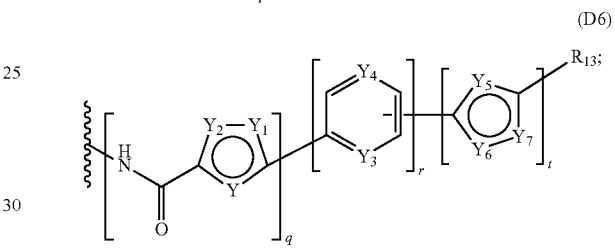

(D6)

q is 1, 2, 3, 4, 5 or 6;

r is 0 or 1;

t is 0 or 1

Y, $Y_1$ and $Y_2$ are selected from CH, CH and N—$CH_3$; CH, N—$CH_3$ and CH; N, CH and N—$CH_3$; N, N—$CH_3$ and CH;

$Y_3$ is N or CH;

$Y_4$ is N or CH; wherein at least one of $Y_3$ and $Y_4$ is CH;

$Y_5$, $Y_6$ and $Y_7$ are selected from CH, CH and N—$CH_3$; CH, N—$CH_3$ and CH; N, CH and N—$CH_3$; N, N—$CH_3$ and CH;

$R_{13}$ is H, Z—H, Z—$C_{1-6}$ alkyl, Z—$CO_2H$ and Z—$CO_2C_{1-6}$ alkyl; and

Z is absent or is selected from benzofuranylene, benzothiophenylene, indolylene, N-methyl indolylene, N-methylbenzimidazolylene, benzoxazolylene and benzothiazolylene.

Monomeric Compounds

In an embodiment according to (c), suitably the compound of formula (I) is:

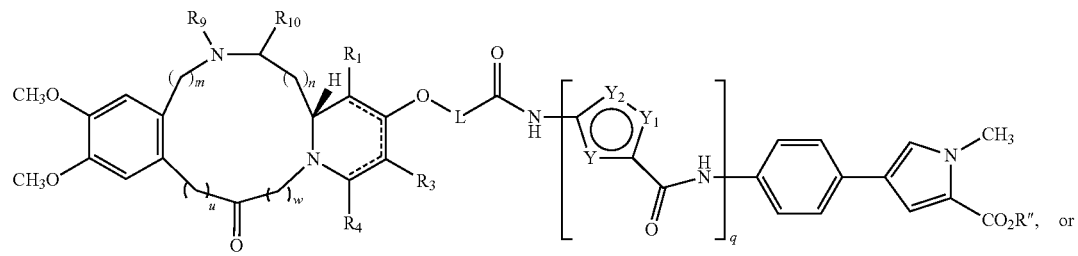

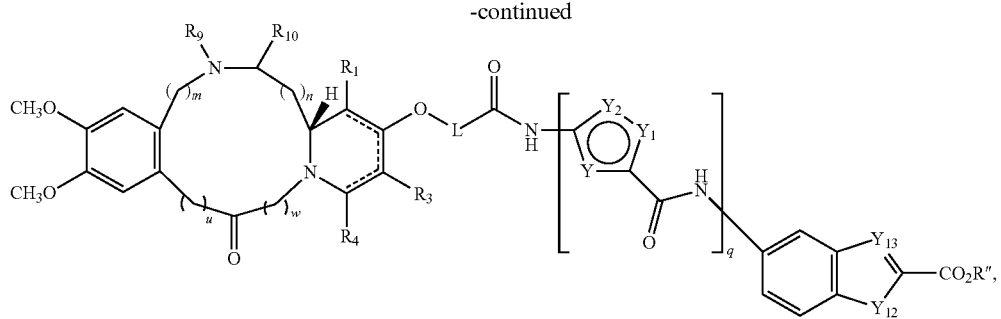

wherein q is selected from 1, 2, 3, 4, 5 or 6, L is an alkylene chain containing from 1 to 12 carbon atoms; Y, $Y_1$ and $Y_2$ are CH, N—$CH_3$ and CH; or are N, N—$CH_3$ and CH respectively; $Y_{12}$ is selected from O, S, NH and N—$CH_3$; $Y_{13}$ is selected from CH and N; and R" is selected from H and $C_{1-6}$ alkyl.

In an embodiment according to (c), suitably the compound of formula (I) is:

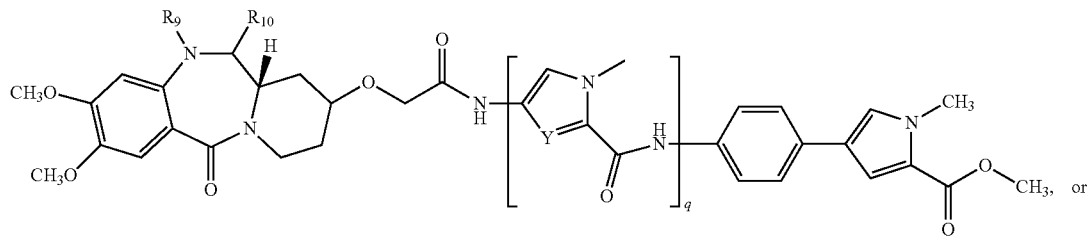

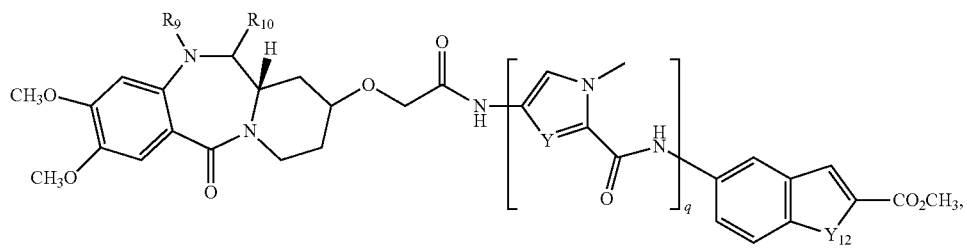

wherein q is selected from 1, 2, 3, 4, 5 or 6, and Y is selected from CH and N; and $Y_{12}$ is selected from S and O.

In an embodiment according to (d), suitably the compound of formula (I) is:

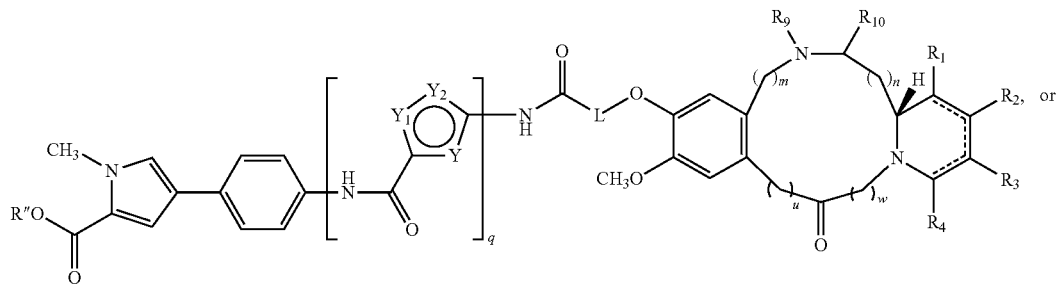

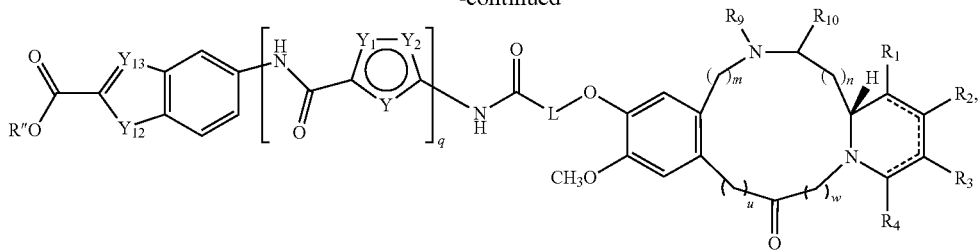

wherein q is selected from 1, 2, 3, 4, 5 or 6; L is an alkylene chain containing from 1 to 12 carbon atoms; Y, $Y_1$ and $Y_2$ are CH, N—$CH_3$ and CH; or are N, N—$CH_3$ and CH respectively; $Y_{12}$ is selected from O, S, NH and N—$CH_3$; $Y_{13}$ is selected from CH and N; and R" is selected from H and $C_{1-6}$ alkyl.

In an embodiment according to (d), suitably the compound of formula (I) is:

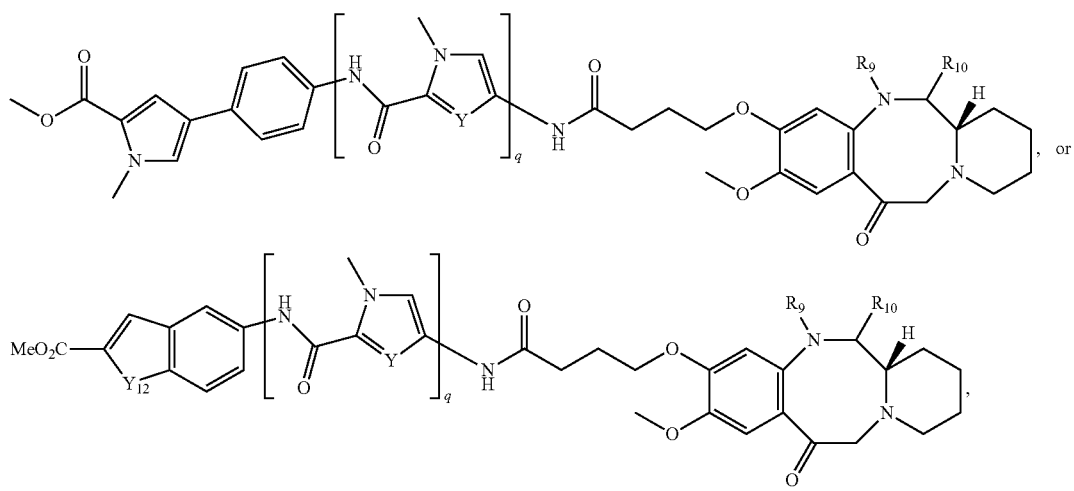

wherein q is selected from 1, 2, 3, 4, 5 or 6, and Y is selected from CH and N; and $Y_{12}$ is selected from S and O.

Dimer

In an embodiment (a) the compound is a dimer with each monomer being the same or different and being of formula (I) where one of $R_1$, $R_2$, $R_3$ and $R_7$ of the first monomer and $R'_1$, $R'_2$, $R'_3$ and $R'_7$ of the second monomer form together a bridge having the formula —X-L-X'— linking the monomers and m+n+u+w=1.

More suitably is embodiment (b) wherein the compound is a dimer with each monomer being the same or different and being of formula (I) where one of $R_1$, $R_2$ and $R_3$ of the first monomer and one of $R'_1$, $R'_2$, and $R'_3$ of the second monomer form together a bridge having the formula —X-L-X'— linking the monomers and m=n=u=w=0.

In embodiments (a) or (b), where a dimer is formed from two monomers of formula (I) and the $R_1$ group of the first monomer and the $R'_1$ of the second monomer form together a bridge having the formula —X-L-X'— linking the monomers, the resulting dimer may be represented by the following formula (A1):

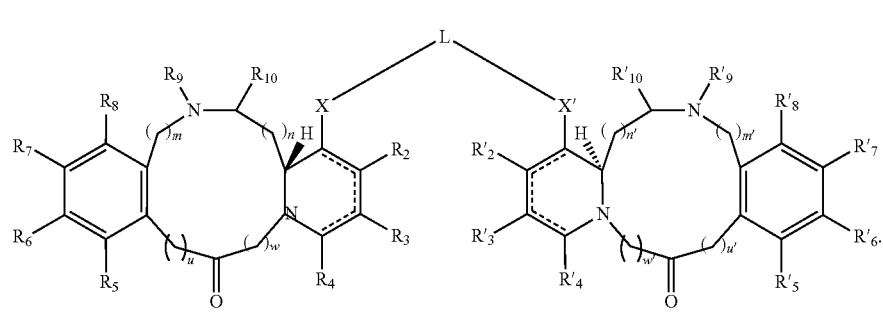

In embodiments (a) or (b), where a dimer is formed from two monomers of formula (I) and the $R_1$ group of the first monomer and the $R'_2$ of the second monomer form together a bridge having the formula —X-L-X'— linking the monomers, the resulting dimer may be represented by the following formula (A2):

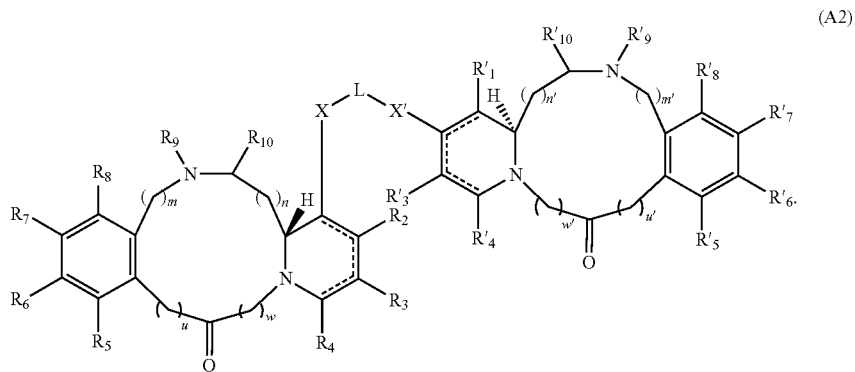

(A2)

In embodiments (a) or (b), where a dimer is formed from two monomers of formula (I) and the $R_1$ group of the first monomer and the $R'_3$ of the second monomer form together a bridge having the formula —X-L-X'— linking the monomers, the resulting dimer may be represented by the following formula (A3):

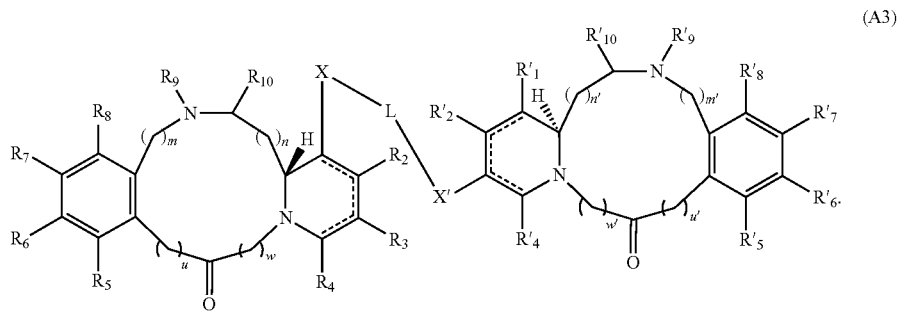

(A3)

In embodiment (a), where a dimer is formed from two monomers of formula (I) and the $R_1$ group of the first monomer and the $R'_7$ of the second monomer form together a bridge having the formula —X-L-X'— linking the monomers, the resulting dimer may be represented by the following formula (A4):

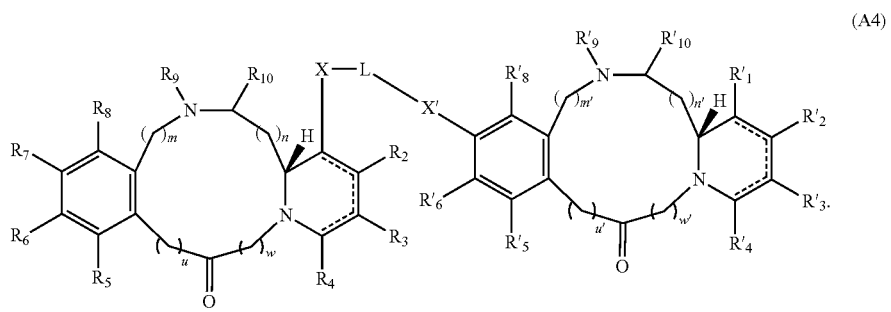

(A4)

In embodiments (a) or (b), where a dimer is formed from two monomers of formula (I) and the R₂ group of the first monomer and the R'₁ of the second monomer form together a bridge having the formula —X-L-X'— linking the monomers, the resulting dimer may be represented by the following formula (A5):

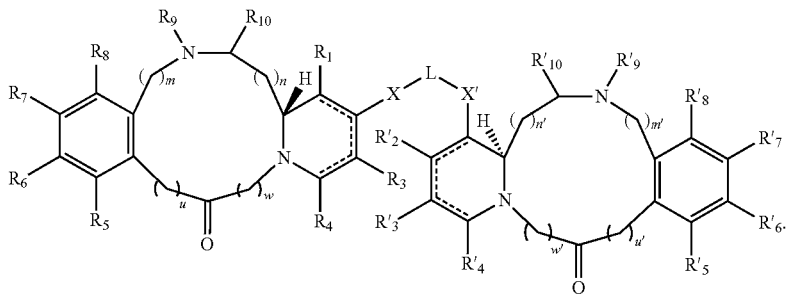
(A5)

In embodiments (a) or (b), where a dimer is formed from two monomers of formula (I) and the R₂ group of the first monomer and the R'₂ of the second monomer form together a bridge having the formula —X-L-X'— linking the monomers, the resulting dimer may be represented by the following formula (A6):

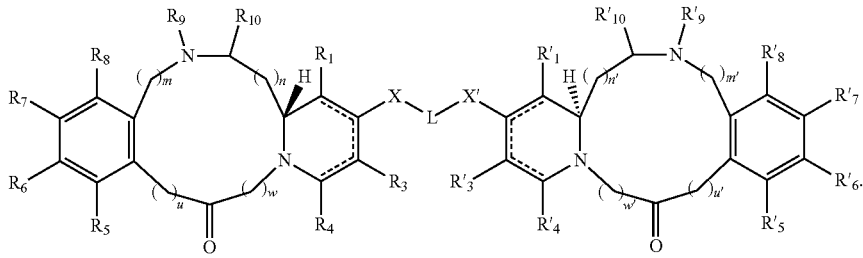
(A6)

In embodiments (a) or (b), where a dimer is formed from two monomers of formula (I) and the R₂ group of the first monomer and the R'₃ of the second monomer form together a bridge having the formula —X-L-X'— linking the monomers, the resulting dimer may be represented by the following formula (A7):

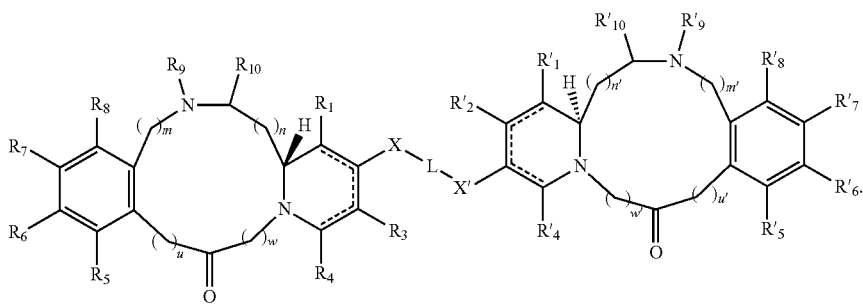
(A7)

In embodiment (a), where a dimer is formed from two monomers of formula (I) and the R₂ group of the first monomer and the R'₇ of the second monomer form together a bridge having the formula —X-L-X'— linking the monomers, the resulting dimer may be represented by the following formula (A8):

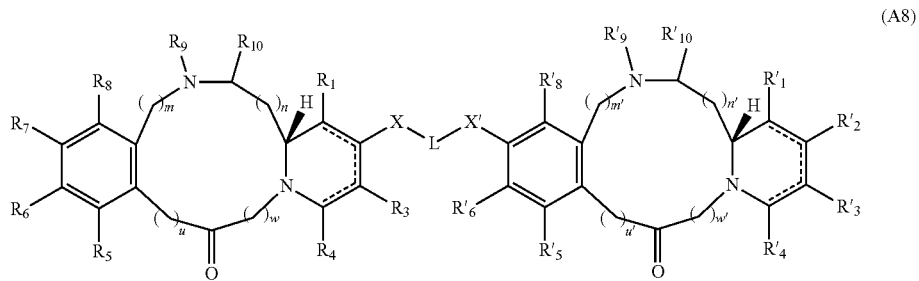

(A8)

In embodiments (a) or (b), where a dimer is formed from two monomers of formula (I) and the R₃ group of the first monomer and the R'₁ of the second monomer form together a bridge having the formula —X-L-X'— linking the monomers, the resulting dimer may be represented by the following formula (A9):

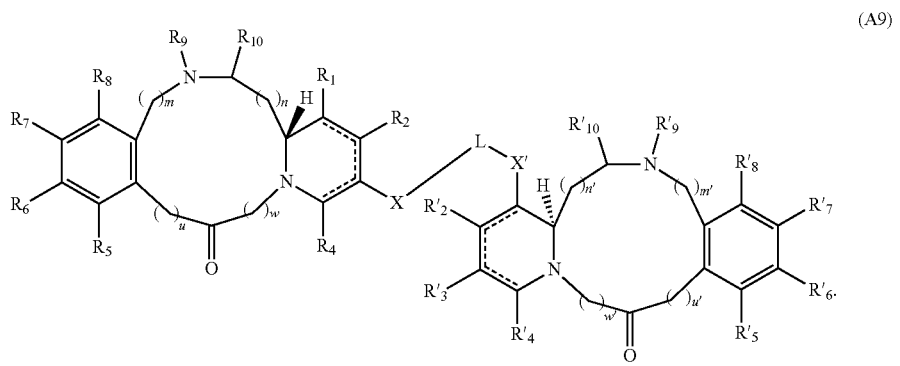

(A9)

In embodiments (a) or (b), where a dimer is formed from two monomers of formula (I) and the R₃ group of the first monomer and the R'₂ of the second monomer form together a bridge having the formula —X-L-X'— linking the monomers, the resulting dimer may be represented by the following formula (A10):

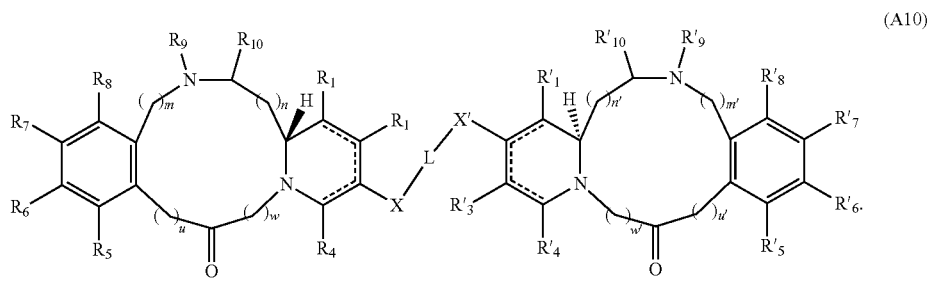

(A10)

In embodiments (a) or (b), where a dimer is formed from two monomers of formula (I) and the R₃ group of the first monomer and the R'₃ of the second monomer form together a bridge having the formula —X-L-X'— linking the monomers, the resulting dimer may be represented by the following formula (A11):

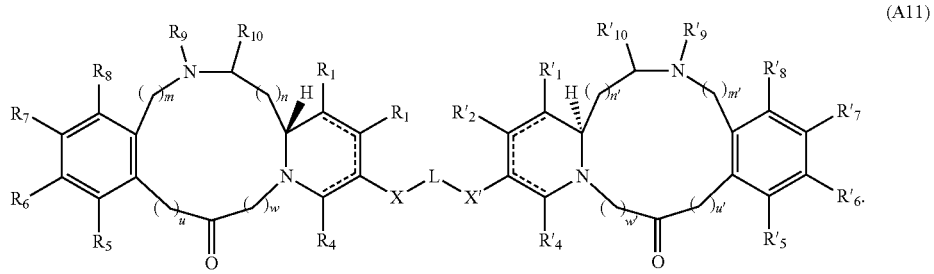

(A11)

In embodiment (a), where a dimer is formed from two monomers of formula (I) and the $R_3$ group of the first monomer and the $R'_7$ of the second monomer form together a bridge having the formula —X-L-X'— linking the monomers, the resulting dimer may be represented by the following formula (A12):

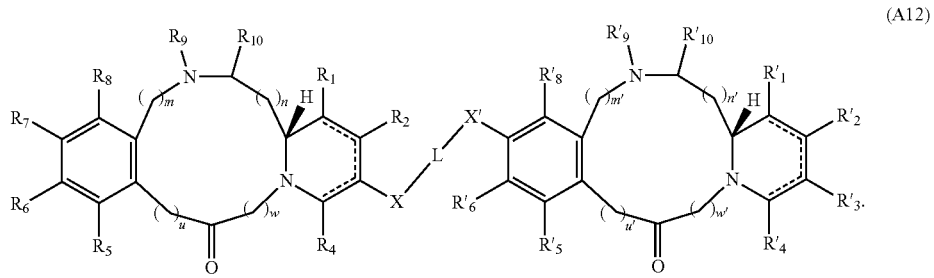

(A12)

In embodiment (a), where a dimer is formed from two monomers of formula (I) and the $R_7$ group of the first monomer and the $R'_1$ of the second monomer form together a bridge having the formula —X-L-X'— linking the monomers, the resulting dimer may be represented by the following formula (A13):

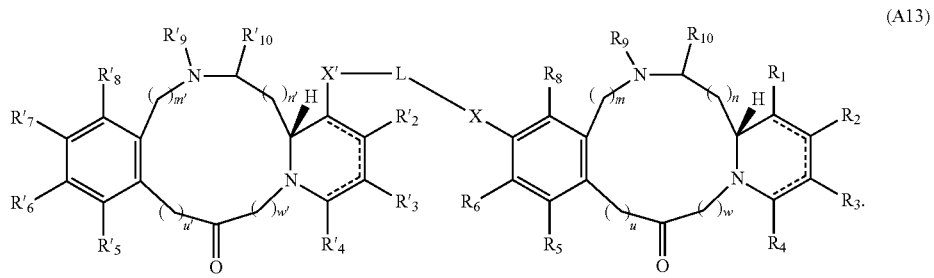

(A13)

In embodiment (a), where a dimer is formed from two monomers of formula (I) and the $R_7$ group of the first monomer and the $R'_2$ of the second monomer form together a bridge having the formula —X-L-X'— linking the monomers, the resulting dimer may be represented by the following formula (A14):

(A14)

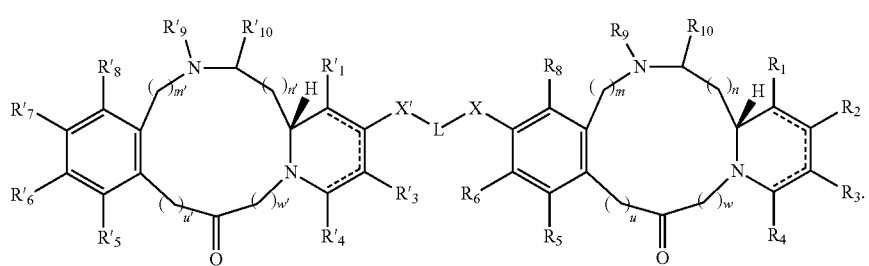

In embodiment (a), where a dimer is formed from two monomers of formula (I) and the $R_7$ group of the first monomer and the $R'_3$ of the second monomer form together a bridge having the formula —X-L-X'— linking the monomers, the resulting dimer may be represented by the following formula (A15):

(A15)

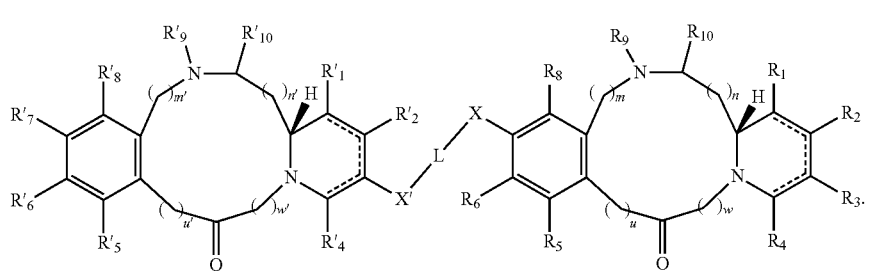

In embodiment (a), where a dimer is formed from two monomers of formula (I) and the $R_7$ group of the first monomer and the $R'_7$ of the second monomer form together a bridge having the formula —X-L-X'— linking the monomers, the resulting dimer may be represented by the following formula (A16):

(A16)

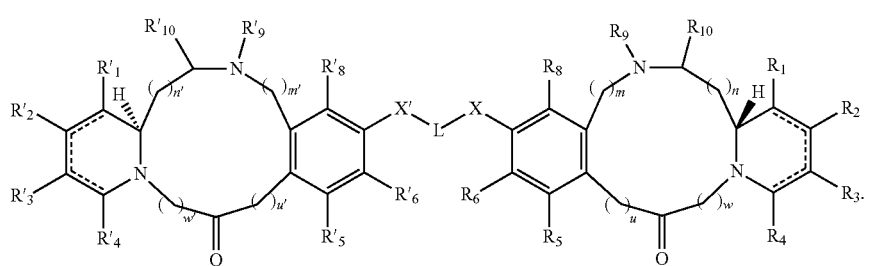

The possible options for the presence or absence of double bonds in the C-ring and for stereoisomers of each monomer that make up the dimers (A1) to (A16) are set out above in the suitable structures section.

Wherein for each of formulas (A1), (A2), (A3), (A4), (A5), (A6), (A7), (A8), (A9), (A10), (A11), (A12), (A13), (A14), (A15) and (A16) the groups m', n', u', w', $R'_4$, $R'_5$, $R'_6$, $R'_8$, $R'_9$ and $R'_{10}$ are independently selected from groups with the same meanings as for m, n, u, w, $R_4$, $R_5$, $R_6$, $R_8$, $R_9$ and $R_{10}$ respectively, and L is as described above.

For each of formulas (A5), (A6), (A7), (A8), (A9), (A10), (A11), (A12), (A13), (A14), (A15) and (A16) the remaining substituent $R_1$ is selected from H, R, OH, OR, $NH_2$, NHR, NRR', $CH_2$—OR, =O, =CH—R, =$CH_2$, $CH_2$—$CO_2$R, $CH_2$—$CO_2$H, $CH_2$—$SO_2$R, O—$SO_2$R, $CO_2$H, $CO_2$R, COR, CN, ($C_{1-12}$ alkylene)-C(O)NR",R'" and ($C_{2-12}$ alkenylene)-C(O)NR'R" and halo. Suitably the remaining substituent $R_1$ is selected from H, R, OR, $NH_2$, NHR, NRR', $CH_2$—OR, =O, =CH—R, =$CH_2$, $CH_2$—$CO_2$R, $CO_2$H, $CO_2$R, COR, ($C_{1-12}$ alkylene)-C(O)NR",R'" and ($C_{2-12}$ alkenylene)-C(O)NR'R" and halo.

For each of formulas (A2), (A3), (A4), (A6), (A7), (A8), (A10), (A11), (A12), (A14), (A15) and (A16) the remaining substituent $R'_1$ is selected from H, R, OH, OR, $NH_2$, NHR, NRR', $CH_2$—OR, =O, =CH—R, =$CH_2$, $CH_2$—$CO_2$R, $CH_2$—$CO_2$H, $CH_2$—$SO_2$R, O—$SO_2$R, $CO_2$H, $CO_2$R, COR, CN, ($C_{1-12}$ alkylene)-C(O)NR",R'" and ($C_{2-12}$ alkenylene)-C(O)NR'R" and halo. Suitably the remaining substituent $R'_1$ is selected from H, R, OR, $NH_2$, NHR, NRR', $CH_2$—OR, =O, =CH—R, =$CH_2$, $CH_2$—$CO_2$R, $CO_2$H, $CO_2$R, COR, NR"R'", ($C_{1-12}$ alkylene)-C(O)NR",R'" and ($C_{2-12}$ alkenylene)-C(O)NR'R" and halo.

For each of formulas (A1), (A2), (A3), (A4), (A9), (A10), (A11), (A12), (A13), (A14), (A15) and (A16) the remaining substituent $R_2$ is selected from H, R, OH, OR, $NH_2$, NHR, NRR', $CH_2$—OR, =O, =CH—R, =$CH_2$, $CH_2$—$CO_2$R, $CH_2$—$CO_2$H, $CH_2$—$SO_2$R, O—$SO_2$R, $CO_2$H, $CO_2$R, COR, CN, ($C_{1-12}$ alkylene)-C(O)NR",R'" and ($C_{2-12}$ alkenylene)-C(O)NR'R" and halo. Suitably the remaining substituent $R_2$ is selected from H, R, OR, $NH_2$, NHR, NRR', $CH_2$—OR, =O, =CH—R, =$CH_2$, $CH_2$—$CO_2R$, $CO_2H$, $CO_2R$, COR, ($C_{1-12}$ alkylene)-C(O)NR",R'" and ($C_{2-12}$ alkenylene)-C(O)NR'R" and halo.

For each of formulas (A1), (A3), (A4), (A5), (A7), (A8), (A9), (A11), (A12), (A13), (A15) and (A16) the remaining substituent $R'_2$ is selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2H$, $CO_2R$, COR, CN, ($C_{1-12}$ alkylene)-C(O)NR",R'" and ($C_{2-12}$ alkenylene)-C(O)NR'R" and halo. Suitably the remaining substituent $R'_2$ is selected from H, R, OR, $NH_2$, NHR, NRR', $CH_2$—OR, =O, =CH—R, =$CH_2$, $CH_2$—$CO_2R$, $CO_2H$, $CO_2R$, COR, ($C_{1-12}$ alkylene)-C(O)NR",R'" and ($C_{2-12}$ alkenylene)-C(O)NR'R" and halo.

For each of formulas (A1), (A2), (A3), (A4), (A5), (A6), (A7), (A8), (A13), (A14), (A15) and (A16) the remaining substituent $R_3$ is selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2H$, $CO_2R$, COR, CN, ($C_{1-12}$ alkylene)-C(O)NR",R'" and ($C_{2-12}$ alkenylene)-C(O)NR'R" and halo. Suitably the remaining substituent $R_3$ is selected from H, R, OR, $NH_2$, NHR, NRR', $CH_2$—OR, =O, =CH—R, =$CH_2$, $CH_2$—$CO_2R$, $CO_2H$, $CO_2R$, COR, ($C_{1-12}$ alkylene)-C(O)NR",R'" and ($C_{2-12}$ alkenylene)-C(O)NR'R" and halo.

For each of formulas (A1), (A2), (A4), (A5), (A6), (A8), (A9), (A10), (A12), (A13), (A14) and (A16) the remaining substituent $R'_3$ is selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2H$, $CO_2R$, COR, CN, ($C_{1-12}$ alkylene)-C(O)NR",R'" and ($C_{2-12}$ alkenylene)-C(O)NR'R" and halo. Suitably the remaining substituent $R'_3$ is selected from H, R, OR, $NH_2$, NHR, NRR', $CH_2$—OR, =O, =CH—R, =$CH_2$, $CH_2$—$CO_2R$, $CO_2H$, $CO_2R$, COR, ($C_{1-12}$ alkylene)-C(O)NR",R'" and ($C_{2-12}$ alkenylene)-C(O)NR'R" and halo.

For each of formulas (A1), (A2), (A3), (A4), (A5), (A6), (A7), (A8), (A9), (A10), (A11) and (A12) the remaining substituent $R_7$ is selected from H, R, OH, OR, $NH_2$, NHR, NRR', $CH_2$—OR, $CH_2$—$CO_2R$, $CH_2$—$CO_2H$, $CH_2$—$SO_2R$, O—$SO_2R$, $CO_2H$, $CO_2R$, COR, CN, ($C_{1-12}$ alkylene)-C(O)NR",R'" and ($C_{2-12}$ alkenylene)-C(O)NR'R" and halo. Suitably $R'_6$ is selected from H, $C_{1-12}$ alkyl, OH, O—$C_{1-12}$ alkyl, $OCH_2Ph$, $NH_2$, NH($C_{1-6}$ alkyl), $CO_2H$, $CH_2$—$CO_2H$, $CO_2$($C_{1-6}$ alkyl), $CH_2$—$CO_2$($C_{1-6}$ alkyl) and halo. More suitably $R'_6$ is selected from H, O—$C_{1-6}$ alkyl, $OCH_2Ph$, $NH_2$, NH($C_{1-6}$ alkyl), $CO_2H$, $CH_2$—$CO_2H$, $CO_2$($C_{1-6}$ alkyl) and $CH_2$—$CO_2$($C_{1-6}$ alkyl).

For each of formulas (A1), (A2), (A3), (A5), (A6), (A7), (A9), (A10), (A11), (A13), (A14) and (A15) the remaining substituent $R'_7$ is selected from H, R, OH, OR, $NH_2$, NHR, NRR', $CH_2$—OR, $CH_2$—$CO_2R$, $CH_2$—$CO_2H$, $CH_2$—$SO_2R$, O—$SO_2R$, $CO_2H$, $CO_2R$, COR, CN, ($C_{1-12}$ alkylene)-C(O)NR",R'" and ($C_{2-12}$ alkenylene)-C(O)NR'R" and halo. Suitably $R'_6$ is selected from H, $C_{1-12}$ alkyl, OH, O—$C_{1-12}$ alkyl, $OCH_2Ph$, $NH_2$, NH($C_{1-6}$ alkyl), $CO_2H$, $CH_2$—$CO_2H$, $CO_2$($C_{1-6}$ alkyl), $CH_2$—$CO_2$($C_{1-6}$ alkyl) and halo. More suitably $R'_6$ is selected from H, O—$C_{1-6}$ alkyl, $OCH_2Ph$, $NH_2$, NH($C_{1-6}$ alkyl), $CO_2H$, $CH_2$—$CO_2H$, $CO_2$($C_{1-6}$ alkyl) and $CH_2$—$CO_2$($C_{1-6}$ alkyl).

More suitably the compound of formula (I) is a dimer selected from the formulas (A1), (A6), (A11) and (A16)

More suitably the compound of formula (I) is a dimer with each monomer being the same and being of formula (I).

More suitably the compound of formula (I) is a dimer with each monomer being the same and being of formula (I) where the $R_7$ groups of the monomers form together a bridge having the formula —X-L-X'— linking the monomers.

In embodiment (a), more suitably, the dimer may be represented by formula (A17):

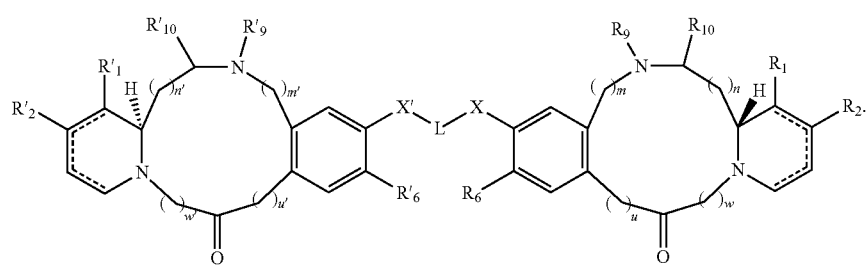

(A17)

In embodiment (a), more suitably, the dimer may be represented by formula (A18):

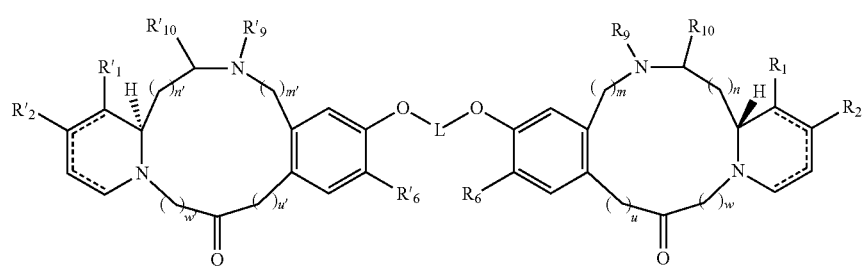

(A18)

In embodiment (a), more suitably, the dimer has the structure (A19):

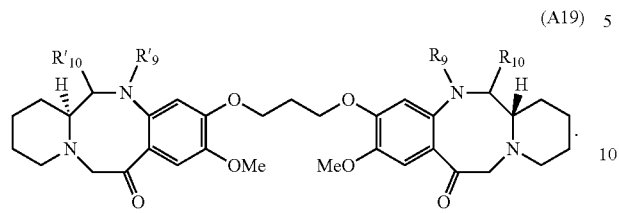

(A19)

In some aspects of embodiment (a) or (b), more suitably, the dimer may be represented by formula (A20):

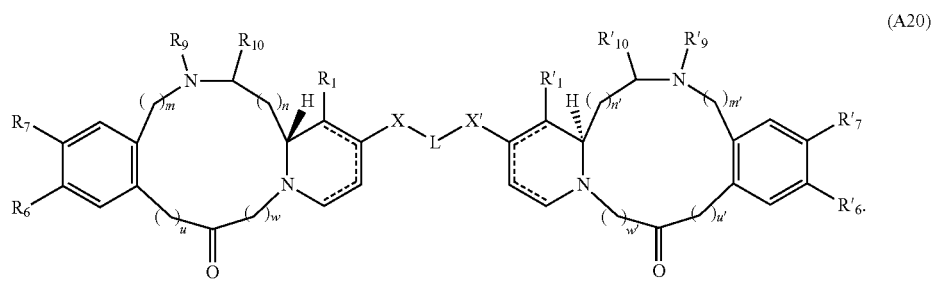

(A20)

In some aspects of embodiment (a) or (b), more suitably, the dimer may be represented by formula (A21):

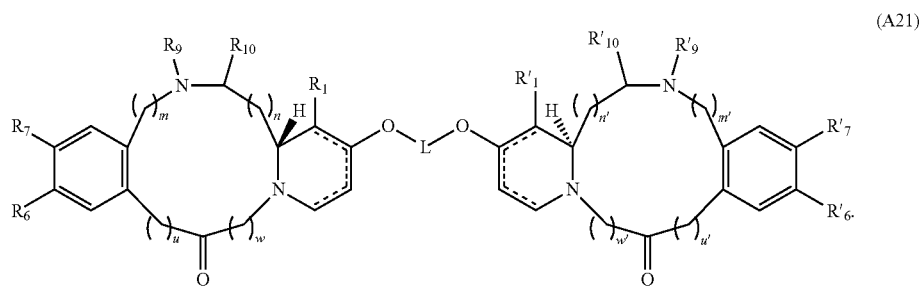

(A21)

In some aspects of embodiment (a) or (b), more suitably, the dimer may be represented by formula (A22):

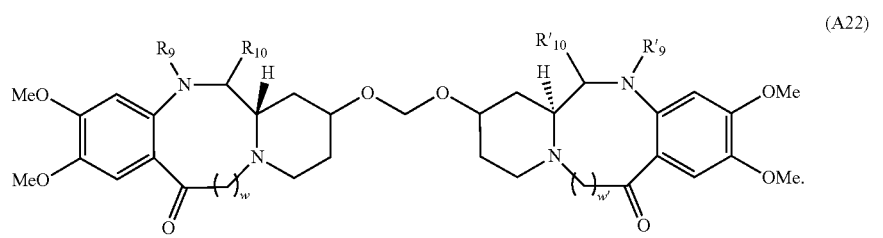

(A22)

In an aspects of embodiment (b), more suitably, the dimer may be represented by formula (A23):

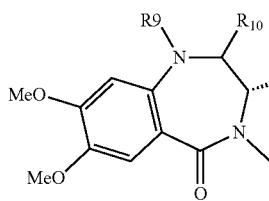 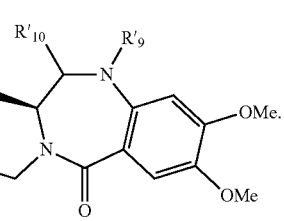

(A23)

Suitably for the above dimer compounds either:
(i) $R_9$ and $R_{10}$ together form a double bond, and $R'_9$ and $R'_{10}$ together form a double bond;
(ii) $R_9$ and $R'_9$ are H, and $R_{10}$ and $R'_{10}$ are OH; or
(iii) $R_9$ and $R'_9$ are H, and $R_{10}$ and $R'_{10}$ are $OR^A$ and $R^A$ is $C_{1-6}$ alkyl.

Applications

The invention finds application in the treatment of proliferative diseases.

In certain aspects a method of treating a proliferative disease is provided, the method comprising administering to a subject a therapeutically effective amount of a compound of the formula (I) and salts or solvates thereof or a composition comprising a compound of formula (I) and salts or solvates thereof.

In certain aspects a method of treating a proliferative disease is provided, the method comprising administering to a subject a therapeutically effective amount of a targeted conjugate comprising a compound of the formula (I) and salts or solvates thereof.

In certain aspects a method of treating a proliferative disease is provided, the method comprising administering to a subject a therapeutically effective amount of an antibody-drug conjugate comprising a compound of the formula (I) and salts or solvates thereof.

In certain aspects of the methods described, the compound of the formula (I) and salts or solvates thereof is a compound where m+n+u+w=0. In certain aspects, the compound of the formula (I) and salts or solvates thereof is a compound according to embodiments (b) and (c). In certain aspects, the compound of the formula (I) and salts or solvates thereof is a compound according to embodiment (b) where m+n+u+w=0 and the compound of formula (I) is a dimer. In certain aspects, the compound of the formula (I) and salts or solvates thereof is a compound according to embodiment (c) where m+n+u+w=0 and the compound of formula (I) is a monomer. In certain aspects, the compound of the formula (I) and salts or solvates thereof is a compound according to formulas (C1), (C2) and (C3) where m+n+u+w=0 and the compound of formula (I) is a monomer.

The term "proliferative disease" refers to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, hepatocellular cancer, gastric or stomach cancer including gastrointestinal cancer, bowel cancer, colon cancer, hepatoma, breast cancer, glioblastoma, cervical cancer, ovarian cancer, prostate cancer, testicular cancer, liver cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Cancers of particular interest include, but are not limited to, breast cancer (both ER positive and ER negative), pancreatic cancer, lung cancer and leukaemia.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

A skilled person is readily able to determine whether or not a candidate compound treats a proliferative condition for any particular cell type.

Suitably subjects are human, livestock animals and companion animals.

In a further aspect, the compound of formula (I) and salts or solvates thereof, may be linked, either directly or indirectly, to a targeting agent (e.g., antibody, antibody fragment, hormone, etc.) to provide a targeted conjugate. The target conjugates of the present disclosure may contain one or multiple compounds of formula (I) (or salts and solvates thereof). A variety of target conjugates are known in the art and may be used with a compound of formula (I) and salts or solvates thereof. For example, in a particular aspect the target conjugate is an antibody-drug conjugate, wherein one or more compounds of formula (I) are linked, directly or indirectly, to the antibody. Therefore, the compound of formula (I) and salts or solvates thereof, may be used as a payload on a targeted conjugate.

Suitably, a compound of formula (I) and salts or solvates thereof, for use as a drug in targeted conjugate is prepared by attaching a compound of formula (I) and salts or solvates thereof to a targeting agent, either directly or via an optional linker group. Suitably, the compound of formula (I) and salts or solvates thereof, is attached to a targeting agent via a linker group. Suitably, the targeted conjugate is for use in the treatment of a disease, more specifically of a proliferative disease. Suitably, the drug may be attached by any suitable functional group that it contains to the targeting agent either directly or via a linker group. Typically, the drug contains, or can be modified to contain, one or more functional groups such as amine, hydroxyl or carboxylic acid groups for attaching the drug to the targeting agent either directly or via a linker group. In some aspects, one or more atoms or groups of the compound of formula (I) may be eliminated during the attachment of the drug to the antibody. In some aspects, the targeting agent binds to a cell surface receptor or a tumor-associated antigen. In some aspects, the targeting agent is an antibody. In some aspects, the targeting agent is a hormone. In some aspects, the targeting agent is a protein. In some aspects, the targeting agent is a polypeptide. In some aspects, the targeting agent is a small molecule (for example, folic acid).

In certain aspects, the compound of the formula (I) and salts or solvates thereof is a compound where m+n+u+w=0. In certain aspects, the compound of the formula (I) and salts or solvates thereof is a compound according to embodiments (b) and (c). In certain aspects, the compound of the formula (I) and salts or solvates thereof is a compound according to embodiments (b) and (c). In certain aspects, the compound of the formula (I) and salts or solvates thereof is a compound according to embodiment (b) where m+n+u+w=0 and the compound of formula (I) is a dimer. In certain aspects, the compound of the formula (I) and salts or solvates thereof is a compound according to embodiment (c) where m+n+u+w=0 and the compound of formula (I) is a monomer. In certain aspects, the compound of the formula (I) and salts or solvates thereof is a compound according to formulas (C1), (C2) and (C3) where m+n+u+w=0 and the compound of formula (I) is a monomer.

Antibody Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells (Xie et al (2006) Expert. Opin. Biol. Ther. 6(3):281-291; Kovtun ef a/(2006) Cancer Res. 66(6): 3214-3121; Law et al (2006) Cancer Res. 66(4):2328-2337; Wu et al (2005) Nature Biotech. 23(9): 1137-1145; Lambert J. (2005) Current Opin. in Pharmacol. 5:543-549; Hamann P. (2005) Expert Opin. Ther. Patents 15(9): 1087-1 103; Payne, G. (2003) Cancer Cell 3:207-212; Trail ef a/(2003) Cancer Immunol. Immunother. 52:328-337; Syrigos and Epenetos (1999) Anticancer Research 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Doman et al., (2009) Blood 114(13):2721-2729; U.S. Pat. Nos. 7,521,541; 7,723,485; WO2009/052249; McDonagh (2006) Protein Eng. Design & Sel. 19(7): 299-307; Doronina et al., (2006) Bioconj. Chem. 17:114-124; Erickson et al., (2006) Cancer Res. 66(8): 1-8; et al., (2005) Clin. Cancer Res. 11:843-852; Jeffrey et al., (2005) J. Med. Chem. 48:1344-1358; Hamblett et al., (2004) Clin. Cancer Res. 10:7063-7070).

In some aspects, the present invention relates to a compound of formula (I) and salts or solvates thereof, for use as a drug in an antibody-drug conjugate. Suitably, a compound of formula (I) and salts or solvates thereof, for use as a drug in an antibody-drug conjugate is prepared by attaching a compound of formula (I) and salts or solvate thereof to an antibody, either directly or via an optional linker group. Suitably, the compound of formula (I) and salts or solvates thereof, is attached to an antibody via a linker group. Suitably, the antibody-drug conjugate is for use in for treatment of a disease, more specifically of a proliferative disease. Suitably, the antibody-drug conjugate is for use in for treatment of a disease, more specifically of a proliferative disease. Suitably, the drug may be attached by any suitable functional group that it contains to the antibody either directly or via a linker group. Typically, the drug contains, or can be modified to contain, one or more functional groups such as amine, hydroxyl or carboxylic acid groups for attaching the drug to the antibody either directly or via a linker group. In some aspects, the antibody of the antibody drug conjugate is an antibody fragment, such as, but not limited to a single chain antibody. In some aspects, one or more atoms or groups of the compound of formula (I) may be eliminated during the attachment of the drug to the antibody. In some aspects, the antibody binds to a cell surface receptor or a tumor-associated antigen.

In some aspects, the present invention relates to the use of a compound of formula (I) and salts or solvates thereof, as a drug in an antibody-drug conjugate. Suitably, the use of a compound of formula (I) and salts or solvates thereof, as a drug in an antibody-drug conjugate is accomplished by attaching a compound of formula (I) and salts or solvates thereof to an antibody, either directly or via an optional linker group. Suitably, the compound of formula (I) and salts or solvates thereof, is attached to an antibody via a linker group. Suitably, the antibody-drug conjugate is for use in for treatment of a disease, more specifically of a proliferative disease. Suitably, the drug may be attached by any suitable functional group that it contains to the antibody either directly or via a linker group. Typically, the drug contains, or can be modified to contain, one or more functional groups such as amine, hydroxyl or carboxylic acid groups for attaching the drug to the antibody either directly or via a linker group. In some aspects, the antibody of the antibody drug conjugate is an antibody fragment, such as, but not limited to a single chain antibody. In some aspects, one or more atoms or groups of the compound of formula (I) may be eliminated during the attachment of the drug to the antibody. In some aspects, the antibody binds to a cell surface receptor or a tumor-associated antigen.

In certain aspects, the compound of the formula (I) and salts or solvates thereof is a compound where m+n+u+w=0. In certain aspects, the compound of the formula (I) and salts or solvates thereof is a compound according to embodiments (b) and (c). In certain aspects, the compound of the formula (I) and salts or solvates thereof is a compound according to embodiments (b) and (c). In certain aspects, the compound of the formula (I) and salts or solvates thereof is a compound according to embodiment (b) where m+n+u+w=0 and the compound of formula (I) is a dimer. In certain aspects, the compound of the formula (I) and salts or solvates thereof is a compound according to embodiment (c) where m+n+u+w=0 and the compound of formula (I) is a monomer. In certain aspects, the compound of the formula (I) and salts or solvates thereof is a compound according to formulas (C1), (C2) and (C3) where m+n+u+w=0 and the compound of formula (I) is a monomer.

The substituent groups of the compounds of formula (I) may interact with DNA sequences and may be selected so as to target specific sequences.

Antibody and Antibody Fragments

The term "antibody" specifically covers monoclonal antibodies, polyclonal antibodies, dimers, multimers, multispecific antibodies (e.g., bispecific antibodies), intact antibodies and antibody fragments, so long as they exhibit the desired biological activity, for example, the ability to bind a desired antigen on a target cell or tissue. Antibodies may be murine, human, humanized, chimeric, or derived from other species. An antibody is a protein generated by the immune system that is capable of recognizing and binding to a specific antigen. (Janeway, C, Travers, P., Walport, M., Shlomchik (2001) Immuno Biology, 5th Ed., Garland Publishing, New York). A target antigen generally has numerous binding sites, also called epitopes, recognized by CDRs on the antibody. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. lgG1, lgG2, lgG3, lgG4, lgA1 and lgA2) or subclass, or allotype (e.g. human G1 m1, G1 m2, G1 m3, non-G1 m1 [that, is any allotype other than G1 m1], G1 m17, G2m23, G3m21, G3m28, G3m11, G3m5, G3m13, G3m14, G3m10, G3m15, G3m16, G3m6, G3m24, G3m26, G3m27, A2 m1, A2m2, Km1, Km2 and Km3) of immunoglobulin molecule. The immunoglobulins can be derived from any species, including human, murine, or rabbit origin.

As used herein, "binds an epitope" is used to mean the antibody binds an epitope with a higher affinity than a non-specific partner such as Bovine Serum Albumin (BSA, Genbank accession no. CAA76847, version no. CAA76847.1 Gl:3336842, record update date: Jan. 7, 2011 02:30 PM). In some embodiments the antibody binds an epitope with an association constant (Ka) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions.

The term "antibody fragment" refers to a portion of a full length antibody, for example, the antigen binding or variable region thereof. Examples of antibody fragments include Fab, Fab', F(ab')2, and scFv fragments; diabodies; linear antibodies; fragments produced by a Fab expression library, anti-idiotypic (anti-Id) antibodies, CDR (complementary determining region), single-chain antibody molecules; and multispecific antibodies formed from antibody fragments and epitope-binding fragments of any of the above which immunospecifically bind to target antigens, such as, for example, cancer cell antigens, viral antigens or microbial antigens. The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant or epitope on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The antibodies, including monoclonal antibodies, herein specifically include "chimeric" antibodies in which a portion of the antibody structure, for example the heavy and/or light chain, is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies include "primatized" antibodies comprising variable domain antigen-binding sequences derived from a non-human primate (e.g. Old World Monkey or Ape) and human constant region sequences. An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1 q binding; complement dependent cytotoxicity; Fc receptor binding; antibody-dependent cell-mediated cytotoxicity (ADCC); phagocytosis; and down regulation of cell surface receptors such as B cell receptor and BCR.

The antibodies disclosed herein may be modified. For example, to make them less immunogenic to a human subject. This may be achieved using any of a number of techniques familiar to the person skilled in the art, such as humanisation.

Administration & Dose

Compounds of formula I may be administered alone or in combination with one or another or with one or more pharmacologically active compounds which are different from the compounds of formula I.

Compounds of the invention may suitably be combined with various components to produce compositions of the invention. Suitably the compositions are combined with a pharmaceutically acceptable carrier or diluent to produce a pharmaceutical composition (which may be for human or animal use). Suitable carriers and diluents include isotonic saline solutions, for example phosphate-buffered saline. Useful pharmaceutical compositions and methods for their preparation may be found in standard pharmaceutical texts. See, for example, *Handbook for Pharmaceutical Additives,* 3rd Edition (eds. M. Ash and I. Ash), 2007 (Synapse Information Resources, Inc., Endicott, N.Y., USA) and *Remington: The Science and Practice of Pharmacy,* 21st Edition (ed. D. B. Troy) 2006 (Lippincott, Williams and Wilkins, Philadelphia, USA) which are incorporated herein by reference.

The compounds of the invention may be administered by any suitable route. Suitably the compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form.

The compounds of the invention, their pharmaceutically acceptable salts, and pharmaceutically acceptable solvates of either entity can be administered alone but will generally be administered in admixture with a suitable pharmaceutical excipient diluent or carrier selected with regard to the intended route of administration and standard pharmaceutical practice.

For example, the compounds of the invention or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compounds of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

The compounds of the invention can also be administered parenterally, for example, intravenously, intra-arterially, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Suitably formulation of the invention is optimised for the route of administration e.g. oral, intravenously, etc.

Administration may be in one dose, continuously or intermittently (e.g. in divided doses at appropriate intervals) during the course of treatment. Methods of determining the most effective means and dosage are well known to a skilled person and will vary with the formulation used for therapy, the purpose of the therapy, the target cell(s) being treated, and the subject being treated. Single or multiple administrations can be carried out with the dose level and the dose regimen being selected by the treating physician, veterinarian, or clinician.

Depending upon the disorder and patient to be treated, as well as the route of administration, the compositions may be administered at varying doses. For example, a typical dosage for an adult human may be 100 ng to 25 mg (suitably about 1 micro g to about 10 mg) per kg body weight of the subject per day.

Suitably guidance may be taken from studies in test animals when estimating an initial dose for human subjects. For example when a particular dose is identified for mice, suitably an initial test dose for humans may be approx. 0.5× to 2× the mg/Kg value given to mice.

Other Forms

Unless otherwise specified, included in the above are the well known ionic, salt, solvate, and protected forms of these substituents. For example, a reference to carboxylic acid (—COOH) also includes the anionic (carboxylate) form (—COO—), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O—), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; alpha- and beta-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH.

A reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not apply to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof.

Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

Compounds of Formula 1, which include compounds specifically named above, may form pharmaceutically acceptable complexes, salts, solvates and hydrates. These salts include nontoxic acid addition salts (including di-acids) and base salts.

If the compound is cationic, or has a functional group which may be cationic (e.g. —$NH_2$ may be —$NH_3^+$), then an acid addition salt may be formed with a suitable anion. Examples of suitable inorganic anions include, but are not limited to, those derived from the following inorganic acids hydrochloric acid, nitric acid, nitrous acid, phosphoric acid, sulfuric acid, sulphurous acid, hydrobromic acid, hydroiodic acid, hydrofluoric acid, phosphoric acid and phosphorous acids. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

For example, if the compound is anionic, or has a functional group which may be anionic (e.g. —COOH may be —COO—), then a base salt may be formed with a suitable cation. Examples of suitable inorganic cations include, but are not limited to, metal cations, such as an alkali or alkaline earth metal cation, ammonium and substituted ammonium cations, as well as amines. Examples of suitable metal cations include sodium ($Na^+$) potassium ($K^+$), magnesium ($Mg^{2+}$), calcium ($Ca^{2+}$), zinc ($Zn^{2+}$), and aluminum ($Al^{3+}$). Examples of suitable organic cations include, but are not limited to, ammonium ion (i.e. $NH^{4+}$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2011)

Pharmaceutically acceptable salts may be prepared using various methods. For example, one may react a compound of Formula 1 with an appropriate acid or base to give the desired salt. One may also react a precursor of the compound of Formula 1 with an acid or base to remove an acid- or base-labile protecting group or to open a lactone or lactam group of the precursor. Additionally, one may convert a salt of the compound of Formula 1 to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

It may be convenient or desirable to prepare, purify, and/or handle a corresponding solvate of the active compound. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-d6, DMSO-d6).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions.v In such cases, non-stoichiometry will typically be observed.

Compounds of formula I include imine, carbinolamine and carbinolamine ether forms of the PDD or BPD. The carbinolamine or the carbinolamine ether is formed when a nucleophilic solvent (H₂O, ROH) adds across the imine bond of the PBD moiety. The balance of these equilibria between these forms depend on the conditions in which the compounds are found, as well as the nature of the moiety itself.

These compounds may be isolated in solid form, for example, by lyophilisation.

Further particular and preferred aspects are set out in the accompanying independent and dependent claims. Features of the dependent claims may be combined with features of the independent claims as appropriate, and in combinations other than those explicitly set out in the claims.

Synthetic Strategies

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations, A Guide to Functional Group Preparations*, 2nd Ed (2010), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a diacid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry*, 4th Edition, (2006) and P. Kocienski, *Protective Groups*, 3rd Edition (2005).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

Preferred General Synthetic Strategies

A key step in the synthesis of the PDD and BPD compounds is the ring closure step to form a 7-membered or 8-membered B-ring. Suitable synthetic strategies for this ring closure step are known in the art and have been reviewed with regard to the preparation of the related PBD compounds (1, 21).

Synthetic Strategies Involving Preparation of the B-Ring Via a Dilactam Several of these synthetic strategies for preparing PDD or BPD compounds are based on forming a key dilactam that can then undergo a reduction reaction to provide the desired PDD or BPD compounds.

Route 1

The nitro group of precursor [1] may be reduced to a nucleophilic anilinic amine [2] which may then react with an electrophilic substituent from the piperidine ring to produce the B-ring of the dilactam [3] by formation of an amide. Catalytic hydrogenation in the presence of palladium on charcoal may be used to carry out the reduction (WO 2004/043963) followed by acid catalysed cyclisation (37), with e.g. HCl, to produce the key dilactam [3]. Other reagents and conditions may be used for carrying out the reduction (35-38). $R_1$-$R_8$ below represent the desired final substituents, or the precursors or protected forms thereof.

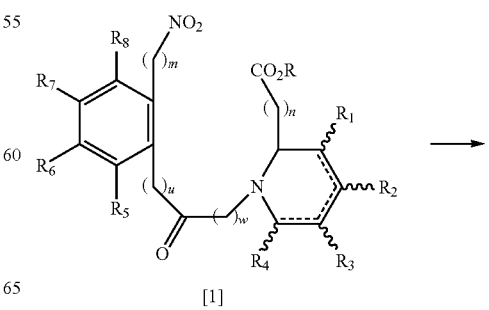

[1]

-continued

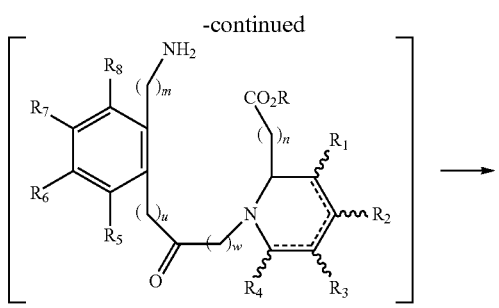

[2]

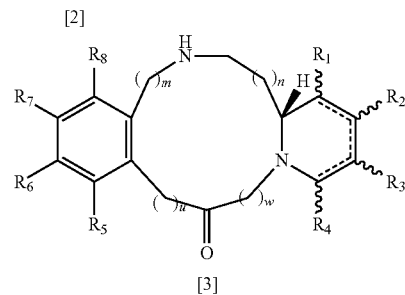

[3]

The amide group of the dilactam [3] formed in the cyclisation step may be reduced to provide the desired PDD or BPD compound [4] using covalent hydrides, such as LiAlH$_4$ or NaBH$_4$ (21, 39). The desired PDD or BPD compound [4] is shown below as an imine but, as discussed above, the N=C may also exist in the form of a carbinolamine [NH—CH(OH)], or as a carbinolamine alkyl ether. The efficiency of the regioselective reduction of the carbonyl is affected by factors such as A-ring substitution pattern, nitrogen-protecting groups, the C-ring substitution pattern and the source of the hydride. Hence, protection of the nitrogen with an appropriate nitrogen protecting group may assist the dilactam reduction. A protecting group may be added by treating the dilactam [3] with a kinetic base (e.g. NaH), followed by addition of an electrophile (e.g. CH$_3$—O—CH$_2$—Cl [MOM-Cl] as shown below) which does not affect the stereochemistry of the pyrrolidine (39).

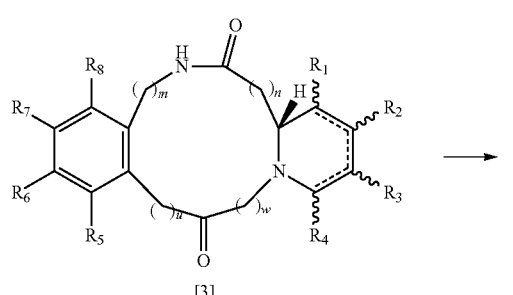

[3]

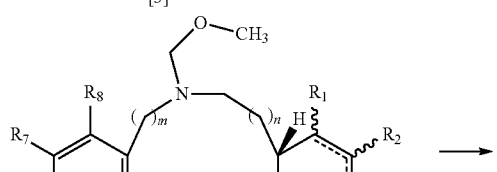

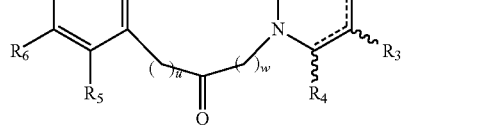

-continued

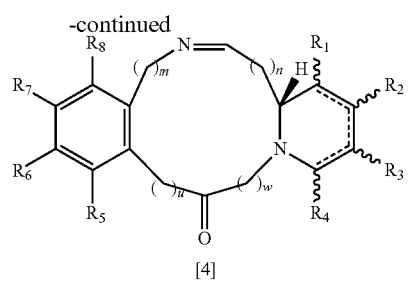

[4]

Route 2

The dilactam [3] may also be produced by a reductive cyclization of an azido group with a carboxylate ester [6]. The azide compound [6] may be prepared by reacting the corresponding nitro compound with sodium azide, NaN$_3$ (40). The azide reduction may be carried out using silicon-based reagents, e.g. hexamethyldisilathiane [HMDST](40-42), ferrous sulphate (43) or ferric chloride with sodium iodide (44).

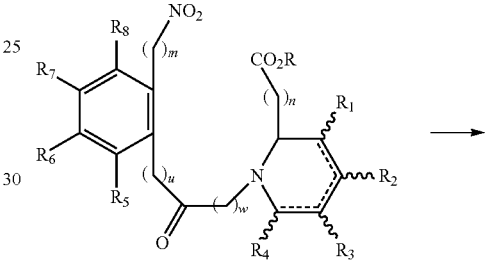

[1]

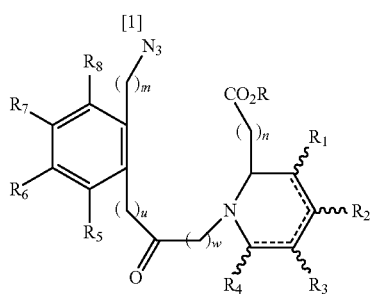

[6]

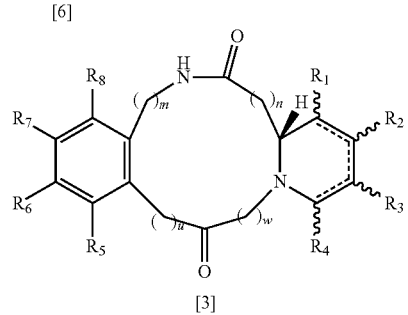

[3]

The dilactam [3] can be reduced to the desired PDD or BPD compound [4] as discussed in relation to Route 1 above.

Route 3

The dilactam [9] may be prepared using a hypovalent iodine reagent phenyliodine (III) bis(trifluoroacetate) PIFA to cyclize the B-ring (45). Saponification of the precursor [7] with LiOH and amide coupling with methoxamine give the N-alkoxyamide [8]. Treatment of [8] with PIFA removes the hydrogen from the nitrogen to produce an N-acylnitrenium species which undergoes an intramolecular electrophilic aromatic substitution to provide the dilactam [9], where $R_9$ is $OCH_3$. The $R_9$ methoxy group can be removed from dilactam [9] by treatment with molybdenum hexacarbonyl to give the dilactam [3], where $R_9$ is H, which may then be reduced to the desired PDD or BPD compound [4] as in Route A above.

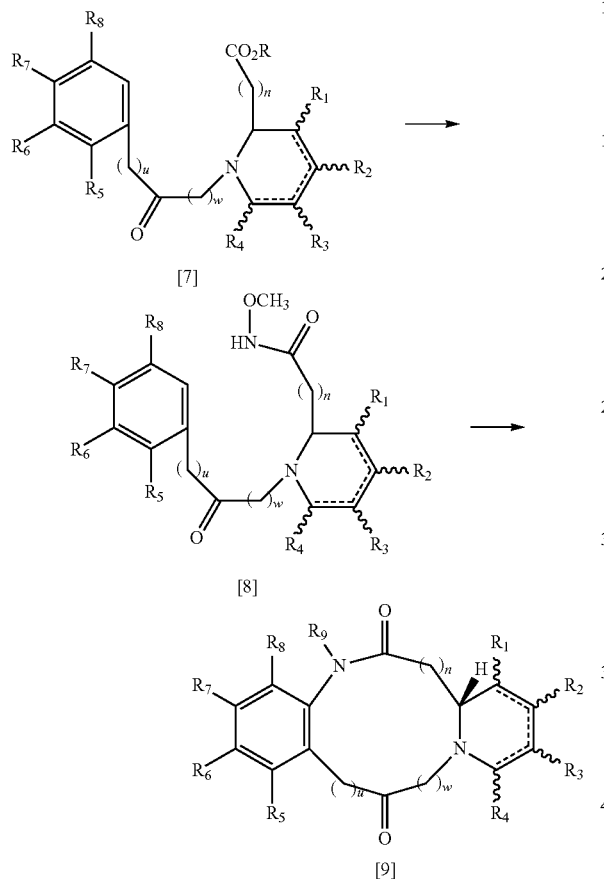

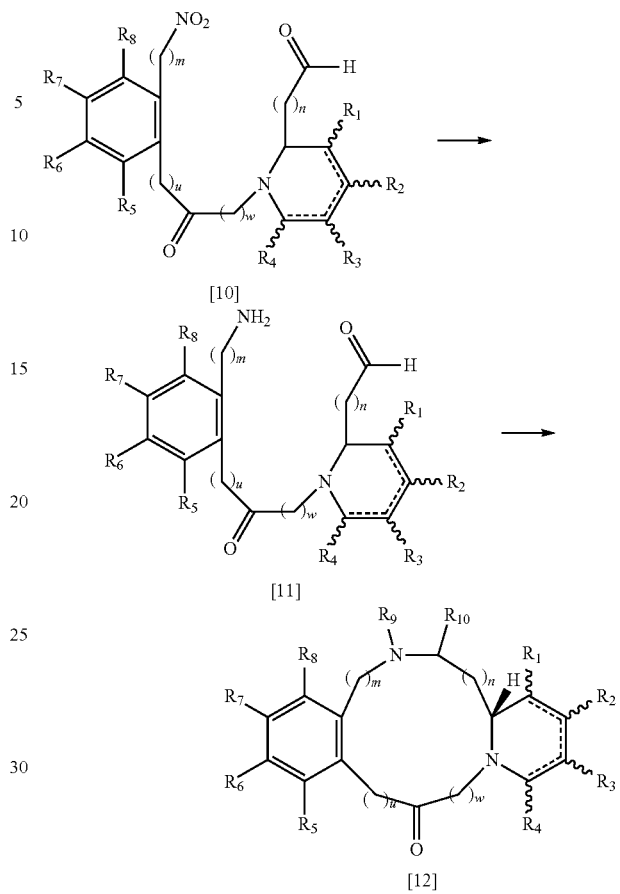

The nucleophilic character of the phenyl ring is critical to the cyclization and electron-donating groups, such as alkoxy groups e.g. $CH_3O$—, at $R_6$ and $R_7$ are important to provide the required nucleophilic character.

Synthetic Strategies Involving Preparation of the B-Ring by Cyclization of an Aldehyde or an Aldehyde Equivalent These synthetic strategies form the B-ring by cyclization using an aldehyde, a protected aldehyde (e.g. acetal or thioacetal) or a hydroxyl group (which can be oxidised to the aldehyde) as an electrophilic group in the PDD or BPD compound precursor.

Route 4

Route 4 involves reduction of a nitro group on the A-ring of the precursor [10] to give the amine [11] which then undergoes a cyclization with the aldehyde group to form the B-ring [12]. The reductive cyclization may be carried out using catalytic hydrogenation with palladium on charcoal (46, 47) or with Raney-nickel (48, 49), although other reductive cyclization conditions are known (50, WO2007/085930). The desired PDD or related compound [12] commonly may be the form of the carbinolamine [$R_9$=H, $R_{10}$=OH], or of an imine where $R_9$ and $R_{10}$ together form a double bond.

Route 5

A useful strategy to form PDD or BPD compounds is to use a thioacetal as a protected aldehyde. Protection of the aldehyde can be carried out after A- to C-ring coupling or alternatively a C-ring carrying a thioacetal may be coupled to the A-ring.

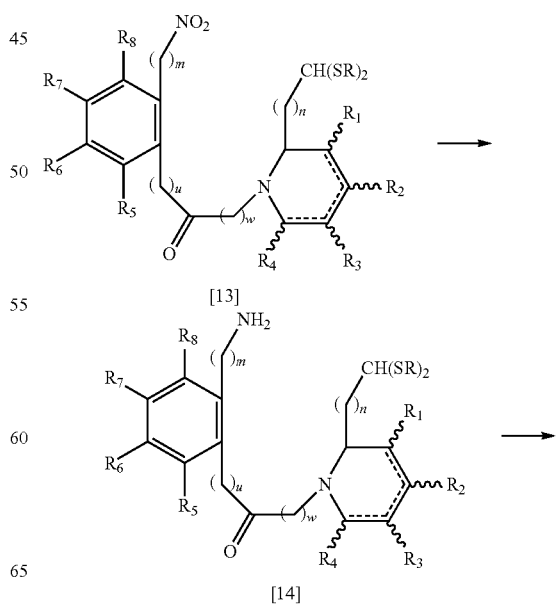

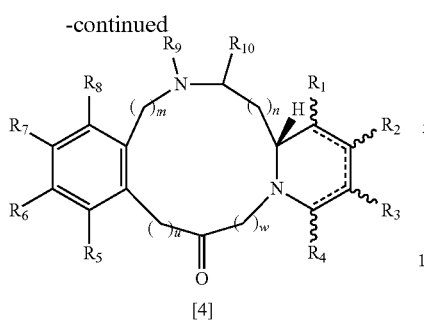

[4]

The amine [14] may be prepared by reduction of the nitro group of [13], subsequent removal of the thioacetal and cyclization provides the desired PDD or BPD compound [4]. Mercury (II) chloride may be used as the reagent for removing the thioacetal and effecting cyclization (51), although other reagents may also be used (52, 53).

Generally, the thioacetal group —CH(SR)$_2$ has C1-C7 alkyl groups, such as methyl or ethyl, as the R groups and suitable thioacetal protected C-rings may be prepared via a literature method (54).

The thioacetal protecting group is robust and a wide variety of reactions may be carried out on the nitro thioacetal scaffold [13] as shown by the preparation of the related monomeric PBD conjugates, such as those involving polypyrrole moieties (55), and the related dimeric PBD species (33, 56, 57) using this strategy.

Route 6

Acetals [15] where R is a C1-C7 alkyl group, such as methyl or ethyl, may be used as a protected aldehyde and, following deprotection under mild acidic conditions, may be cyclized to form the B-ring of PDD or BPD compounds [4] (21).

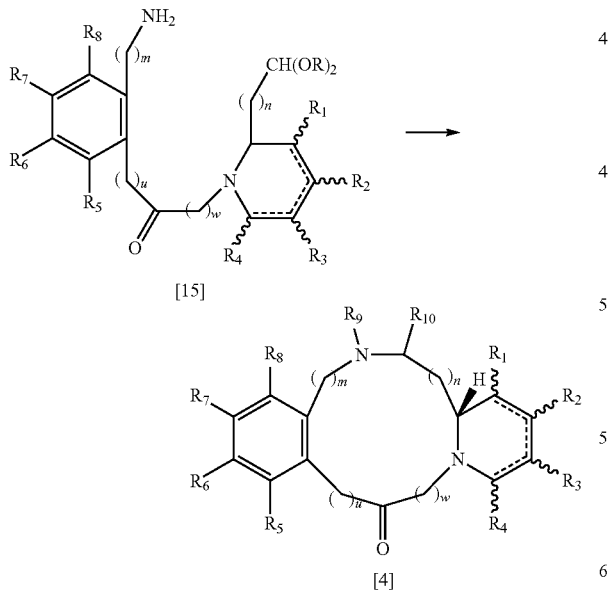

[15]

[4]

Zinc chloride and chlorotrimethylsilane may provide a stereoselective cyclization (58, 59).

Route 7

The PDD or BPD compound [4] may be prepared by consecutive Staudinger/intramolecular aza-Wittig reactions of a precursor [16] containing azide and aldehyde functional groups. The reaction proceeds via an iminophosphorane intermediate [17] (34, 60, 61).

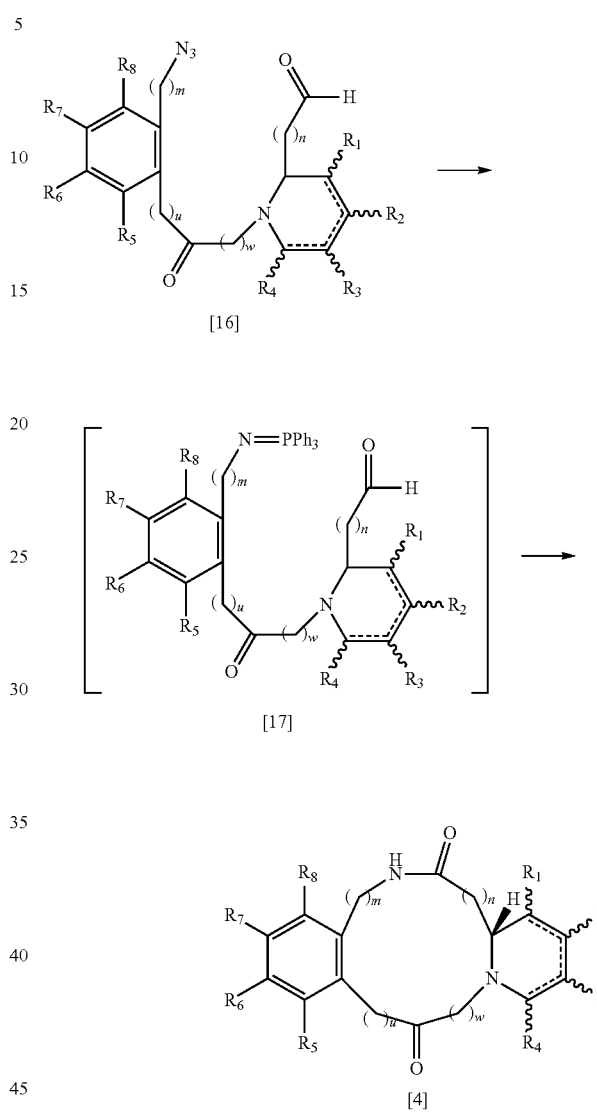

[16]

[17]

[4]

The precursor [16] containing azide and aldehyde functional groups may be prepared from 2-nitrobenzoic acid derivatives and 2-piperidinylmethanol derivative (34).

Route 8

Cyclization of the B-ring may be achieved using a precursor [18] containing an amine group that has a protecting group at R$_9$ (30, 62-66, WO 00/12508, WO2005/085260). The hydroxyl group in [18] is oxidised to an aldehyde [19] which may be reacted with the protected amine to form the carbinolamine [12] where R$_9$=protecting group and R$_{10}$=OH. The protecting group R$_9$ in the carbinolamine [18] prevents imine formation through elimination, which allows a range of further modifications to be carried out on the compound without any complications from an imine. Thus, [18] may undergo addition of side chain substituents before formation of the imine. Deprotection of the nitrogen can be carried out as the last step to give the imine [4].

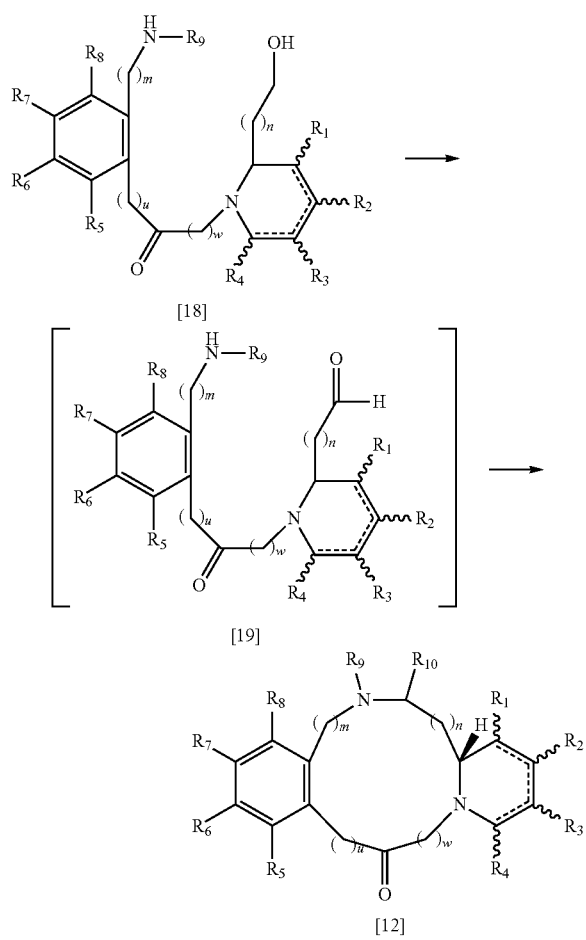

[18]

[19]

[12]

When alloc is used as the protecting group $R_9$, then the deprotection to remove the nitrogen protecting group of [12] is carried out using palladium, followed by the elimination of water to give the imine.

BRIEF DESCRIPTION OF THE DRAWINGS

Embodiments of the present invention will now be described further, with reference to the accompanying drawings, in which.

EXAMPLES

Figure 1:
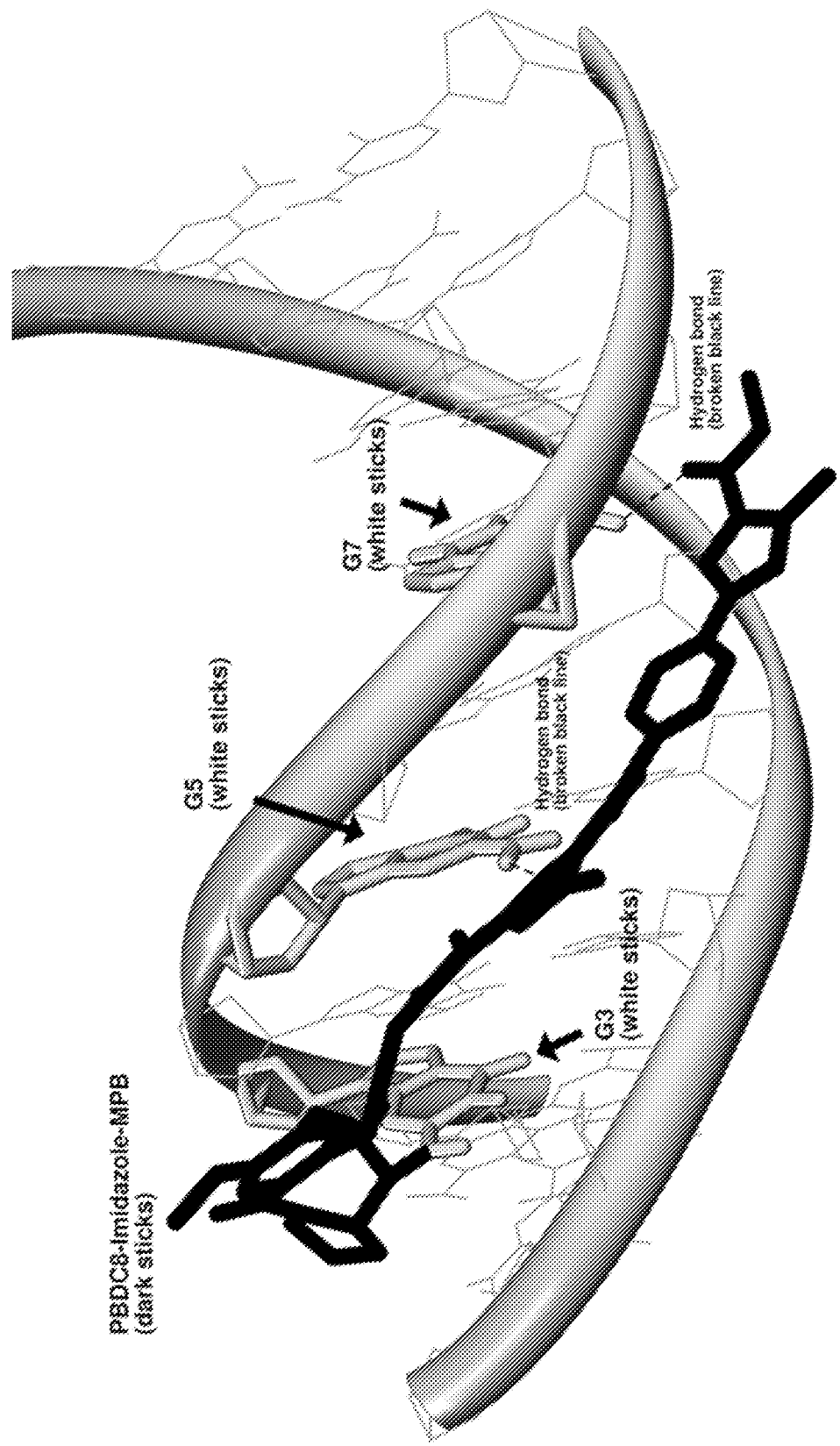
FIG. 1: Snapshot of MD simulation showing the highly cytotoxic KMR-28-39 (PBD-C8-Imidazole-MPB) interacting with 5'-GGGGGGGGCC-3'.

Unless otherwise stated synthetic building blocks and reagents were purchased from Maybridge Chemicals (UK), Fluorochem (UK), ChemShuttle Inc (USA) and Sigma-Aldrich (UK). Solvents were purchased from Sigma-Aldrich (UK) and Fisher Scientific (UK). Anhydrous reactions were carried out in pre-oven-dried glassware under an inert atmosphere of nitrogen. Anhydrous solvents were used as purchased without further drying. Thin Layer Chromatography (TLC) was performed on silica gel aluminum plates (Merck 60, $F_{254}$), and flash column chromatography was carried out using silica gel (Merck 9385, 230-400 mesh ASTM, 40-63 µM) whilst monitoring by thin layer chromatography: UV (254 nm) and an aqueous alkaline solution of potassium permanganate as stain. All NMR spectra were obtained at room temperature using a Bruker DPX400 spectrometer, for which chemical shifts are expressed in ppm relative to the solvent and coupling constants are expressed in Hz. All Liquid Chromatography Mass Spectroscopy (LCMS) analysis were performed on a Waters Alliance 2695 with water (A) and acetonitrile (B) comprising the mobile phases. Formic acid (0.1%) was added to the acetonitrile to ensure acidic conditions throughout the analysis. The gradient conditions were: 95% A/5% B for 2 min. which was increased to 50% B over 3 min. The gradient was then held at 50% B for 1 min. and then increased to 95% B over 1.5 min. The quantity of B was then returned to 5% over 1.5 min. and held constant for 0.5 min. (the total duration of each run being 10 mins.) The flow rate was 0.5 mL/min., 200 µL was split via a zero dead volume T piece which passed into the mass spectrometer. The wavelength range of the UV detector was 220-400 nm. Function type: Diode array (535 scans). Column type: Monolithic C18 50×4.60 mm. Mass spectrometry data were collected using a Waters Micromass ZQ instrument coupled to a Waters 2695 HPLC with a Waters 2996 PDA. Waters Micromass ZQ parameters used were: Capillary (kN), 3.38; Cone (V), 35; Extractor (V), 3.0; Source temperature (° C.), 100; Desolvation Temperature (° C.), 200; Cone flow rate (L/h), 50; De-solvation flow rate (L/h), 250. Microwave reactions were carried out on an Anton Paar Monowave 300 microwave synthesis reactor. Yields refer to isolated material (homogeneous by TLC or NMR) unless otherwise stated and names are assigned according to IUPAC nomenclature.

General Methods: Molecular Dynamics (MD) Simulations

Molecular dynamics simulations consist of the calculation of the time-dependent behaviour of molecular systems, and have provided valuable information on the changes in conformations of biomolecules (for example proteins or nucleic acids) as predicted over a certain time-course.

Classical MD simulations can be performed in explicit or implicit solvent, with explicit containing solvent molecules (and thus dramatically increasing the necessary computational power), and implicit solvent containing a representation of solvent in the form of a continuous medium.

In explicit solvent simulations, all atoms contained in the system (i.e. all nucleic acid, ligand and water atoms in a DNA sequence) are moved in short time-steps (e.g. 2fs), each step is saved and the forces acting on the atoms are calculated and an atom's position and velocity are updated using Newton's Laws. This process is repeated billions of times for every atom in the system, resulting in the production of a dynamic simulation trajectory, illustrating an atom's movements within a system. An identical process is undertaken for implicit solvent simulations, except without solvent molecules and as such the complex, on its own, is simulated.

Molecular dynamics simulations were conducted using AMBER (vii) (67) software. Each DNA sequence was constructed using nab, antechamber was used to convert the structures to mol2 files with the application of Gasteiger charges, and missing parameters were generated for each ligand using parmchk. The gaff and DNA optimized parm99bsc0 (68) force-fields were loaded for DNA and xleap was used to manually position each ligand into each sequence individually by creating the covalent bond between the exocyclic $NH_2$ of the reacting guanine and each ligand, parameters for which were derived through molecular mechanics calculations. Parm99bsc0 was used as it is a refined version of parm99, where a/y rotation of nucleic acids is considered (68). $Na^+$ ions were placed along the DNA backbone using xleap to neutralize the DNA, and adducts were solvated using a truncated octahedron TIP3P water box of maximum dimension 10 Å. Each adduct was minimized in a gradient manner by initially placing the DNA under a high force constraint to enable the ligand to find its local energy minimum, followed by a reduction in force in a periodic manner and a relaxation of restraints. Once the full system was minimized, it was heated slowly to 300 K over 20 ps using the SHAKE algorithm to restrict vibrations of C—H bonds (69), followed by an unrestrained equilibration step of 100 ps to relax the density of water. Once in equilibrium, production simulations were run for a period of 10 ns and atomic coordinates were saved at 1-ps intervals. Production simulations of 10 ns were conducted using an identical protocol, with structures docked in the minor groove of each sequence in a non-covalent manner. In this process, PDD molecules were docked in the minor groove with their imines located within 2 Å of the intended reacting guanine without the formation of the covalent bond.

Simulations of 10 ns duration were undertaken and free energy calculated using the MM-PBSA method in AMBER 11, a method shown to be most accurate in free energy estimation in explicit solvent simulations (70).

Binding free energy can be calculated as follows:

$$\Delta G^{\circ}_{bind} = \Delta G^{\circ}_{bind\ vacuum} + \Delta G^{\circ}_{complex} - (\Delta G^{\circ}_{ligand} + \Delta G^{\circ}_{receptor})$$

where $\Delta G^{\circ}_{bind}$ is determined by solving the linearized Poisson-Boltzmann equation (78)

$$\Delta G^{\circ}_{complex} = E_{MM} + G_{polar\ solvation\ energy} + G_{nonpolar\ solvation\ energy} - TS$$

Solvation energies (both polar and non-polar) are considered, $E_{MM}$ corresponds to internal, electrostatic and vdW interactions and S is solute entropy.

The final binding energy is represented as:

$$\Delta G^{\circ}_{bind} = \Delta E_{MM} + \Delta G^{\circ}_{solv} - T\Delta S$$

Entropy contribution can be calculated using normal mode analysis. However, this is impractical as normal mode analysis calculations introduce significant error into final values and are computationally expensive. As states of similar entropy are being assessed and therefore comparable, these calculations were not undertaken.

$$G = E_{MM} + G_{PBSA} - TS_{MM}$$

$$E_{MM} = E_{bond} + E_{angle} + E_{tors} + E_{vdw} + E_{elec}$$

where:
G=calculated average free energy (kcal/mol),
$G_{PBSA}$=solvation free energy (Poisson Boltzmann equation with estimate of non-polar free energy)
$TS_{MM}$=solute entropy
$E_{MM}$=average molecular mechanical energy
(consisting of energies for bond, angle, torsion, van der Waals and electrostatics One hundred snapshots of the MD simulations were taken at equal intervals over the 10 ns duration, and molecular mechanics (MM) calculations were performed using pbsa (67).

Non-Covalent Simulations

Standard PBDs locate the minor groove of DNA through a combination of hydrophobic and non-covalent interactions, before forming an essential hydrogen bond between N10 of the molecule and the exocyclic C2-amino of guanine. Once this hydrogen bond is formed, the PBD is pulled into the minor groove and undergoes nucleophilic attack to form the covalent attachment. As such, it is necessary to perform non-covalently bound simulations to assess the DNA-interactive potential of DNA-targeting molecules such as PDDs. Free energy of binding calculations performed on these simulations help in the assessment of DNA-binding potential.

Free energy of binding (kcal/mol) calculations are used to ascertain the degree of affinity of a ligand for its receptor. Hydrogen bonding analysis and the examination of non-bonded interactions also support the evaluation of binding of ligands to sequences of DNA. As ligands recognize the minor groove through these interactions, quantitative and qualitative analysis of each provides a valuable insight into the strength of DNA: ligand interaction.

Example 1

PDD monomers were compared in non-covalent MD simulations to an equivalent PBD monomer called DC-81. This allowed for the comparison of potential DNA binding affinity of the new PDD monomers.

A definite hierarchy can be observed, with PDD 1 and PDD 3 showing free energy of binding values greater than −20 kcal/mol, close to the PBD DC-81. Furthermore, in non-covalent simulations each of PDD 1 and PDD 3 maintain a hydrogen bond between the B-ring nitrogen and C2-amino of guanine, a vital pre-requisite to nucleophilic attack. Due to a lack of interaction with the C2-amino of guanine, PDD2 exhibited poorer free energy of binding than PDD1 or PDD3, and PDD2 does not remain over the intended binding triplet (5'-ΔGA-3').

TABLE 1

Free energy of binding (kcal/mol) of each PDD monomeric structure with the sequence 5'-TATAAGATATA-3'

| Structure | Free Energy of Binding (kcal/mol) (+/−10% Standard Deviation) in 5'-TATA<u>AGA</u>TATA-3' (binding site underlined) |
|---|---|
| DC-81 | −23.12 |

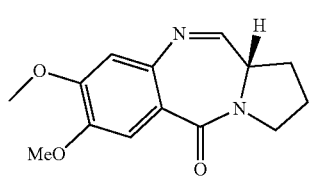

TABLE 1-continued

Free energy of binding (kcal/mol) of each PDD monomeric structure with the sequence 5'-TATAAGATATA-3'

| Structure | Free Energy of Binding (kcal/mol) (+/−10% Standard Deviation) in 5'-TATA<u>AGA</u>TATA-3' (binding site underlined) |
|---|---|
| PDD 1 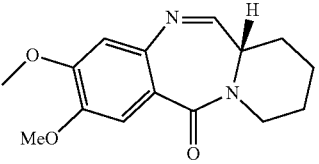 | −20.72 |
| PDD 2 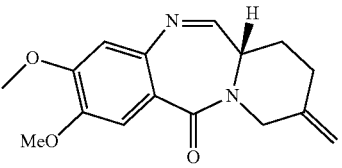 | −14.20 |
| PDD 3 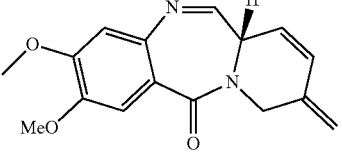 | −23.40 |

Example 2

The C8-linked PBD dimer structure SJG-136 (shown below) is currently in Phase II clinical trials, selectively interacting with the DNA sequence 5'-Pu-GATC-Py-3'.

SJG-136

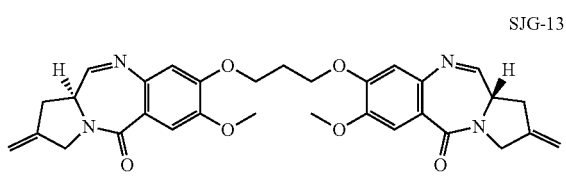

Furthermore, MD simulations have shown that when covalently bound in the DNA minor groove to a sequence (5'-TATAGATCTATA-3') idealised for interaction, the PBD dimer SJG-136 is comfortably accommodated in the minor groove, causing negligible distortion of the DNA helix, both of which are pre-requisites for the cytotoxic activity of DNA-interactive agents.

The PDD (6-7-6) family of agents also show negligible DNA distortion when covalently bound in the minor groove.

PDDs, and particularly PDD-1 and PDD-3 should have similar DNA-interactivity to PBDs in DNA interactivity and cytotoxicity due to their isohelicity with the minor groove floor.

Molecular models suggest an identical span of PDD dimers to SJG-136, and the same lack of DNA distortion when covalently bound to a 5'-TATAGATCTATA-3' sequence of DNA.

These observations are supported by free energy of binding calculations which illustrate that the PDD dimer has a similarly strong free energy of binding value as is observed for SJG-136.

TABLE 2

Free energy of binding (kcal/mol) of SJG-136, PDD Dimer and C-ring Linked PDD dimer structures with the sequence
5'-TATAGATCTATA-3'

| Structure | Free Energy of Binding (kcal/mol) in 5'-TATA<u>GATC</u>TATA-3' (binding site underlined) |
|---|---|
| SJG-136 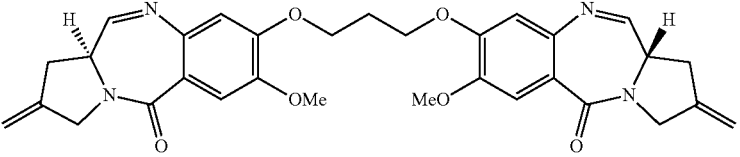 | −45.73 |
| PDD Dimer 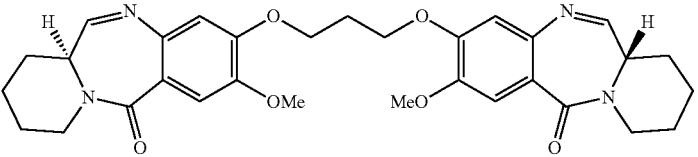 | −40.43 |
| C-ring Linked PDD Dimer 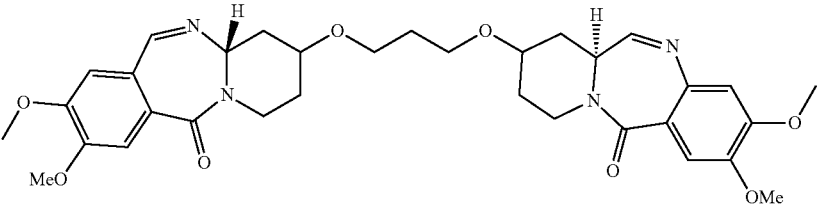 | −38.62 |

Example 3

An example of the equivalence of the PDD family to the PBDs is in the design of a molecule using a GC-selective MPB unit. The highly cytotoxic PBD conjugate KMR-28-39 is active in the femtomolar range in some cancer cell lines, a characteristic attributed to its strong affinity for GC-rich DNA sequences. KMR-28-39 is comprised of a PBD coupled to an imidazole-MPB unit through its C8-position, with the imidazole-MPB providing the structure with its enhanced GC-selectivity through unique molecular interactions with DNA bases (see Table 3).

When the Imidazole-MPB moiety is tethered at R7 of the BPD molecule (equivalent to the C8 position of PBDs), the new BPD-Imidazole-MPB structure produces the same interactions with DNA as KMR-28-39 (PBD-C8-Imidazole-MPB). This is exemplified in snapshots of MD simulations of KMR-28-39 (PBD-C8-Imidazole-MPB) (FIG. 1) and BPD-R7-Imidazole-MPB (FIG. 2) which illustrate identical hydrogen bonding interactions formed between each structure and a poly-G DNA sequence. Furthermore, molecular modelling results suggest that in the case of the C-ring linked PDD-R2-Pyrrole-Benzothiophene (FIG. 3), the interactivity of this particular molecule with DNA is governed by both non-covalent and H-bonding interactions.

TABLE 3

Free energy of binding (kcal/mol) of PBD-Imidazole-MPB and BPD-Imidazole-MPB over a 10ns simulation while docked in the sequence 5'-GGGGGGGGCC-3'.

| Structure | Free Energy of Binding (kcal/mol) in 5'-GGG̲GGGGGCC-3' (binding site underlined) |
|---|---|
| PBD-C8-MPB (KMR-28-39) 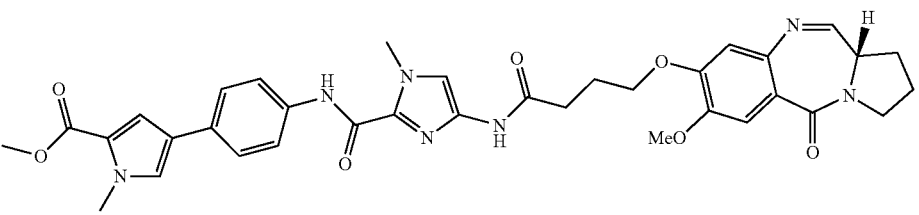 | −59.83 |
| BPD-R7-Im-MPB 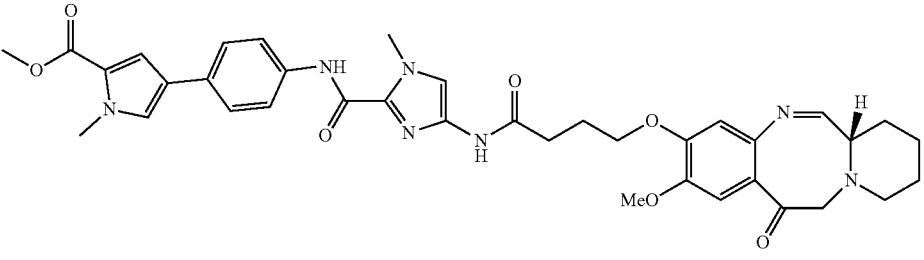 | −59.95 |
| PDD-R2-Pyrrole-Benzothiophene 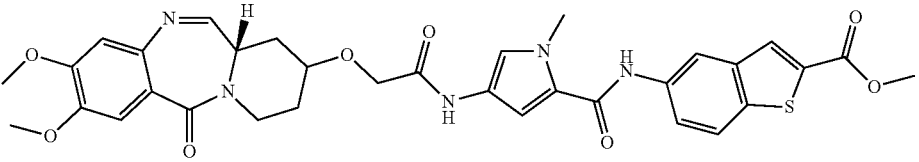 | −44.27 |

Figure 2:
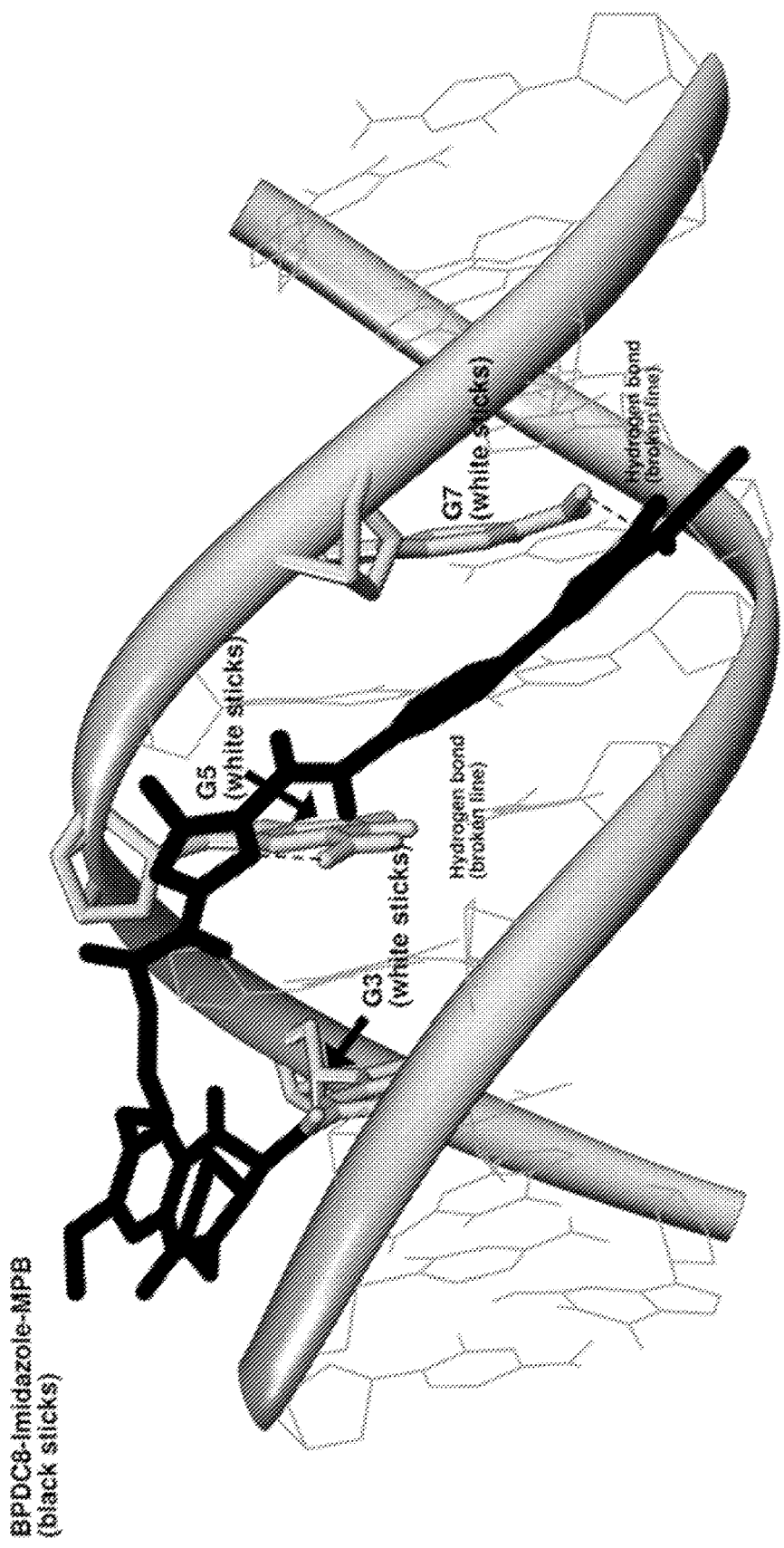
FIG. 2: Snapshot of MD simulation showing BPD-Imidazole-MPB interacting with 5'-GGGGGGGGCC-3
Figure 3:
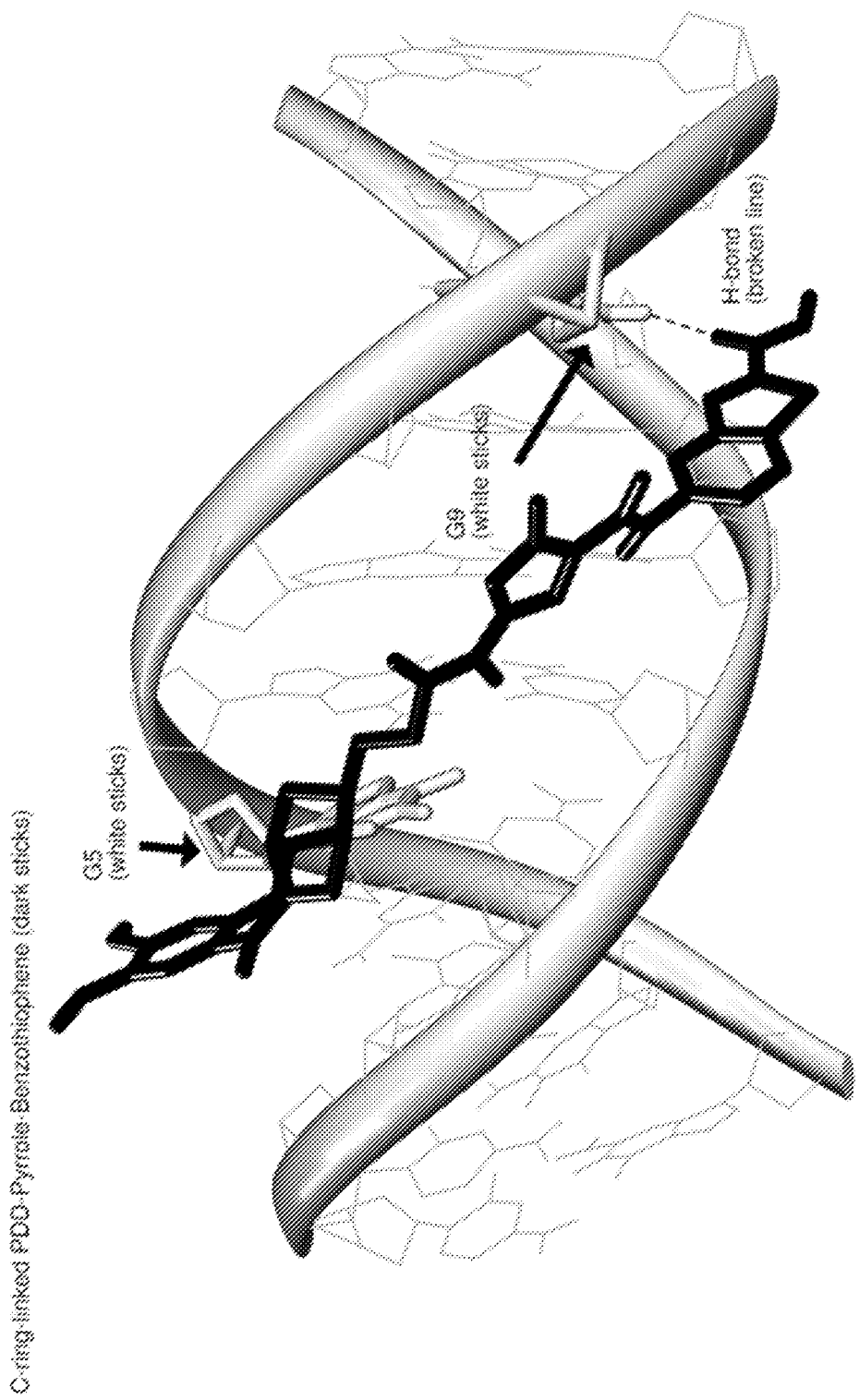
' and FIG. 3: Snapshot of MD simulation showing the PDD-R2-Pyrrole-Benzothiophene interacting with 5'-GGGGGGGGCC-3' where it can be seen (by a comparison with FIGS. 1 and 2) that it fits snugly in the DNA, assisted by the formation of sequence-specific hydrogen bonds and non-covalent interactions with the minor groove floor.

When modelled against the sequence 5'-GGGGGGGGCC-3' and covalently bound to G3 (underlined), hydrogen bonding interactions are formed between the imidazole nitrogen and G5, and between the terminal carbonyl and G7 in the case of both these structures: PBD-C8-Imidazole-MPB and BPD-R7-Imidazole-MPB (FIGS. 1 and 2). PDD-Pyrrole-Benzothiophene also forms strong interactions when bound to G5 of the sequence 5'-GGGGGGGGCC-3', where the Pyrrole-Benzothiophene moiety forms non-covalent interactions with the DNA minor groove, and the terminal ester of the benzothiophene group forms a sequence-selective H-bond with G9 of the DNA. As such, both BPD and PDD structures are expected to produce similarly high cytotoxicity to C8-linked PBD structures.

Furthermore, free energy of binding calculations (Table 3) show the potential of the new BPD and PDD conjugates to interact with DNA in a similar manner to KMR-28-39, with similar free energy of binding values observed for PBD, BPD and PDD monomeric conjugates.

Example 4

Synthesis of a PDD Scaffold

A suitable PDD scaffold 14 was prepared as shown in the following reaction scheme:

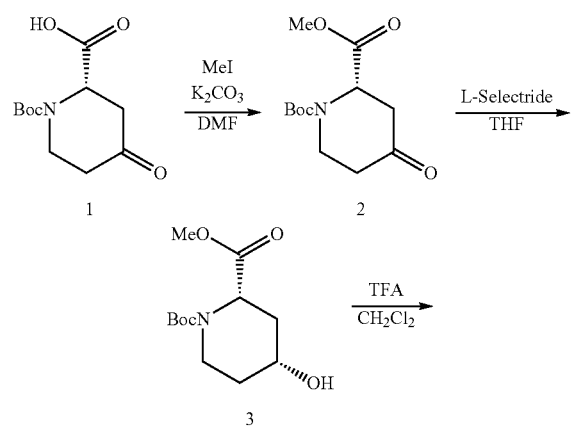

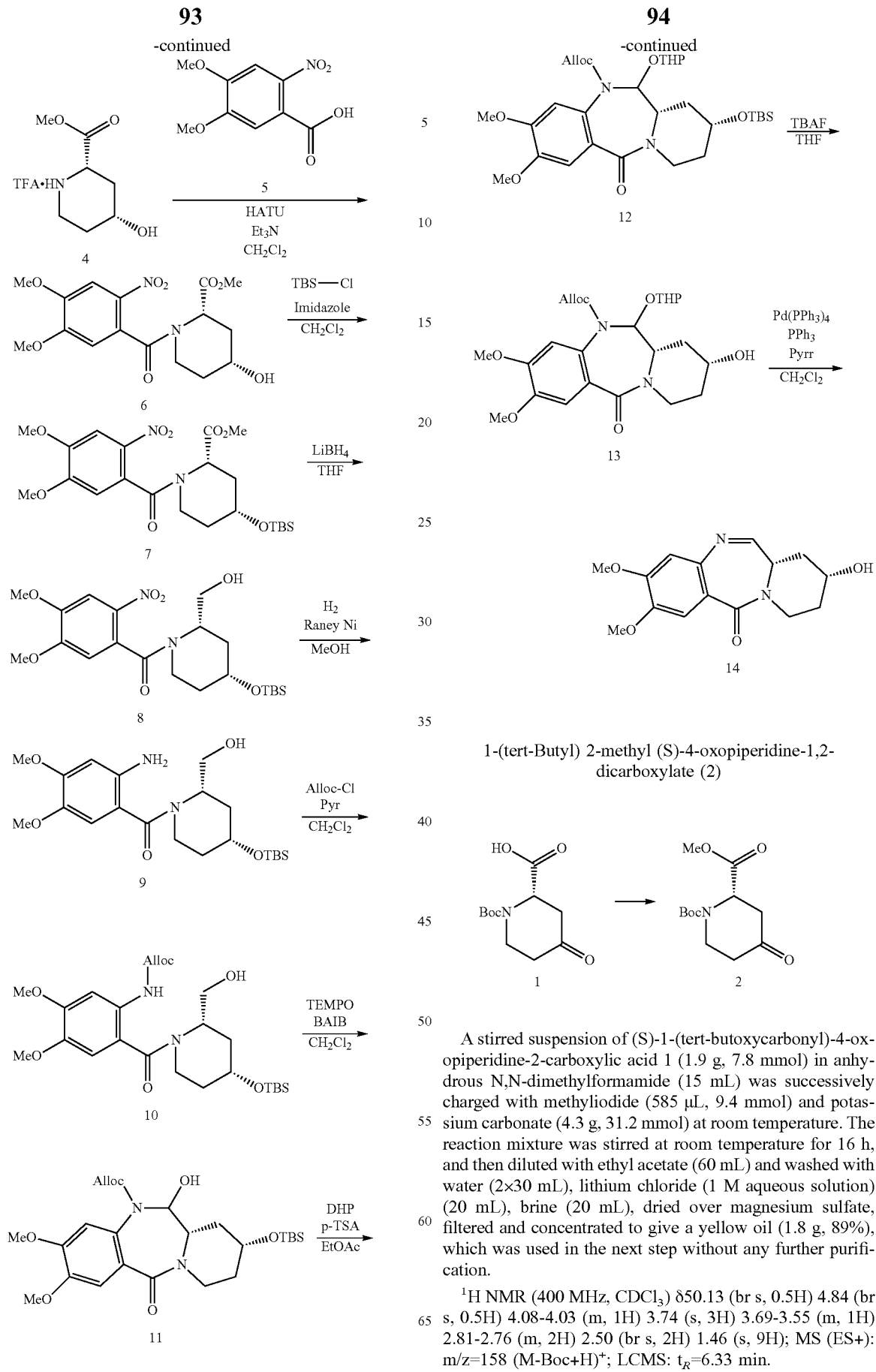

1-(tert-Butyl) 2-methyl (S)-4-oxopiperidine-1,2-dicarboxylate (2)

A stirred suspension of (S)-1-(tert-butoxycarbonyl)-4-oxopiperidine-2-carboxylic acid 1 (1.9 g, 7.8 mmol) in anhydrous N,N-dimethylformamide (15 mL) was successively charged with methyliodide (585 µL, 9.4 mmol) and potassium carbonate (4.3 g, 31.2 mmol) at room temperature. The reaction mixture was stirred at room temperature for 16 h, and then diluted with ethyl acetate (60 mL) and washed with water (2×30 mL), lithium chloride (1 M aqueous solution) (20 mL), brine (20 mL), dried over magnesium sulfate, filtered and concentrated to give a yellow oil (1.8 g, 89%), which was used in the next step without any further purification.

$^1$H NMR (400 MHz, CDCl$_3$) δ50.13 (br s, 0.5H) 4.84 (br s, 0.5H) 4.08-4.03 (m, 1H) 3.74 (s, 3H) 3.69-3.55 (m, 1H) 2.81-2.76 (m, 2H) 2.50 (br s, 2H) 1.46 (s, 9H); MS (ES+): m/z=158 (M-Boc+H)$^+$; LCMS: t$_R$=6.33 min.

1-(tert-Butyl) 2-methyl (2S,4R)-4-hydroxypiperidine-1,2-dicarboxylate (3)

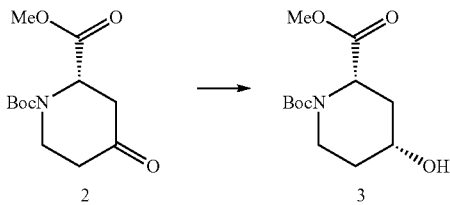 [SMILES: COC(=O)[C@@H]1CC(=O)CCN1C(=O)OC(C)(C)C ; COC(=O)[C@@H]1C[C@H](O)CCN1C(=O)OC(C)(C)C]

To a stirred solution of 1-(tert-butyl) 2-methyl (S)-4-oxopiperidine-1,2-dicarboxylate 2 (773 mg, 3 mmol) in anhydrous tetrahydrofuran (7 mL) was added L-selectride (1 M in tetrahydrofuran) (3.6 mL, 3.6 mmol) over 1 h at −78° C. and then stirred at 0° C. for 2.5 h. The reaction mixture was quenched with a saturated aqueouse solution of ammonium chloride (10 mL), diluted with ethyl acetate (15 mL) washed with water (10 mL), brine (10 mL), dried over magnesium sulfate, filtered and concentrated to give a yellow oil which was purified by column chromatography (silica), eluting with ethyl acetate/hexane (from 0% to 50%), to give the desired compound (492 mg, 63%) as a colourless oil.

$^1$H NMR (400 MHz, CDCl$_3$) δ 5.35 (br s, 1H) 5.03 (br s, 0.5H) 4.83 (br s, 0.5H) 4.67 (m, 1H) 3.89-3.77 (m, 1H) 3.74 (s, 3H) 3.69-3.59 (m, 1H) 2.21-2.87 (m, 2H) 2.52-2.39 (m, 1H) 1.97-1.82 (m, 1H) 1.47 (s, 9H); MS (ES+): m/z=160 (M-Boc+H)$^+$; LCMS: $t_R$=6.08 min.

Methyl (2S,4R)-4-hydroxypiperidine-2-carboxylate 2,2,2-trifluoroacetate (4)

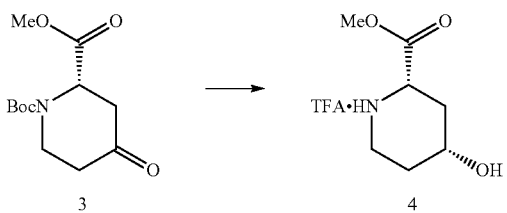

To a solution of 1-(tert-butyl) 2-methyl (2S,4R)-4-hydroxypiperidine-1,2-dicarboxylate 3 (310 mg, 1.2 mmol) in dichloromethane (10 mL) was added trifluoroacetic acid (1 mL) at 0° C. and the resulting mixture was stirred for 20 min and then concentrated. The amine was prepared and used immediately in the next step without any further purification MS (ES+): m/z=160 (M+H)$^+$; LCMS: $t_R$=2.00 mins.

Methyl (2S,4R)-1-(4,5-dimethoxy-2-nitrobenzoyl)-4-hydroxypiperidine-2-carboxylate (6)

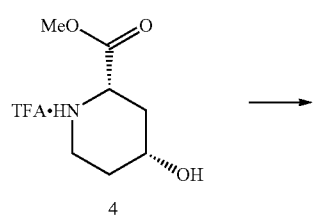

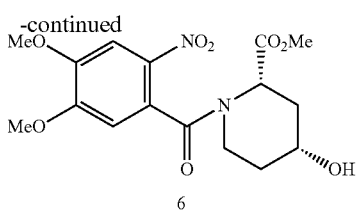

To a stirred solution of 4,5-dimethoxy-2-nitrobenzoic acid 5 (281 mg, 1.2 mmol) and trimethylamine (1.0 mL, 7.2 mmol) in dichloromethane (10 mL) was added O-(7-azabenzotriazole-1-yl)-N,N,N,N'-tetramethyluronium hexafluorophosphate (480 mg, 1.3 mmol) in one portion and the resulting mixture was stirred for 20 min at room temperature. A solution of methyl (2S,4R)-4-hydroxypiperidine-2-carboxylate 2,2,2-trifluoroacetate 4 (1.2 mmol) in dichloromethane (10 mL) was then added dropwise and the resulting mixture was stirred for 16 h at room temperature. The reaction was quenched with a saturated aqueous solution of sodium hydrogen carbonate (10 mL), the phases were separated and the aqueous layer was further extracted with dichloromethane (10 mL). The combined organics were washed with brine (10 mL), dried over magnesium sulfate, filtered and concentrated to give a brown oil. Purification was carried out by column chromatography (silica), eluting with ethyl acetate/hexane (from 0% to 100%), to give the desired compound (180 mg, 42%) as a colourless oil.

$^1$H NMR (400 MHz, CDCl$_3$) δ 7.72 (s, 1H) 6.87 (s, 1H) 5.56 (d, 1H, J=6.4 Hz) 4.73 (s, 1H) 4.25-4.23 (m, 1H) 4.00 (s, 3H) 3.99 (s, 3H) 3.80 (s, 3H) 3.57 (s, 1H) 3.14-3.10 (m, 1H) 2.57-2.54 (m, 1H) 2.18-2.13 (m, 1H) 1.72-1.67 (m, 1H) 1.64-1.61 (m, 1H); MS (ES+): m/z=369 (M+H)$^+$; LCMS: $t_R$=5.50 min.

Methyl (2S,4R)-4-((tert-butyldimethylsilyl)oxy)-1-(4,5-dimethoxy-2-nitro-benzoyl)piperidine-2-carboxylate (7)

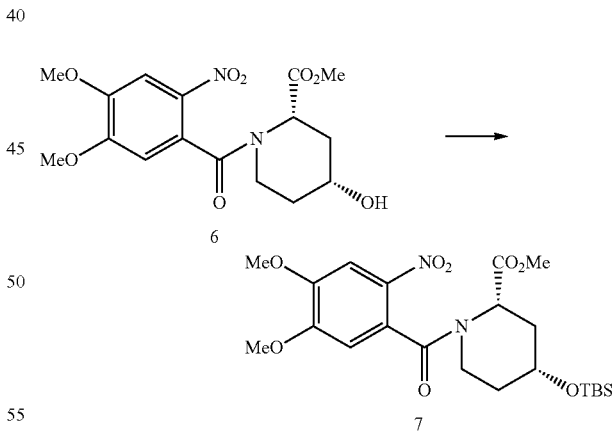

A mixture of methyl (2S,4R)-1-(4,5-dimethoxy-2-nitrobenzoyl)-4-hydroxypiperidine-2-carboxylate 6 (170 mg, 0.46 mmol), tert-butyldimethylsilyl chloride (83.5 mg, 0.55 mmol) and imidazole (79 mg, 0.55 mmol) in anhydrous dichloromethane (5 mL) was stirred at room temperature for 3 h. The reaction mixture was concentrated in vacuo and partitioned between diethyl ether (3×20 mL) and water (30 mL). The phases were separated, the organic layer was dried over magnesium sulfate, filtered and concentrated to give the title compound (176 mg, 79%) as a yellow oil. The resulting material was carried through to the subsequent step without any further purification.

¹H NMR (400 MHz, CDCl₃) δ 7.70 (s, 1H) 6.80 (s, 1H) 5.68-5.65 (m, 1H) 3.96 (s, 3H) 3.95 (s, 3H) 3.79 (s, 3H) 3.34-3.25 (m, 2H) 2.42-2.34 (m, 1H) 1.88-1.78 (m, 2H) 1.73-1.61 (m, 2H) 0.88 (s, 9H) 0.86 (s, 6H); MS (ES+): m/z=483 (M+H)⁺; LCMS: $t_R$=8.95 min.

((2S,4R)-4-((tert-Butyldimethylsilyl)oxy)-2-(hydroxymethyl)piperidin-1-yl)(4,5-dimethoxy-2-nitrophenyl)methanone (8)

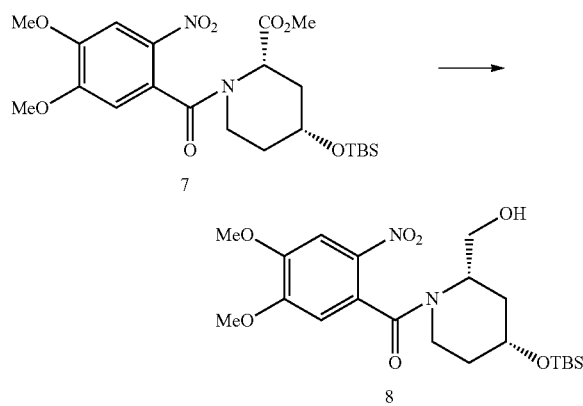

Lithium borohydride (2 M in tetrahydrofuran, 199 µL, 0.4 mmol) was added slowly to a solution of methyl (2S,4R)-4-((tert-butyldimethylsilyl)oxy)-1-(4,5-dimethoxy-2-nitrobenzoyl)piperidine-2-carboxylate 7 (128 mg, 0.26 mmol) in anhydrous tetrahydrofuran (3 mL) at 0° C. The reaction mixture was stirred at room temperature for 2 h. Water (5 mL) was then added carefully to the reaction mixture at 0° C. which was extracted with ethyl acetate (3×5 mL). The combined organic layers were dried over magnesium sulfate, filtered and concentrated to give the title compound (77 mg, 65%) as an orange oil that solidifies upon standing. The resulting material was carried through to the next step without any further purification.

¹H NMR (400 MHz, CDCl₃) δ 7.69 (s, 1H) 6.74 (s, 1H) 4.84 (br s, 1H) 3.97 (s, 3H) 3.95 (s, 3H) 3.94-3.77 (m, 4H) 3.31-3.10 (m, 2H) 1.78-1.49 (m, 4H) 1.24 (s, 9H) 0.87 (s, 6H); MS (ES+): m/z=455 (M+H)⁺; LCMS: $t_R$=8.15 min.

(2-Amino-4,5-dimethoxyphenyl)((2S,4R)-4-((tert-butyldimethylsilyl)oxy)-2-(hydroxymethyl)piperidin-1-yl)methanone (9)

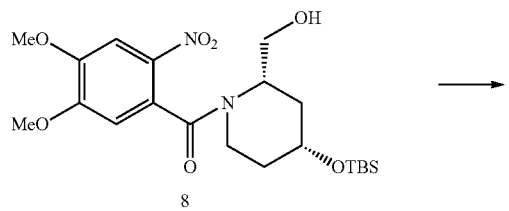

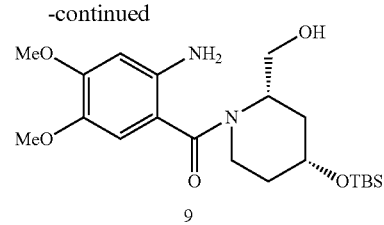

To a solution of ((2S,4R)-4-((tert-butyldimethylsilyl)oxy)-2-(hydroxymethyl)piperidin-1-yl)(4,5-dimethoxy-2-nitrophenyl)methanone 8 (106 mg, 0.23 mmol) in methanol (24 mL) was added Raney®-Nickel (slurry, in H₂O) (20 mg). The resulting mixture was hydrogenated at 35 psi for 1 h in a Parr apparatus, then filtered through a celite pad and concentrated in vacuo to give the title compound (87 mg, 90%) as a yellow solid. The resulting material was carried through to the next step without any further purification.

MS (ES+): m/z=425 (M+H)⁺; LCMS: $t_R$=7.48 min.

Allyl (2-((2S,4R)-4-((tert-butyldimethylsilyl)oxy)-2-(hydroxymethyl)-piperidine-1-carbonyl)-4,5-dimethoxyphenyl)carbamate (10)

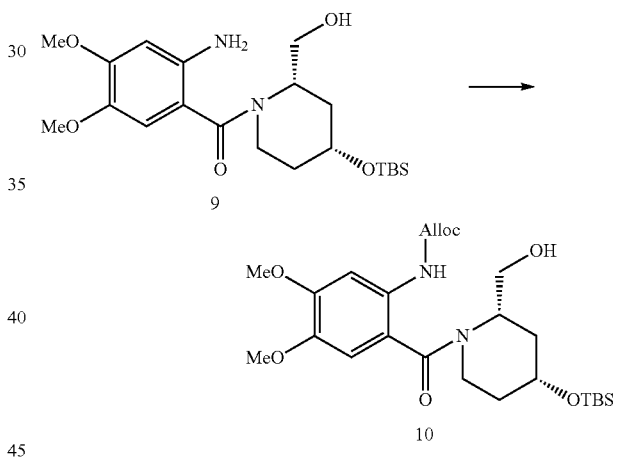

To a solution of (2-amino-4,5-dimethoxyphenyl)((2S,4R)-4-((tert-butyldimethyl-silyl)oxy)-2-(hydroxymethyl)piperidin-1-yl)methanone 9 (100 mg, 0.24 mmol) and pyridine (79 µL, 0.53 mmol) in anhydrous dichloromethane (4 mL) at −10° C., a solution of allylchloroformate (24 µL, 24 mmol) in dichloromethane (1 mL) was added dropwise. The resulting reaction mixture was stirred at room temperature for 0.5 h, quenched with a saturated aqueous solution of copper (II) sulfate (5 mL), diluted with dichloromethane and successively washed with water (10 mL), saturated aqueous solution of sodium bicarbonate (10 mL) and brine (10 mL). The organic layer was then dried over magnesium sulfate, filtered and concentrated to give the title compound (82 mg, 70%) as a pale yellow oil. The resulting material was carried through to the next step without any further purification.

¹H NMR (400 MHz, CDCl₃) δ 8.29 (br s, 1H) 7.63 (s, 1H) 6.75 (s, 1H) 5.97-5.88 (m, 2H) 5.36-5.20 (m, 1H) 4.61 (br s, 2H) 3.89 (s, 3H) 3.91 (s, 3H) 3.75-3.48 (m, 3H) 3.06 (br s, 1H) 1.89-1.74 (m, 2H) 1.69-1.53 (br s, 1H) 1.51-1.36 (m, 1H) 1.24 (m, 2H) 0.86 (s, 9H) 0.03 (s, 6H); MS (ES+): m/z=455 (M+H)⁺; LCMS: $t_R$=8.15 min.

Allyl (8R)-8-((tert-butyldimethylsilyl)oxy)-6-hydroxy-2,3-dimethoxy-12-oxo-6,6a,7,8,9,10-hexahydrobenzo[e]pyrido[1,2-a][1,4]diazepine-5(12H)-carboxylate (11)

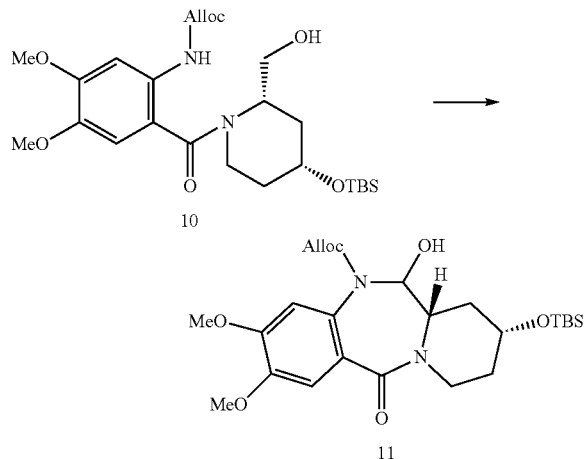

To a solution of allyl (2-((2S,4R)-4-((tert-butyldimethylsilyl)oxy)-2-(hydroxymethyl)-piperidine-1-carbonyl)-4,5-dimethoxyphenyl)carbamate 10 (82 mg, 0.16 mmol) in dichloromethane (4 mL) was added TEMPO (2.5 mg, 16 μmol) and (diacetoxyiodo)-benzene (62 mg, 0.19 mmol). The reaction mixture was stirred at room temperature for 16 h, and was then placed in an ice bath and quenched with a saturated aqueous solution of sodium metabisulfite (1 mL). The mixture was diluted dichloromethane (10 mL) and sequentially washed with saturated aqueous solution of sodium hydrogen carbonate (10 mL), water (10 mL) and brine (10 mL). The organic layer was then dried over magnesium sulfate, filtered and used in the next step without concentration or any further purification.

MS (ES+): m/z=507 (M+H)$^+$; LCMS: $t_R$=8.13 min.

Allyl (8R)-8-((tert-butyldimethylsilyl)oxy)-2,3-dimethoxy-12-oxo-6-((tetrahydro-2H-pyran-2-yl)oxy)-6,6a,7,8,9,10-hexahydrobenzo[e]-pyrido[1,2-a][1,4]diazepine-5(12H)-carboxylate (12)

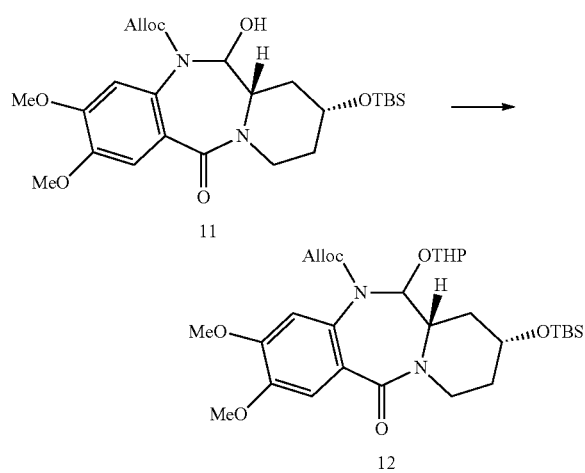

To the previously obtained solution containing allyl (8R)-8-((tert-butyldimethyl-silyl)oxy)-6-hydroxy-2,3-dimethoxy-12-oxo-6,6a,7,8,9,10-hexahydrobenzo[e]-pyrido[1,2-a][1,4]diazepine-5(12H)-carboxylate 11 in dichloromethane were added 3,4-dihydro-2H-pyran (146 μL, 1.6 mmol) and pTSA (0.8 mg, 1% w/w), and the resultant was stirred at room temperature for 16 h. The reaction mixture was then diluted with dichloromethane (5 mL) and washed with saturated aqueous solution of sodium hydrogen carbonate (5 mL) and brine (5 mL). The organic layer was dried over magnesium sulfate, filtered and concentrated to give the desired compound (66 mg, 70% over two steps) as a yellow oil. The resulting material was carried through to the next step without any further purification.

Data shown for the major isomer. MS (ES+): m/z=591 (M+H)$^+$; LCMS: $t_R$=9.85 min.

Allyl (8R)-8-hydroxy-2,3-dimethoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (13)

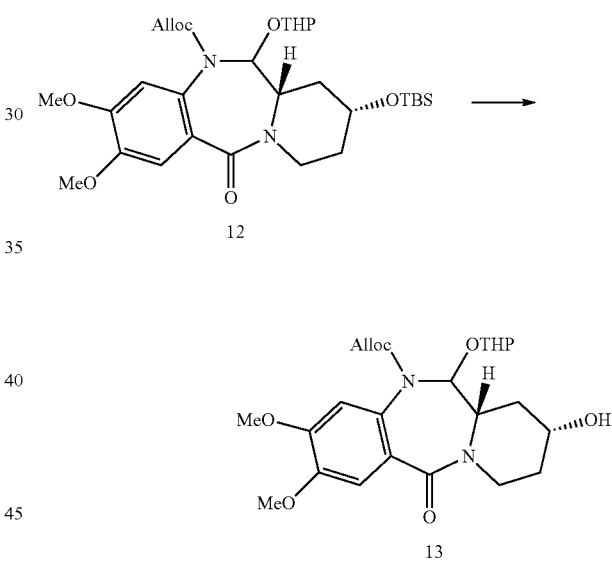

To solution of allyl (8R)-8-((tert-butyldimethylsilyl)oxy)-2,3-dimethoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate 12 (66 mg, 0.11 mmol) in anhydrous dichloromethane (1 mL) at 0° C. was added tetrabutylammonium fluoride (1 M in tetrahydrofuran) (170 μL, 0.17 mmol). The reaction mixture was stirred at room temperature for 1 h. The reaction mixture was concentrated in vacuo and the residue was diluted with water (5 mL) and extracted with ethyl acetate (3×5 mL). The organic layer was then washed with brine (5 mL), dried over magnesium sulfate, filtered and concentrated to give the desired compound (49 mg, 93%) as a yellow oil.

MS (ES+): m/z=477 (M+H)$^+$; LCMS: $t_R$=7.85 min.

(8R)-8-hydroxy-2,3-dimethoxy-7,8,9,10-tetrahydrobenzo[e]pyrido[1,2-a][1,4]diazepin-12(6aH)-one (14)

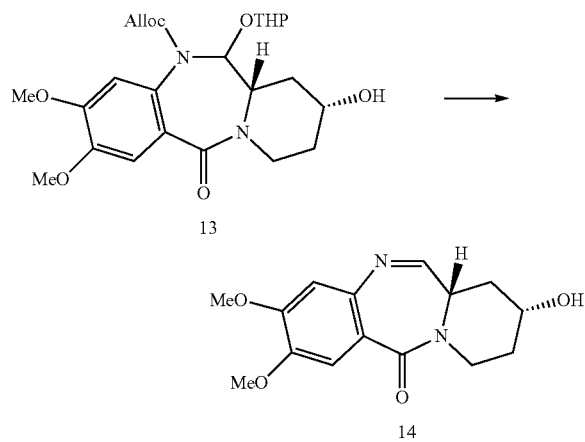

To a solution of allyl (8R)-8-hydroxy-2,3-dimethoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate 13 (27 mg, 0.057 mmol) in dichloromethane (2 mL) were successively added polymer-bound tetrakis(triphenylphosphine)palladium(0) (12 mg), polymer-bound triphenylphosphine (100 mg) and pyrrolidine (7 μL, 0.09 mmol). The reaction mixture was stirred at room temperature for 1.5 h, filtered through a pad of celite and the volatiles were removed in vacuo. The resulting residue was then purified by column chromatography (silica), eluting with acetone/dichloromethane (from 0% to 5%), to give the desired compound (11.0 mg, 66%) as a pale yellow oil $^1$H NMR (400 MHz, CDCl$_3$) δ 7.93 (d, J=5.9 Hz, 1H) 7.43 (s, 1H) 6.79 (s, 1H) 4.58 (br s, 1H) 4.46-4.40 (m, 1H) 4.32-4.25 (1H) 3.97 (s, 3H) 3.93 (m, 3H) 3.91-3.81 (m, 2H) 3.29-3.20 (m, 1H) 2.38-2.32 (m, 1H) 2.04-1.96 (m, 2H); MS (ES+): m/z=291 (M+H)$^+$; LCMS: $t_R$=4.47 min.

Example 5

Synthesis of a C-Ring Linked Dimer

Commercially available (S)-1-Boc-4-oxopiperidine-2-carboxylic acid 1 (Sigma-Aldrich) will be converted into the C-ring alcohol containing compound 13 as described above in Example 4. Reaction of the alcohol compound 13 with 1,3-propanediol di-p-tosylate will give the protected C-ring linked dimeric compound 15. Simultaneous removal of the nitrogen and the oxygen protecting groups will give the imine dimer 16 (7, 71, 72).

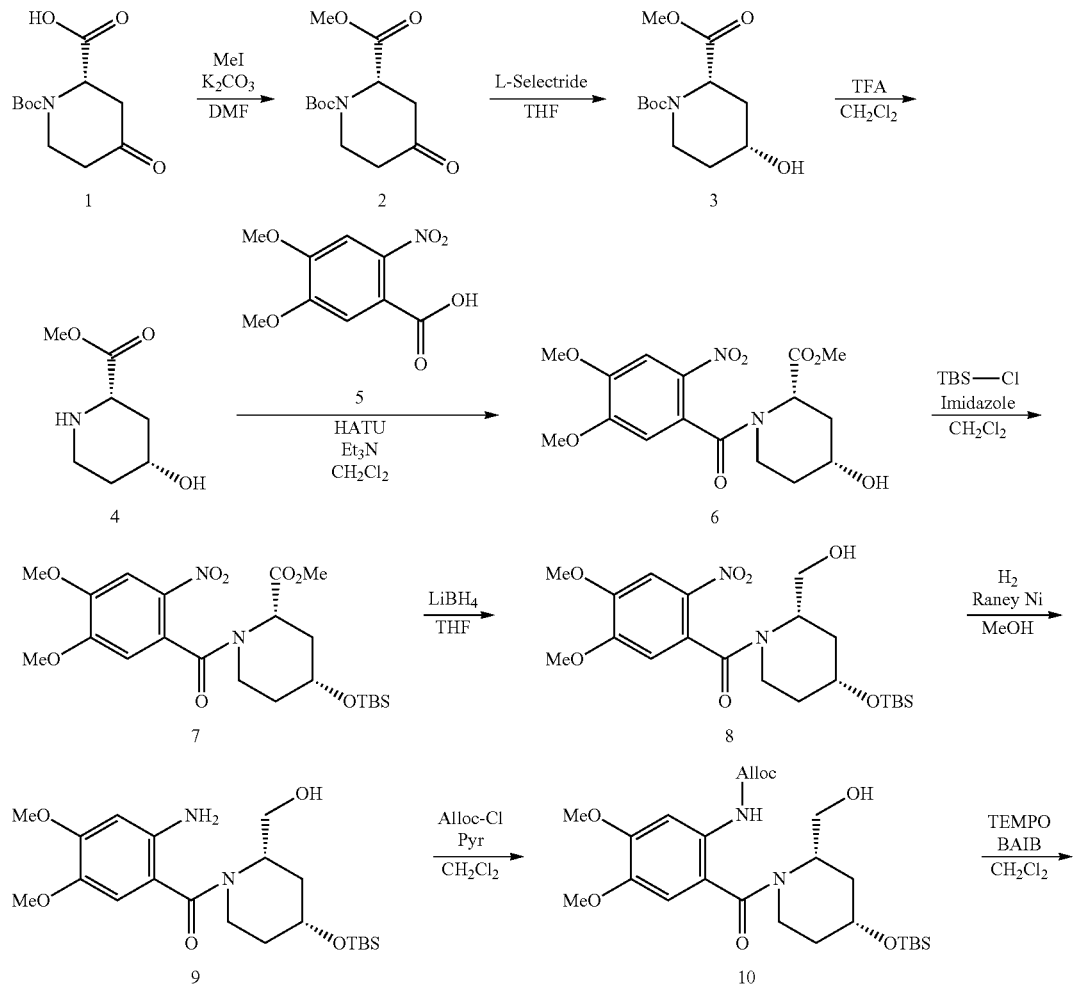

-continued

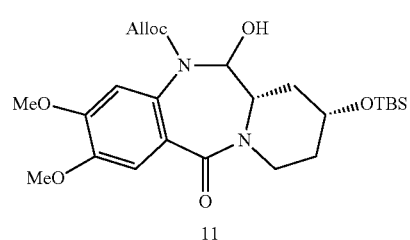 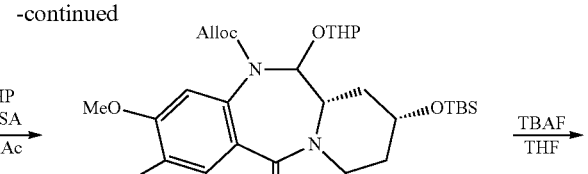

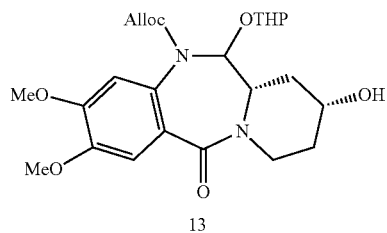

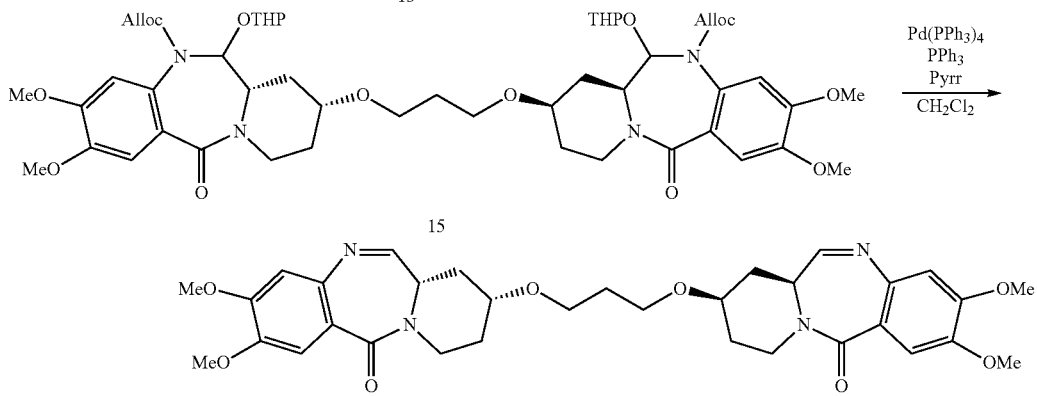

Example 6

Synthesis of an Aromatic Side Chain Precursor 19

Methyl 5-(4-((tert-butoxycarbonyl)amino)-1-methyl-1H-pyrrole-2-carboxamido)benzo[b]thiophene-2-carboxylate (18)

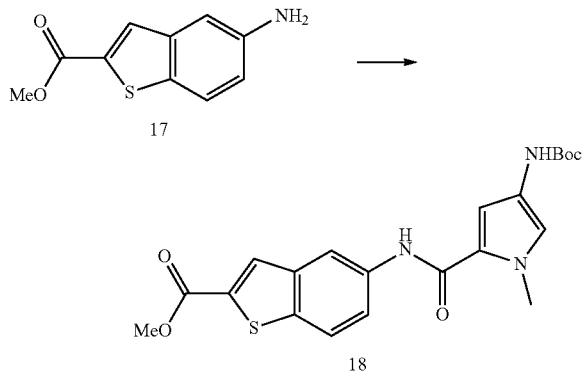

A solution of 4-((tert-butoxycarbonyl)amino)-1-methyl-1H-pyrrole-2-carboxylic acid (500 mg, 2.1 mmol) in N,N-dimethylformamide (10 mL) was charged with 1-(3-dimethylaminopropyl)-3-ethylcarbodiimide hydrochloride (725 mg, 3.8 mmol) and 4-(dimethylamino)pyridine (577 mg, 4.7 mmol). The reaction mixture was stirred at room temperature for 2 h. Methyl 5-aminobenzo[b]thiophene-2-carboxylate 17 (392 mg, 1.9 mmol) was then added and the resulting mixture was stirred at room temperature for 16 h. This was then poured into ice-water (20 mL) and extracted with ethyl acetate (3×50 mL). The combined organic extracts were sequentially washed with 1 M citric acid (30 mL), a saturated aqueous solution of sodium hydrogen carbonate (35 mL), water (35 mL) and brine (35 mL). The organic layer was then dried over sodium sulfate, filtered and concentrated. The resulting residue was purified by column chromatography (silica), eluting with ethyl acetate/hexane (from 0% to 50%), to give the title compound 18 (610 mg, 75%) as a beige solid.

MS (ES+): m/z=430 (M+H)$^+$; LCMS: $t_R$=7.90 min.

Methyl 5-(4-amino-1-methyl-1H-pyrrole-2-carboxamido)benzo[b]-thiophene-2-carboxylate hydrochloride (19)

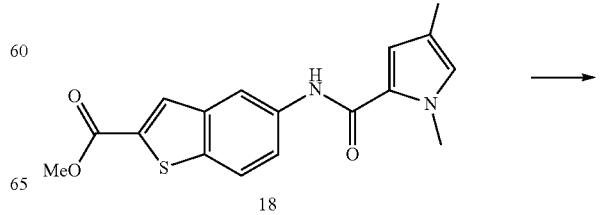

-continued

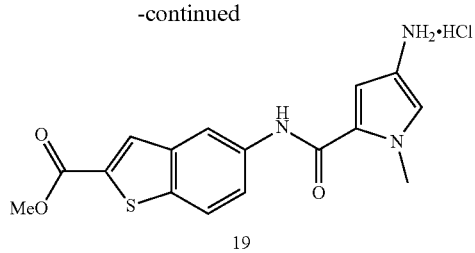

19

Methyl 5-(4-((tert-butoxycarbonyl)amino)-1-methyl-1H-pyrrole-2-carboxamido)-benzo[b]thiophene-2-carboxylate 18 (610 mg, 1.4 mmol) was dissolved in hydrochloric acid (4 M in dioxane) (3.6 mL) and the reaction mixture was stirred at room temperature for 2 h. The reaction mixture was concentrated in vacuo to give the title compound 19 (600 mg, 99%) as a brown solid. The product was carried through to the next step without any further purification.

MS (ES+): m/z=330 (M+H)$^+$; LCMS: $t_R$=5.52 min.

Example 7

Synthesis of a C-Ring Linked Monomeric Conjugate

A monomeric compound 23 will be prepared by the following reaction scheme.

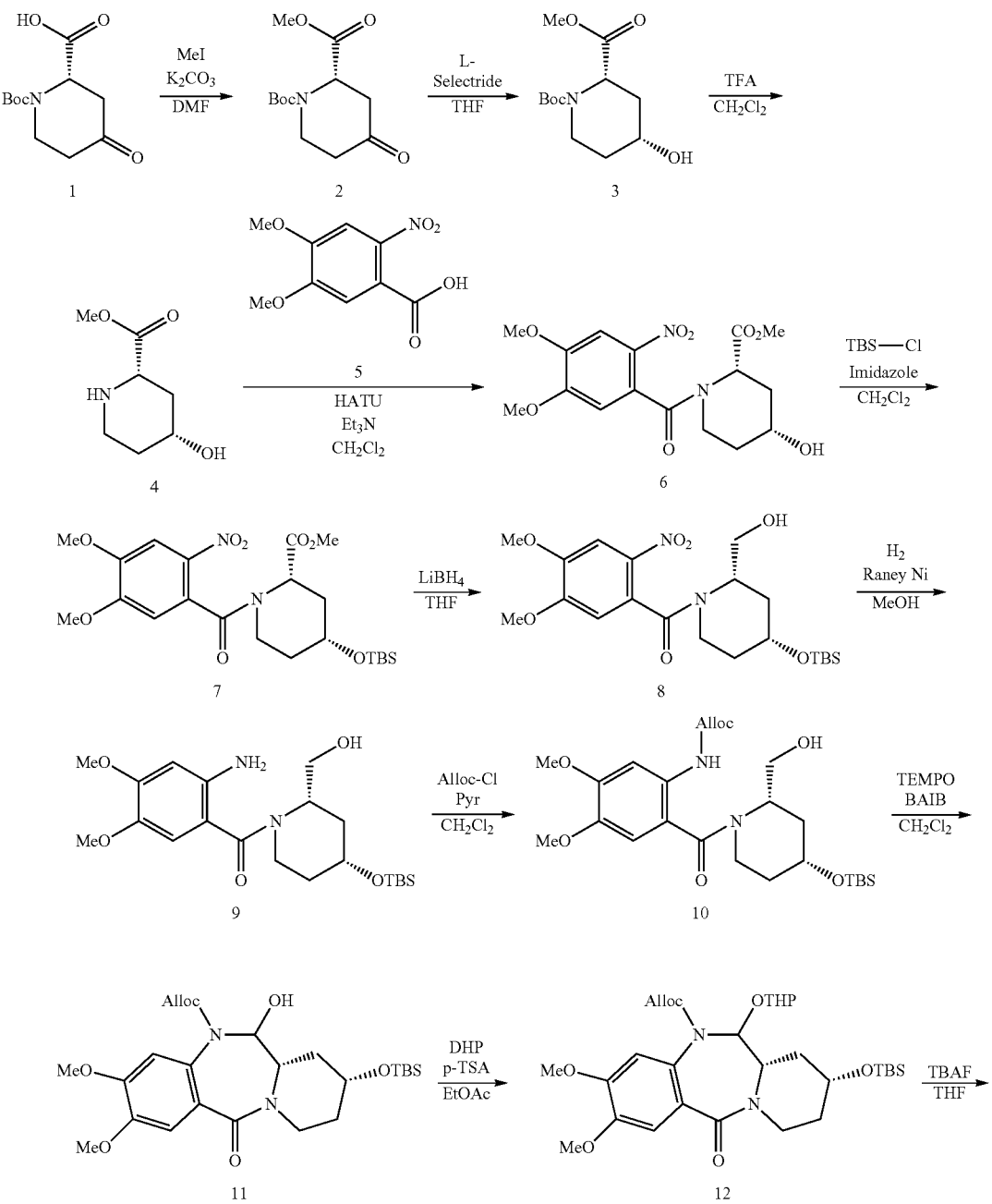

107

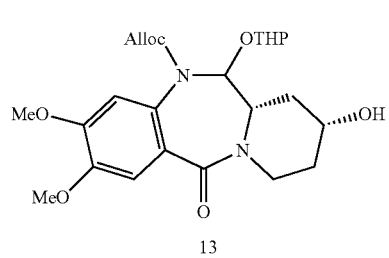

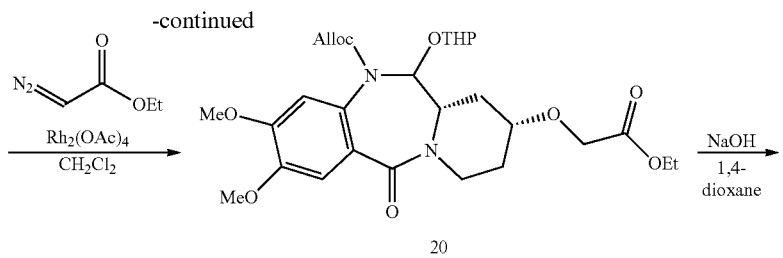

-continued

13

20

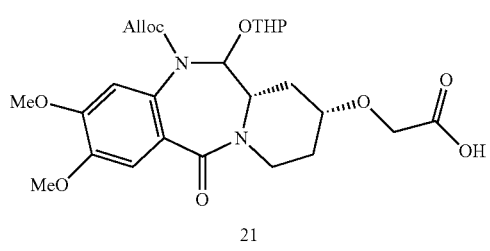

21

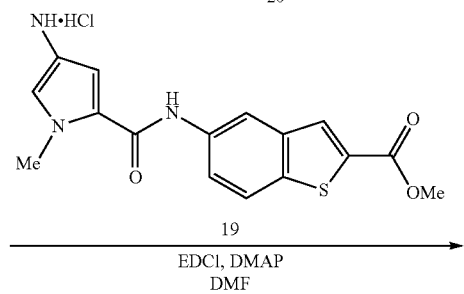

19

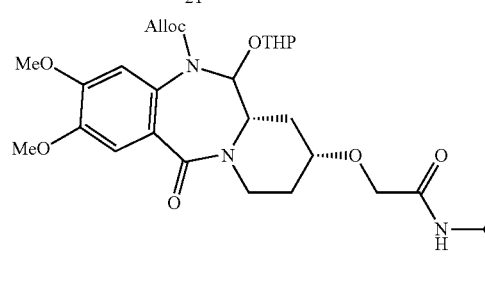

22

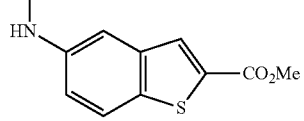

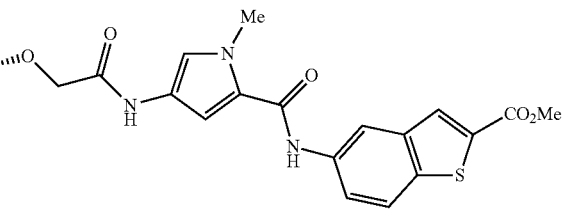

23

Commercially available (S)-1-Boc-4-oxopiperidine-2-carboxylic acid 1 (Sigma-Aldrich) will be converted into the C-ring alcohol containing compound 13 as described above in Example 4. Reaction of the alcohol compound 13 in a rhodium acetate catalysed reaction with ethyl diazoacetate will give the coupled compound 20. Hydrolysis of the terminal ester group of 20 catalysed by sodium hydroxide base gives the carboxylic acid compound 21. The carboxylic acid 21 will be coupled (77, 78) with a suitable aromatic side chain precursor 19 containing a heterocyclic amine, prepared as described above in Example 6, in a peptide coupling reaction (22-26, 77, 78) using EDCI, DMAP and DMF to give the protected compound 22. Simultaneous removal of the nitrogen and the oxygen protecting groups in a palladium catalysed de-protection reaction will give the imine 23 (71, 72, 78).

108

Allyl (6aS,8R)-8-(2-ethoxy-2-oxoethoxy)-2,3-dimethoxy-12-oxo-6-((tetra-hydro-2H-pyran-2-yl)oxy)-6,6a,7,8,9,10-hexahydrobenzo[e]pyrido[1,2-a][1,4]diazepine-5(12H)-carboxylate (20)

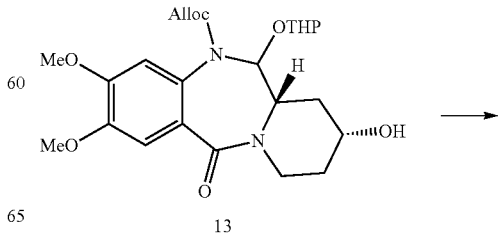

13

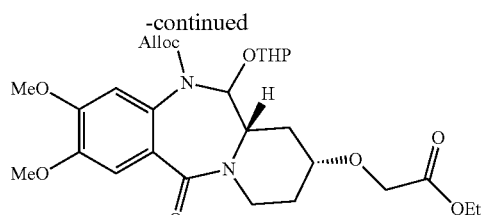

To a solution of allyl (6aS,8R)-8-hydroxy-2,3-dimethoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (13) (79 mg, 0.17 mmol) in anhydrous dichloromethane (3 mL) was added rhodium(II) acetate dimer (7.5 mg, 0.017 mmol) and ethyl diazoacetate (220 mL, 1.66 mmol). The reaction mixture was stirred at room temperature for 16 h. The reaction mixture was diluted with diethyl ether (30 mL) and filtered through celite. The filter cake was then washed with diethyl ether. The filtrate was concentrated in vacuo and the resulting residue was then purified by column chromatography (silica), eluting with dichloromethane/methanol (from 0% to 5%), to give the title compound (117 mg) as a brown oil. The resulting material was used in the subsequent step without further purification.

MS (ES+): m/z=563.2 (M+H)$^+$; LCMS: $t_R$=3.82 min.

2-((((6aS,8R)-5-((Allyloxy)carbonyl)-2,3-dimethoxy-12-oxo-6-((tetrahydro-2H-pyran-2-yl)oxy)-5,6,6a,7,8,9,10,12-octahydrobenzo[e]pyrido[1,2-a][1,4]diazepin-8-yl)oxy)acetic acid (21)

To a solution of allyl (6aS,8R)-8-(2-ethoxy-2-oxoethoxy)-2,3-dimethoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (20) (117 mg, 0.21 mmol) in 1,4-dioxane (2.5 mL) was added a 0.5 M aqueous solution of sodium hydroxide (2.5 mL, 1.25 mmol). The reaction mixture was stirred at room temperature for 1 h and was then concentrated in vacuo, after which water (20 mL) was added and the aqueous layer was acidified to pH=1 with a 1 M citric acid solution (5 mL). The aqueous layer was then extracted with ethyl acetate (2×50 mL) and the combined organic extracts washed with brine (50 mL), dried over sodium sulfate, filtered and concentrated to give the impure title compound (53 mg, 28%) as a brown oil. The product was carried through to the next step without further purification.

MS (ES+): m/z=535.1 (M+H)$^+$; LCMS: $t_R$=3.25 min.

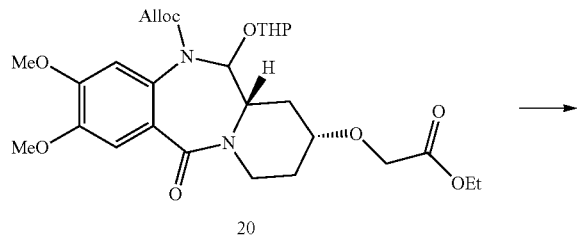

Allyl (6aS,8R)-2,3-dimethoxy-8-(2-((5-((2-(methoxycarbonyl)benzo[b]thio-phen-5-yl)carbamoyl)-1-methyl-1H-pyrrol-3-yl)amino)-2-oxoethoxy)-12-oxo-6-((tetrahydro-2H-pyran-2-yl)oxy)-6,6a,7,8,9,10-hexahydrobenzo[e]-pyrido[1,2-a][1,4]diazepine-5(12H)-carboxylate (22)

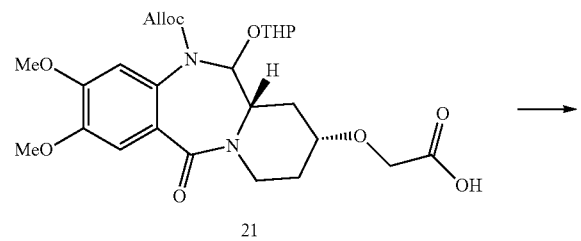

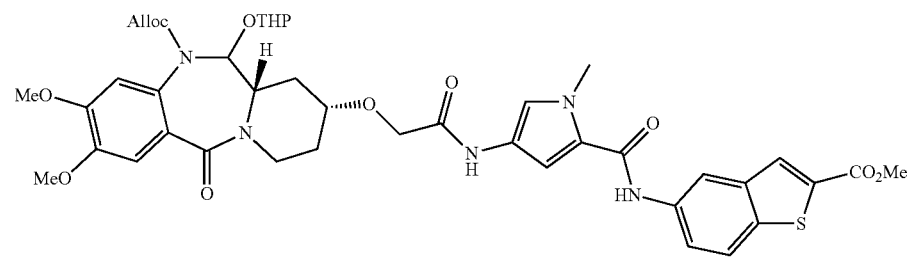

A solution of 2-((((6aS,8R)-5-((allyloxy)carbonyl)-2,3-dimethoxy-12-oxo-6-((tetra-hydro-2H-pyran-2-yl)oxy)-5,6,6a,7,8,9,10,12-octahydrobenzo[e]pyrido[1,2-a][1,4]-diazepin-8-yl)oxy)acetic acid (21) (53 mg, 0.0674 mmol) in N,N-dimethylformamide (1 mL) was charged with 1-(3-dimethylaminopropyl)-3-ethylcarbodiimide hydrochloride (26 mg, 0.136 mmol) and 4-(dimethylamino)pyridine (21 mg, 0.172 mmol). The reaction mixture was stirred at room temperature for 3 h. Methyl 5-(4-amino-1-methyl-1H-pyrrole-2-carboxamido)benzo[b]thiophene-2-carboxylate hydrochloride (16) (25 mg, 0.0674 mmol) was then added and the resulting mixture was stirred at room temperature for 16 h. This was then poured into ice-water (20 mL) and extracted with ethyl acetate (3×50 mL). The combined organic extracts were sequentially washed with 1 M citric acid (30 mL), a saturated aqueous solution of sodium hydrogen carbonate (35 mL), water (35 mL) and brine (35 mL). The organic layer was then dried over sodium sulfate, filtered and concentrated in vacuo to give the title compound (70 mg, 82%) as a yellow oil. The product was carried through to the next step without further purification.

MS (ES+): m/z=868.3 (M+Na)$^+$; LCMS: $t_R$=4.08 min.

Methyl 5-(4-(2-((((6aS,8R)-2,3-dim ethoxy-12-oxo-6a,7,8,9,10,12-hexahydrobenzo[e]pyrido[1,2-a][1,4]diazepin-8-yl)oxy)acetamido)-1-methyl-1H-pyrrole-2-carboxamido)benzo[b]thiophene-2-carboxylate (23)

by column chromatography (silica), eluting with acetone/dichloromethane (from 0% to 100%), to give the title compound (5.3 mg, 12%) as a brown gum.

$^1$H NMR (CDCl$_3$, 400 MHz) δ 8.30 (d, J=1.9 Hz, 1H), 8.12 (S, J=5.7 Hz, 1H), 8.10 (br s, 1H), 8.01 (s, 1H), 7.89 (br s, 1H), 7.82 (s, 1H), 7.79 (s, 1H), 7.54 (dd, J=8.9, 1.6 Hz, 1H), 7.44 (s, 1H), 7.23 (s, 1H), 6.82 (s, 1H), 6.80 (s, 1H), 3.98 (s, 3H), 3.95 (s, 6H), 3.93 (br s, 3H), 3.38-3.44 (m, 2H), 2.98-3.03 (m, 1H), 2.64 (s, 2H), 2.29-2.36 (m, 2H), 1.88 (d, J=6.5 Hz, 2H); $^{13}$C NMR (100 MHz, CDCl$_3$) δ 210.9, 163.2, 160.3, 159.6, 146.0, 139.3, 137.8, 130.5, 123.1, 115.9, 112.1, 108.9, 104.1, 69.5, 56.2, 53.8, 52.5, 44.3, 36.9, 36.5, 31.9, 31.7, 29.7, 29.3, 19.3, 18.7, 12.4; MS (ES+): m/z=660.2 (M+H)$^+$; LCMS: $t_R$=6.83 min.

Example 8

Synthesis of an Aromatic Side Chain Precursor 25

Methyl 5-(4-amino-1-methyl-1H-imidazole-2-carboxamido)benzo[b]thiophene-2-carboxylate hydrochloride 25 will be prepared by corresponding steps to those used for the corresponding pyrrole compound 19 as detailed in Example 6 above. Hence, methyl 5-aminobenzo[b]thiophene-2-carboxylate 17 and 4-((tert-butoxycarbonyl)-amino)-1-methyl-1H-pyrrole-2-carboxylic acid will be coupled using EDCI, DMAP peptide coupling conditions to give 24. Acid catalysed removal of the Boc protecting group will then provide

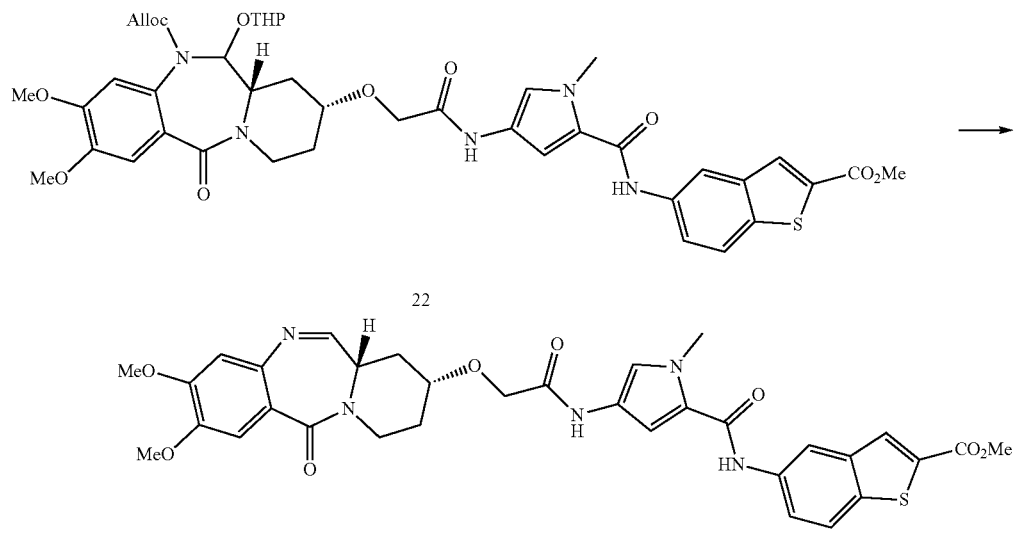

To a solution of allyl (6aS,8R)-2,3-dimethoxy-8-(2-((5-((2-(methoxycarbonyl)-benzo[b]thiophen-5-yl)carbamoyl)-1-methyl-1H-pyrrol-3-yl)amino)-2-oxoethoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (22) (70 mg, 0.0554 mmol) in dichloromethane (2 mL) was added tetrakis(triphenylphosphine)palladium(0) (3 mg, 5 mol %), triphenylphosphine (3.5 mg, 25 mol %) and pyrrolidine (5.5 mL, 0.067 mmol). The reaction mixture was stirred at room temperature for 16 h and then subjected to high vacuum for 30 min until excess pyrrolidine was thoroughly removed. The resulting residue was then purified the target aromatic side chain precursor 25 as shown in the reaction scheme below.

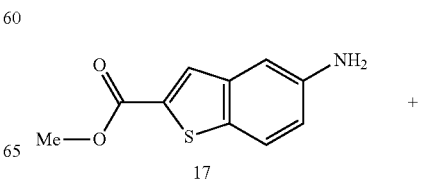

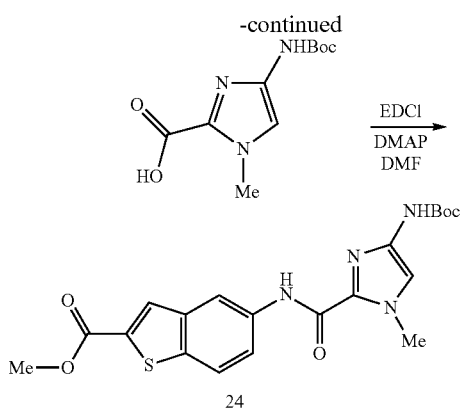
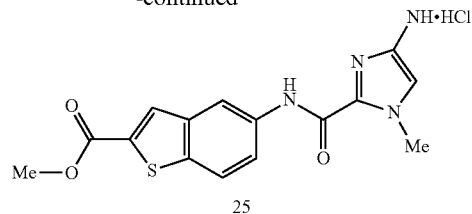
Example 9
Synthesis of a C-Ring Linked Monomeric Conjugate
A monomeric compound 27 will be prepared by the following reaction scheme.
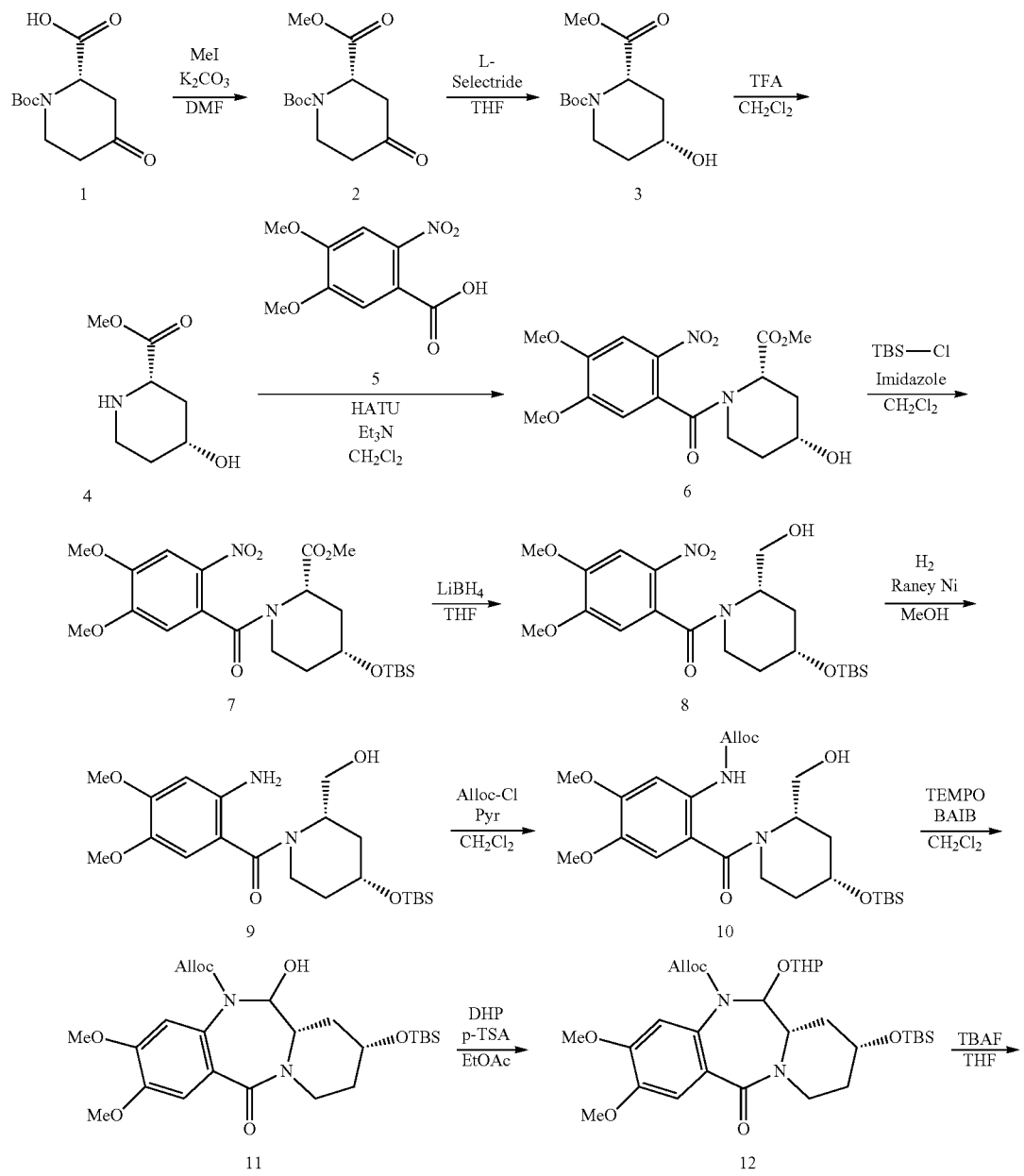

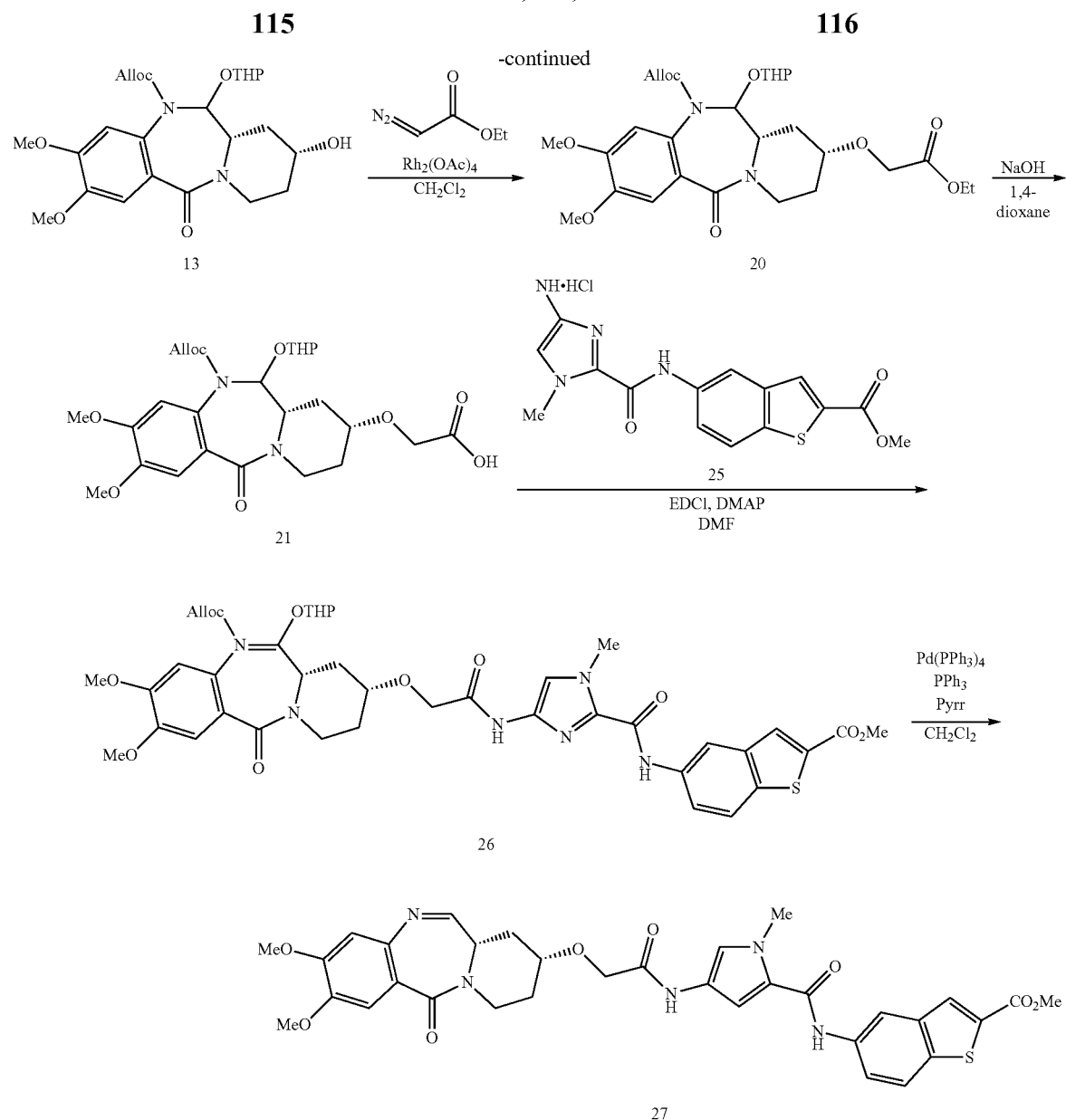

Commercially available (S)-1-Boc-4-oxopiperidine-2-carboxylic acid 1 (Sigma-Aldrich) will be converted into the C-ring alcohol containing compound 13 as described above in Example 4. Reaction of the alcohol compound 13 in a rhodium acetate catalysed reaction with ethyl diazoacetate will give the coupled compound 20. Hydrolysis of the terminal ester group of 20 catalysed by sodium hydroxide base gives the carboxylic acid compound 21. The carboxylic acid 21 will be coupled (77, 78) with a suitable aromatic side chain precursor 27 containing a heterocyclic amine, prepared as described above in Example 8, (22-26, 77, 78), in a peptide coupling reaction using EDCI, DMAP and DMF to give the protected compound 26. Simultaneous removal of the nitrogen and the oxygen protecting groups in a palladium catalysed de-protection reaction will give the imine 27 (71, 72, 78).

Example 10

Synthesis of C-Ring Precursor

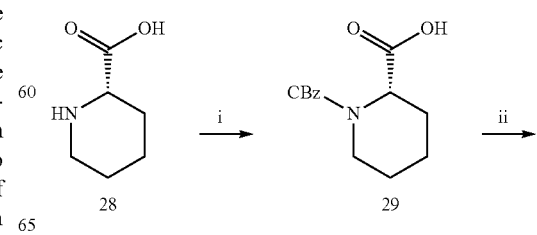

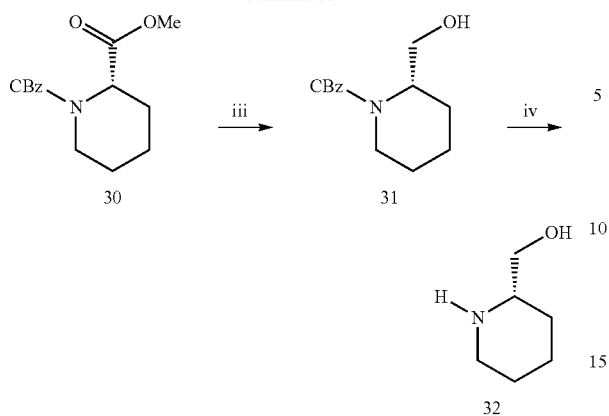

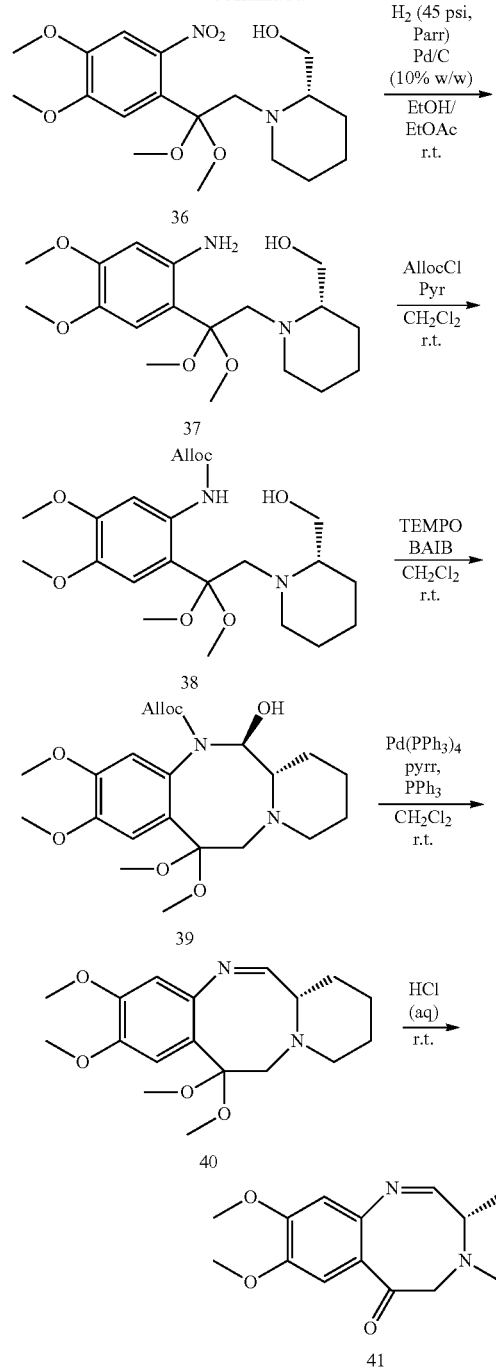

The C-ring precursor 32 may be prepared as shown in the reaction scheme above. The commercially available (S)-(−)-2-Piperidinecarboxylic acid (Sigma-Aldrich) will be N-protected as the benzyl carbamate 28 (71, 72) and the carboxylic acid group will be converted to the ester 29 and will then reduced to the alcohol 30 (30). This alcohol 30 may then have the N-Cbz group removed by catalytic hydrogenation to furnish the alkanolamine 32 (71, 72). The following reagents and conditions may be used in the reaction scheme above.

Reagents and Conditions:

(i) CBzCl, NaHCO$_3$, Et$_2$O; (ii) MeOH, H$_2$SO$_4$, Reflux; (iii) LiBH$_4$, THF, 0° C.; (iv) 10% Pd/C, H$_2$, EtOH.

Example 11

Synthesis of a BPD Scaffold

A suitable BPD scaffold 41 may be prepared by the reaction scheme shown below.

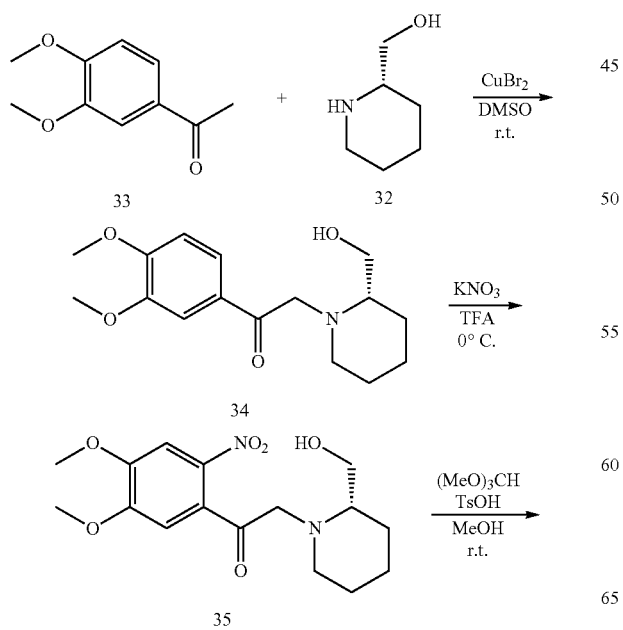

Commercially available 3',4'-Dimethoxyacetophenone 33 (Sigma-Aldrich) will be reacted with S-2-piperidinemethanol 32 (from Example 10) in a copper(II) carbonyl-amine coupling reaction to provide the product 34 (80). The aromatic ring of 34 will then undergo aromatic nitration to produce the nitro compound 35. The carbonyl group of compound 35 will then be protected as the ketal 36 by reacting with trimethyl orthoformate (72, 73). Palladium-carbon catalysed reduction of the nitro group of ketal 36 will then produce the aniline derivative 37 (27). The amine group of 37 will then be protected with an alloc protecting group (72, 73) to give compound 38. The B-ring of compound 39 will be formed by an oxidative cyclisation using TEMPO and BAIB as oxidising agents (75, 76). Removal of the oxygen protecting groups will give the imine (7, 72, 73, 77). Treatment with acid will remove the ketal to provide the PBC scaffold compound 41.

Example 12

A dimeric compound 47 is prepared by reacting the C-ring precursor 32 from Example 10 in the reaction scheme shown below. Commercially available 3',4'-Dimethoxyacetophenone 33 (Sigma-Aldrich) will be converted into the ketal 36 as described above in Example 11. Reaction of ketal 36 with 1,3-diiodoproane in the presence of aqueous potassium carbonate and DMF will give the dimeric nitro compound 42. The nitro groups of 42 will be reduced to amine groups to give the aniline derivative 43 via palladium catalyzed reduction (27). The aniline derivative 43 will be treated with allyl chloroformate in the presence of pyridine to give the Alloc protected compound 44 (72, 73). The ring cyclisation is carried out using a TEMPO/BAIB system (75, 76) to afford the protected cyclised dimer 45. Treatment of the Alloc protected PBC precursors 45 with Pd(PPh3)$_4$ in the presence of pyrrolidine removes the Alloc protecting group to produce dimer compound 46 (7, 72, 73, 77). Finally, treatment with acid will remove the ketal protecting groups to provide the PBC dimer 47.

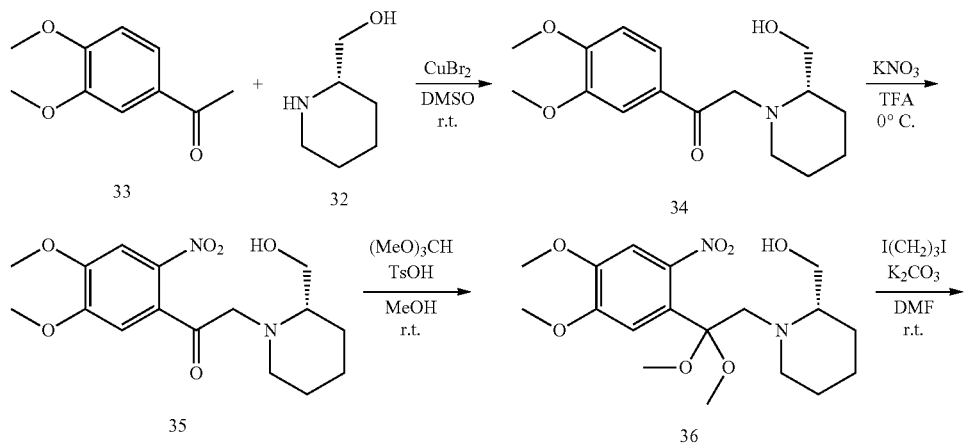

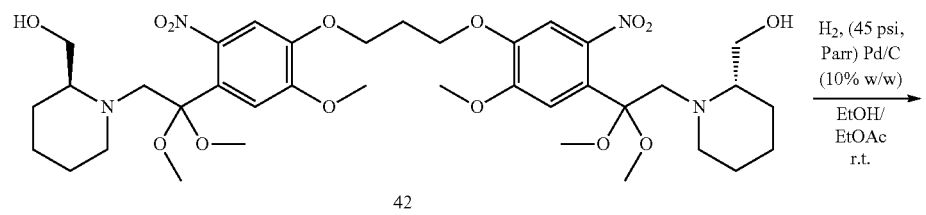

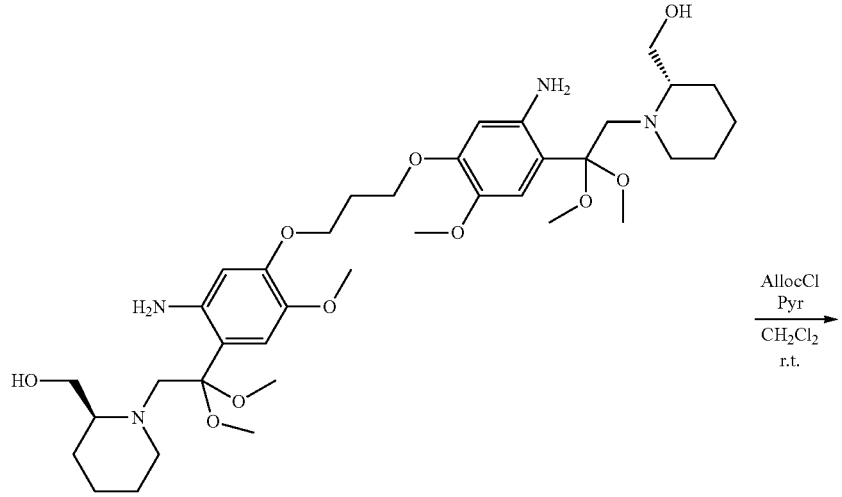

-continued
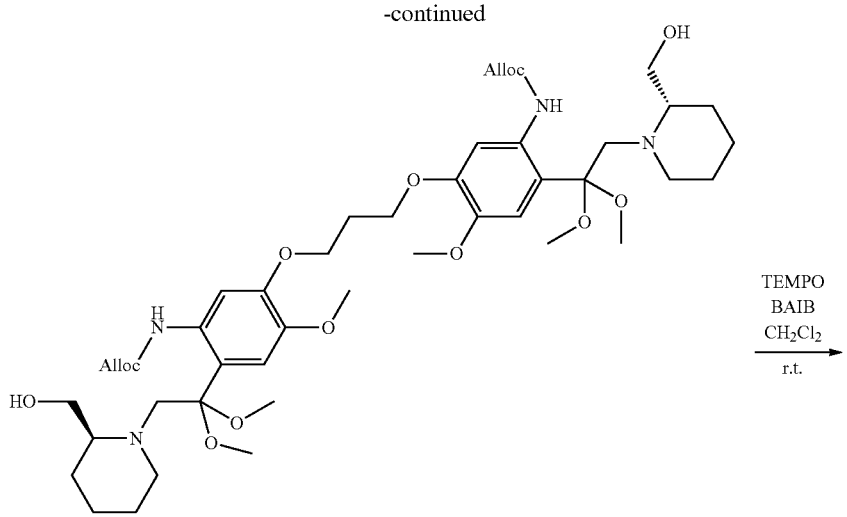
44
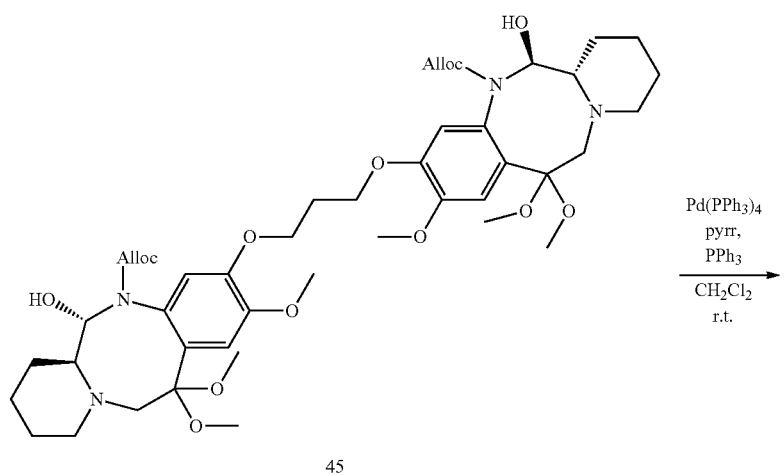
45
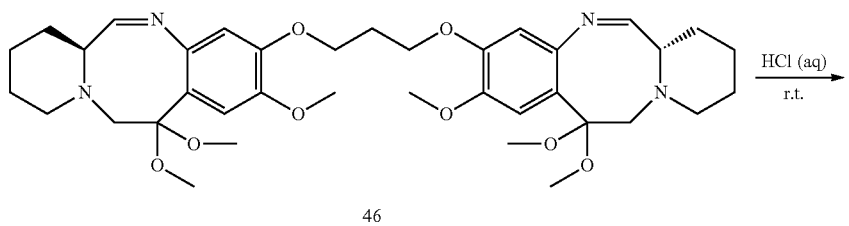
46
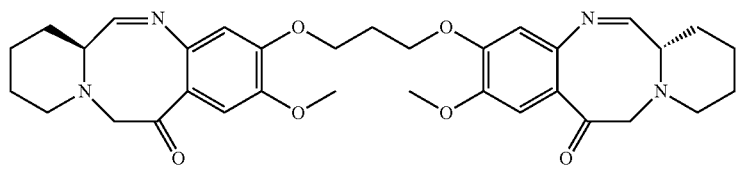
47
Example 13
A monomeric compound 63 is prepared by reacting the C-ring precursor 33 from Example 10 in the following reaction scheme:

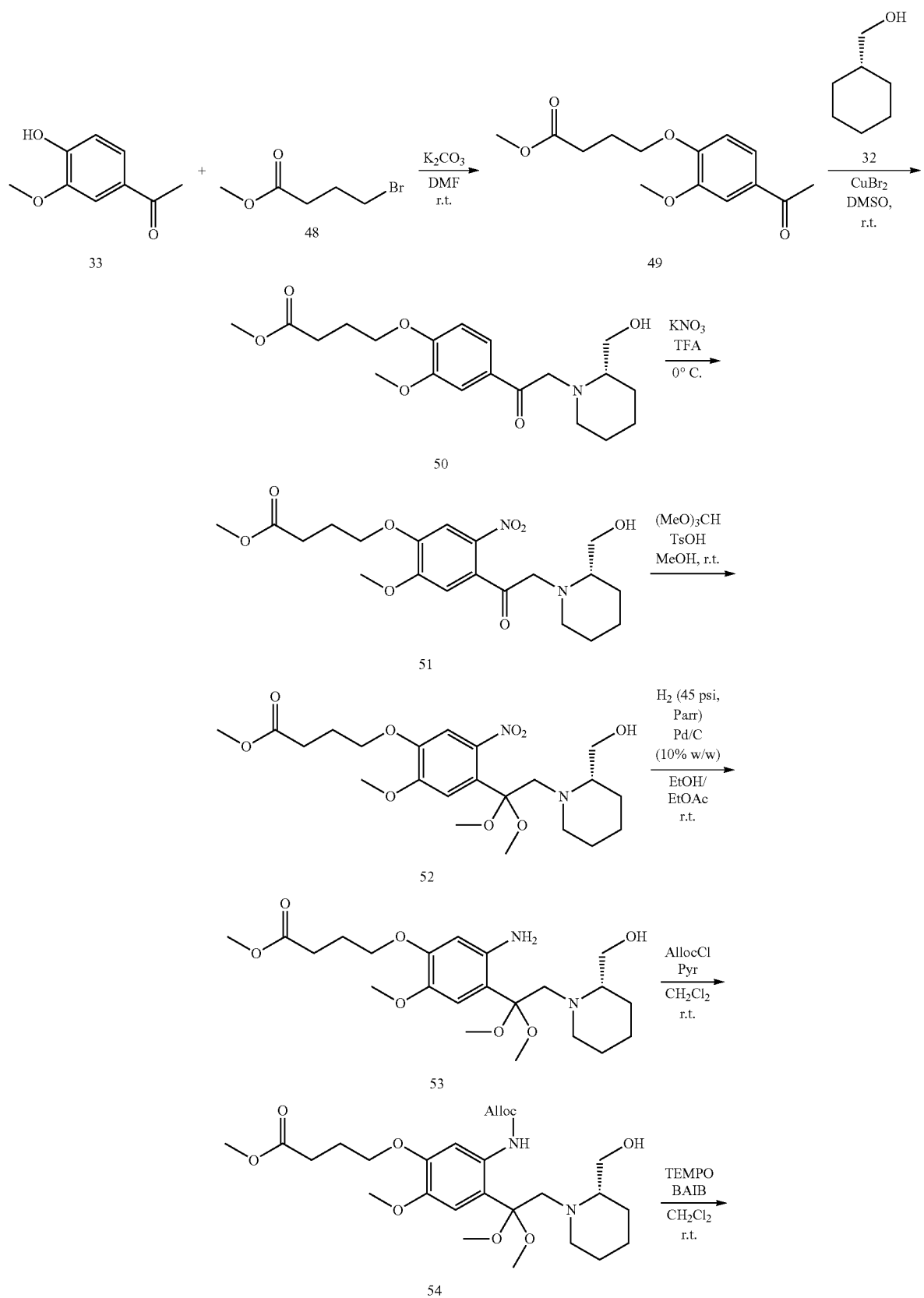

-continued
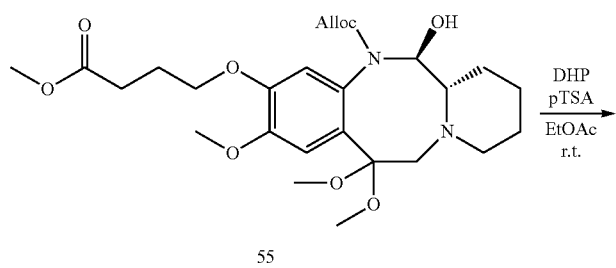
55
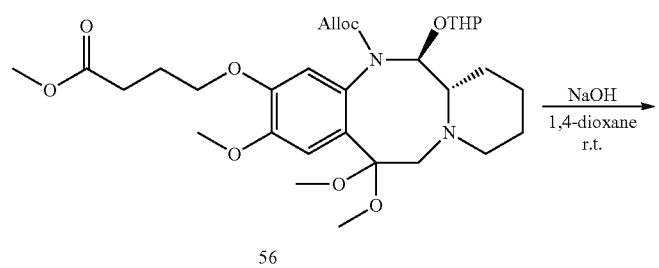
56
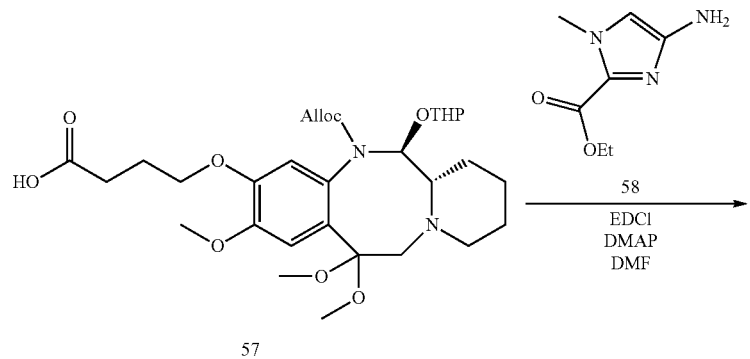
57
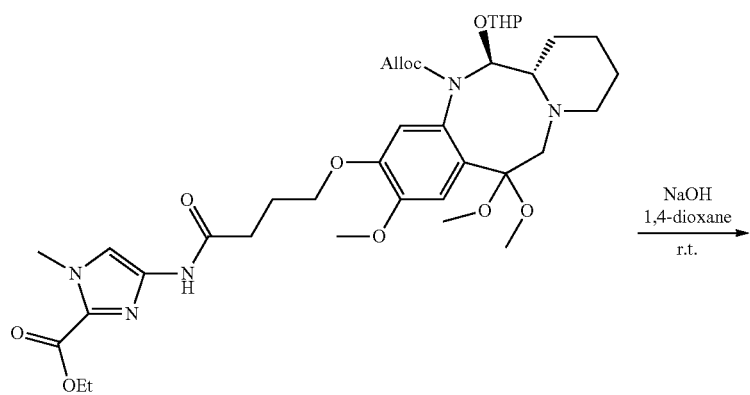
59

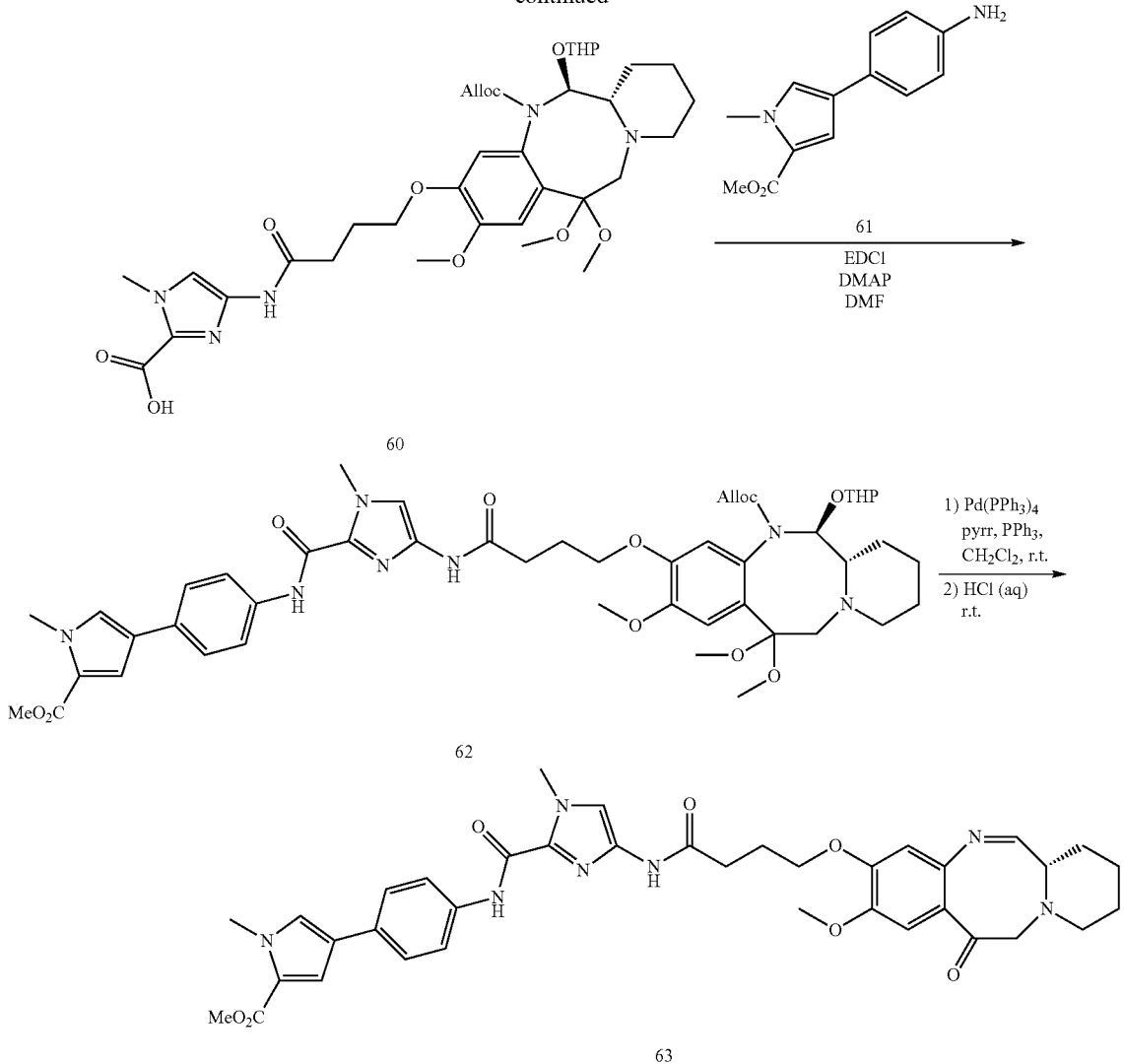

The first step in preparing the monomeric conjugate compound 63 is by treating acetovanillone (4'-hydroxy-3'-methoxyacetophenone) 33 (Sigma-Aldrich) with methyl 4-bromobutanoate 48 (Fluorochem) in DMF in the presence of potassium carbonate as a base (7, 77) to give the coupled product 49. Product 49 will be reacted with S-(+)-2-pyrrolidinemethanol 32 in a copper(II) carbonyl-amine coupling reaction to provide the product 50 The aromatic ring of 50 will then undergo aromatic nitration to produce the nitro compound 51. The carbonyl group of compound 51 will then be protected as the ketal 52. The nitro group of compound 52 will then be reduced (27) to the corresponding amine 53 using $H_2$ and Pd/C (10% w/w). The aniline derivative 53 will then be treated with allyl chloroformate in the presence of pyridine to give the Alloc protected compound 54 (72, 73). The ring cyclisation will be carried out using oxidation conditions of a TEMPO/BAIB system (75, 76) to afford the cyclised compound 55. The alcohol group of compound 55 will be protected by treating it with DHP in presence of PTSA to afford 56 (72, 73). The terminal ester of 56 will be hydrolysed to corresponding carboxylic acid 57 using sodium hydroxide in dioxane to facilitate addition of heterocyclic fragments by peptide coupling. The carboxylic acid 57 will be coupled (77, 78) with a suitable heterocyclic amine, ethyl 4-amino-1-methyl-1H-2-carboxylate 58 (22-26, 77, 78), to give the protected compound 59. A further peptide coupling of compound 59 will be carried out with methyl 4-(4-aminophenyl)-1-methyl-1H-pyrrole-2-carboxylate 61 which was prepared as described in Example 14. These peptide coupling reactions will be carried out using EDCI, DMAP and DMF to give a protected PBC conjugate 62. Treatment of the Alloc protected PBC conjugate 62 with Pd(PPh3)$_4$ in the presence of pyrrolidine will remove the Alloc protecting group (7, 72, 73, 77). Finally, treatment with acid will remove the ketal protecting groups to provide the PBC conjugate 63.

Example 14

Methyl 4-(4-aminophenyl)-1-methyl-1H-pyrrole-2-carboxylate 61 a side chain group suitable for attaching to PBC compounds was prepared as described below.

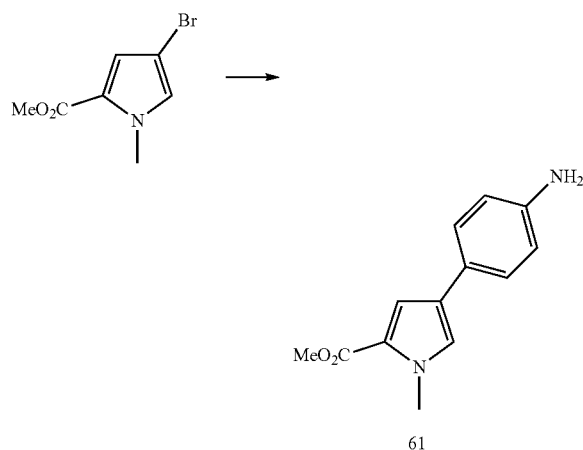

A mixture of methyl 4-bromo-1-methyl-1H-pyrrole-2-carboxylate (750 mg, 3.44 mmol), 4-(4,4,5,5-tetramethyl-1,3,2-dioxaborolan-2-yl)aniline (905 mg, 4.13 mmol) and potassium carbonate (1.43 g, 10.3 mmol) in toluene/ethanol/water (9:3:1) (13 mL total) was degassed with nitrogen for 5 mins. Tetrakis(triphenylphosphine)palladium(0) (230 mg, 6 mol %) was then charged and the reaction mixture was irradiated with microwaves at 100° C. for 15 mins. Water (10 mL) was then added to the reaction mixture, which was extracted with ethyl acetate (3×40 mL). The combined organic extracts were then dried over sodium sulfate, filtered and concentrated. The resulting residue was purified by column chromatography (silica), eluting with ethyl acetate/hexanes (from 0% to 50%), to give the title compound (145 mg, 18%) as a yellow solid.

MS (ES+): m/z=231 (M+H)$^+$; LCMS: $t_R$=5.17 min.

Example 15

HPLC Assay

Ligand-DNA Complex Preparation:

Ligand-DNA complexes will be prepared by incubating the ligands with hairpin oligonucleotides of chosen sequence in a 4:1 molar ratio at room temperature. Samples will be withdrawn at various time intervals and subjected to Ion-Pair RPLC and mass spectrometry analysis as described below.

Ion-Pair Reversed-Phase Liquid Chromatography:

Chromatography will be performed on a Thermo Electron HPLC system equipped with a 4.6×50 mm Xterra MS C18 column packed with 2.5 µM particles (Waters Ltd, UK), an UV 1000 detector, an AS3000 autosampler, a SCM1000 vacuum degasser and Chromquest software (Version 4.1). A gradient system of 100 mM triethyl ammonium bicarbonate (TEAB) as buffer A, and 40% acetonitrile in water (HPLC grade, Fischer Scientific UK) as buffer B will be used. For buffer A, a 1 M pre-formulated buffer of TEAB (Sigma-Aldrich, U.K) will be diluted to 100 mM with HPLC grade water (Fischer Scientific, U.K). The gradient will be ramped from 90% A at 0 mins to 50% A at 20 mins, 65% A at 30 mins and finally to 10% A at 45 mins. UV absorbance will be monitored at 254 nm, and fractions containing separated components will be collected manually, combined when appropriate, lyophilized and analyzed using MALDI TOF mass spectrometry as described below.

Mass Spectrometry Analysis (ESI-MS):

ESI-MS spectra will be acquired on a Micromass Q-TOF Global Tandem Mass Spectrometer (Waters, UK) fitted with a NanoSpray ion source. Negative mode will be used for data acquisition, and the instrument will be calibrated with ions produced from a standard solution of taurocholic acid (10 pmole/µl) in acetonitrile. The HPLC fractions will be collected and lyophilized (Speedvac, Thermo Electron, UK) and mixed with a 1:1 v/v mixture of 40% acetonitrile/water and 20 mM triethylamine/water (TEA, Fischer Scientific, UK) which will also be used as electrospray solvent. 3-5 µL of sample will be loaded into a metal-coated borosilicate electrospray needle with an internal diameter of 0.7 mm and a spray orifice of 1-10 µm (NanoES spray capillaries, Proxeon Biosystems, UK) which will be positioned at ~10 mm from the sample cone to provide a flow rate of ~20 nl/min. Nitrogen will be used as the API gas, and the capillary, cone and RF Lens 1 voltages will be set to values such as 1.8-2.0 kV, ~35 V and 50 V, respectively, to ensure minimum fragmentation of the ligand/DNA adducts. The collision and MCP voltages will be set to values such as 5V and 2200 V, respectively. Spectra will be acquired over the m/z range 1000-3000.

Mass Spectrometry Analysis (MALDI TOF):

Samples will be diluted with matrix (37 mg THAP in 1 mL ACN, 45 mg ammonium citrate in 1 mL water—mixed 1:1 for matrix) either 2:1, 1:1 or 1:5 (sample:matrix) to determine the most effective ratio. 1 µl of sample/matrix mixture will be spotted onto the MALDI target plate and allowed to dry. Analyses will be carried out on a Voyager DE-Pro with a nitrogen laser in positive linear mode using delayed extraction (500 nsec) and an accelerating voltage of 25,000 V. Acquisition will be between 4000-15000 Da with 100 shots/spectrum.

Example 16

Fluorescent Resonance Energy Transfer (FRET) DNA Thermal Denaturation Assay 400 nM solutions of fluorescence-tagged oligonucleotide (e.g., 5'-Fam-TATA-(X)$_n$-TATA-Tamra-3'; where X=any number or combination of bases) in FRET buffer (50 mM potassium cacodylate, pH 7.4) will be prepared by diluting a 20 µM stock solution in water. This solution will be heated at 85° C. for 5 mins before cooling to room temperature over 5 hours to promote annealing. The ligand solution will be prepared initially in a concentration double that required for the final solution, and dilution from the initial 10 mM DMSO stock solution will be carried out using FRET buffer. 50 µL of the annealed DNA and 50 µL of ligand solution will be placed in a well of a 96-well plate (MJ Research Inc, USA) which will be processed in a DNA Engine Opticon (MJ Research). Fluorescence readings will be taken at intervals of 0.5° C. over the range 30-100° C., with a constant temperature maintained for 30 seconds prior to each reading. The incident radiation will be 450-495 nm with detection at 515-545 nm. The raw data will be imported into the Origin program (Version 7.0, OriginLab Corp. USA), and the graphs smoothed using a 10-point running average prior to normalization. Determination of melting temperatures will be based on obtaining values at the maxima of the first derivative of the smoothed melting curves using a script. The difference between the melting temperature of the sample and that of the blank (i.e., the ΔTm) will be used for comparative purposes.

Example 17

Cytotoxicity Analysis of PDD Monomeric Conjugate Compound by MTT Assay

Cell Culture

MDA MB231 (triple negative human breast cancer) was obtained from the American Type Culture Collection. The cell-line was maintained in monolayer culture in 75 cm$^2$ flasks (TPP, Switzerland) under a humidified 5% $CO_2$ atmosphere at 37° C. The MDA MB231 cell line was maintained in high glucose DMEM (4.5 g\l; Invitrogen), foetal bovine serum (10%, Biosera UK), non-essential amino acids (ix; Invitrogen), L-glutamine (2 mM; Invitrogen) and Penicillin-Streptomycin (1% v/v, Invitrogen). For passaging, cells were washed with PBS (GIBCO 14040, Invitrogen, UK), incubated with trypsine (GIBCO 25300, Invitrogen, UK), and re-seeded into fresh medium. For seeding, cells were counted using a Neubauer haemocytometer (Assistant, Germany) by microscopy (Nikon, USA) on a non-adherent suspension of cells that were washed in PBS, trypsinised, centrifuged at 8° C. at 8000 rpm for 5 min and re-suspended in fresh medium.

MTT Assay

The cells were grown in normal cell culture conditions at 37° C. under a 5% $CO_2$ humidified atmosphere using appropriate medium. The cell count was adjusted to 105 cells/ml and 5,000-20,000 cells were added per well depending on the cell line. The cells were incubated for 24 hours and 1 µl of the appropriate inhibitor concentrations were added to the wells in triplicates. After 96 h of continuous exposure to each compound, the cytotoxicity was determined using the 3-(4,5-Dimethylthiazol-2-yl)-2,5-diphenyltetrazolium bromide (MTT) (Lancaster Synthesis Ltd, UK) colorimetric assay. Absorbance was quantified by spectrophotometry at X=570 nm (Envision Plate Reader, PerkinElmer, USA). $IC_{50}$ values were calculated by a dose-response analysis using the Prism GraphPad Prism® software.

TABLE 4

$IC_{50}$ values (nM) determined after 96 hours exposure for the C ring-linked PDD monomer (23)

| Compound | MDA MB 231 (Triple negative breast cancer cell line) $IC_{50}$ (nanomolar) |
|---|---|
| 23 | 221 |

REFERENCES

1. Antonow, D., and Thurston, D. E. (2011) *Chem Rev* 111, 2815-2864.
2. Cipolla, L., Araujo, A. C., Airoldi, C., and Bini, D. (2009) *Anticancer Agents Med Chem* 9, 1-31.
3. Gerratana, B. (2012) *Med Res Rev* 32, 254-293.
4. Hartley, J. A. (2011) *Expert Opin Investig Drugs* 20, 733-744.
5. Kamal, A., Reddy, K. L., Devaiah, V., Shankaraiah, N., and Reddy, D. R. (2006) *Mini Rev Med Chem* 6, 53-69.
6. Hurley, L. H., Reck, T., Thurston, D. E., Langley, D. R., Holden, K. G., Hertzberg, R. P., Hoover, J. R., Gallagher, G., Jr., Faucette, L. F., Mong, S. M., (1988) *Chem Res Toxicol* 1, 258-268.
7. Wells, G., Martin, C. R., Howard, P. W., Sands, Z. A., Laughton, C. A., Tiberghien, A., Woo, C. K., Masterson, L. A., Stephenson, M. J., Hartley, J. A., Jenkins, T. C., Shnyder, S. D., Loadman, P. M., Waring, M. J., and Thurston, D. E. (2006) *J Med Chem* 49, 5442-5461.
8. Brucoli, F., Hawkins, R. M., James, C. H., Jackson, P. J., Wells, G., Jenkins, T. C., Ellis, T., Kotecha, M., Hochhauser, D., Hartley, J. A., Howard, P. W., and Thurston, D. E. (2013) *J Med Chem* 56, 6339-6351.
9. Kotecha, M., Kluza, J., Wells, G., O'Hare, C. C., Forni, C., Mantovani, R., Howard, P. W., Morris, P., Thurston, D. E., Hartley, J. A., and Hochhauser, D. (2008) *Mol Cancer Ther* 7, 1319-1328.
10. Puvvada, M. S., Hartley, J. A., Jenkins, T. C., and Thurston, D. E. (1993) *Nucleic Acids Res* 21, 3671-3675.
11. Clingen, P. H., De Silva, I. U., McHugh, P. J., Ghadessy, F. J., Tilby, M. J., Thurston, D. E., and Hartley, J. A. (2005) *Nucleic Acids Res* 33, 3283-3291.
12. Puvvada, M. S., Forrow, S. A., Hartley, J. A., Stephenson, P., Gibson, I., Jenkins, T. C., and Thurston, D. E. (1997) *Biochemistry* 36, 2478-2484.
13. Barkley, M. D., Cheatham, S., Thurston, D. E., and Hurley, L. H. (1986) *Biochemistry* 25, 3021-3031.
14. Seifert, J., Pezeshki, S., Kamal, A., and Weisz, K. (2012) *Organic & Biomolecular Chemistry* 10, 6850-6860.
15. Smellie, M., Bose, D. S., Thompson, A. S., Jenkins, T. C., Hartley, J. A., and Thurston, D. E. (2003) *Biochemistry* 42, 8232-8239.
16. Kopka, M. L., Goodsell, D. S., Baikalov, I., Grzeskowiak, K., Cascio, D., and Dickerson, R. E. (1994) *Biochemistry* 33, 13593-13610.
17. Kizu, R., Draves, P. H., and Hurley, L. H. (1993) *Biochemistry* 32, 8712-8722.
18. Leimgruber, W., Stefanovic, V., Schenker, F., Karr, A., and Berger, J. (1965) *J Am Chem Soc* 87, 5791-5793.
19. Arima, K., Kosaka, M., Tamura, G., Imanaka, H., and Sakai, H. (1972) *J Antibiot (Tokyo)* 25, 437-444.
20. Sato, S., Iwata, F., Yamada, S., Kawahara, H., and Katayama, M. (2011) *Bioorg Med Chem Lett* 21, 7099-7101.
21. Thurston D. E. and Bose D. S., *Chem Rev* (1994); 94:433-465.
22. Damayanthi, Y., et al.; *Journal of Organic Chemistry* (1999), 64, 290-292;
23. Kumar, et al., *Heterocyclic Communications* (2002) 8, 19-26.
24. Kumar, R, Lown, J. W.; *Oncology Research*, (2003) 13, 221-233.
25. Baraldi, P. G. et al., *Journal of Medicinal Chemistry* (1999) 42, 5131-5141.
26. Wells, G., et al., *Proc. Am. Assoc. Canc. Res.* (2003) 44, 452.
27. Thurston, D. E.; Howard, P. W. WO 2004/043963.
28. Farmer, J. D., Rudnicki, S. M., and Suggs, J. W. (1988) *Tetrahedron Lett* 29, 5105-5108;
29. Bose, D. S., Thompson, A. S., Ching, J. S., Hartley, J. A., Berardini, M. D., Jenkins, T. C., Neidele, S., Hurley, L. H., and Thurston, D. E. (1992) *J. Am. Chem. Soc.* 114, 4939.
30. Gregson, S. J., Howard, P. W., Hartley, J. A., Brooks, N. A., Adams, L. J., Jenkins, T. C., Kelland, L. R., and Thurston, D. E. (2001) *J Med Chem* 44, 737-748.
31. Jenkins, T. C., Hurley, L. H., Neidle, S., and Thurston, D. E. (1994) *J Med Chem* 37, 4529-4537.

32. Wu, J., Clingen, P. H., Spanswick, V. J., Mellinas-Gomez, M., Meyer, T., Puzanov, I., Jodrell, D., Hochhauser, D., and Hartley, J. A. (2013) *Clin Cancer Res* 19, 721-730.
33. Hochhauser, D., Meyer, T., Spanswick, V. J., Wu, J., Clingen, P. H., Loadman, P., Cobb, M., Gumbrell, L., Begent, R. H., Hartley, J. A., Jodrell, D., (2009) *Clin Cancer Res* 15, 2140-2147.
34. O'Neil, I. A., Murray, C. L., Potter, A. J. (1997) *Tetrahedron Letters* 38, 3609-3610.
35. Cooper, N.; Hagan, D. R.; Tiberghien, A.; Ademefun, T.; Matthews, C. S.; Howard, P. W.; Thurston, D. E. (2002) *Chem. Commun.* 16, 1764.
36. Tiberghien, A. C.; Hagan, D.; Howard, P. W.; Thurston, D. E. (2004) *Bioorg. Med. Chem. Lett.,* 14, 5041.
37. Madani, H.; Thompson, A. S.; Threadgill, M. D. (2002) *Tetrahedron* 58, 8107.
38. Kitamura, T.; Sato, Y.; Mori, M. (2004) *Tetrahedron* 60, 9649.
39. Katsifis, A. G.; McPhee, M. E.; Ridley, D. D. (1998) *Aust. J. Chem.* 51, 1121.
40. Kamal, A.; Reddy, B. S. P.; Reddy, B. S. N. (1996) *Tetrahedron Lett.* 37, 6803.
41. Kamal, A.; Reddy, K. L.; Reddy, G. S. K.; Reddy, B. S. N. (2004) *Tetrahedron Lett.,* 45, 3499.
42. Kamal, A.; Laxman, E.; Laxman, N.; Rao, N. V. (2000) *Bioorg. Med. Chem. Lett.,* 10, 2311.
43. Kamal, A.; Laxman, E.; Arifuddin, M. (2000) *Tetrahedron Lett.,* 41, 7743.
44. Kamal, A.; Babu, A. H.; Ramana, A. V.; Ramana, K. V.; Bharathi, E. V.; Kumar, M. S. (2005) *Bioorg. Med. Chem. Lett.,* 15, 2621.
45. Correa, A.; Tellitu, I.; Dominguez, E.; Moreno, I.; Sanmartin, R. (2005) *J. Org. Chem.,* 70, 2256.
46. Artico, M.; De Martino, G.; Giuliano, R.; Massa, S.; Porretta, G. C. (1969) *J. Chem. Soc., Chem. Commun.,* 671.
47. Thurston, D. E.; Langley, D. R. (1986) *J. Org. Chem.,* 51, 705.
48. Langlois, N.; Rojas-Rousseau, A.; Gaspard, C.; Werner, G. H.; Darro, F.; Kiss, R. (2001) *J. Med. Chem.,* 44, 3754.
49. Rojas-Rousseau, A.; Langlois, N. (2001) *Tetrahedron,* 57, 3389.
50. Kamal, A.; Reddy, B. S. N.; Reddy, B. S. P. (1997) *Bioorg. Med. Chem. Lett.,* 7, 1825.
51. Kamal, A.; Rao, N. V. (1996) *Chem. Commun.,* 3, 385.
52. Kamal, A.; Laxman, E.; Reddy, P. S. M. M. (2000) *Synlett,* 10, 1476.
53. Kamal, A.; Reddy, P. S. M. M.; Reddy, D. R. (2003) *Tetrahedron Lett.,* 44, 2857.
54. Langley, D. R. & Thurston, D. E., (1987) *J. Organic Chemistry,* 52, 91-97.
55. Thurston, D. E.; Bose, D. S.; Thompson, A. S.; Howard, P. W.; Leoni, A.; Croker, S. J.; Jenkins, T. C.; Neidle, S.; Hartley, J. A.; Hurley, L. H. (1996) *J. Org. Chem.,* 61, 8141.
56. Kumar, R.; Lown, J. W. (2003) *Mini-Rev. Med. Chem.,* 3, 323.
57. Reddy, B. S. P.; Damayanthi, Y.; Lown, J. W. (1999) *Synlett,* 7, 1112.
58. Matsumoto, T.; Aoyama, T.; Shioiri, T. (1996) *Tetrahedron,* 52, 13521.
59. Matsumoto, T.; Matsunaga, N.; Kanai, A.; Aoyama, T.; Shioiri, T.; Osawa, E. (1994) *Tetrahedron,* 50, 9781.
60. Eguchi, S.; Yamashita, K.; Matsushita, Y.; Kakehi, A. (1995) *J. Org. Chem.,* 60, 4006.
61. Molina, P.; Diaz, I.; Tarraga, A. (1995) *Tetrahedron,* 51, 5617.
62. Fukuyama, T.; Liu, G.; Linton, S. D.; Lin, S. C.; Nishino, H. (1993) *Tetrahedron Lett.,* 34, 2577.
63. Gregson, S. J.; Howard, P. W.; Corcoran, K. E.; Barcella, S.; Yasin, M. M.; Hurst, A. A.; Jenkins, T. C.; Kelland, L. R.; Thurston, D. E. (2000) *Bioorg. Med. Chem. Lett.,* 10, 1845.
64. Gregson, S. J.; Howard, P. W.; Barcella, S.; Nakamya, A.; Jenkins, T. C.; Kelland, L. R.; Thurston, D. E. (2000) *Bioorg. Med. Chem. Lett.,* 10, 1849.
65. Gregson, S. J.; Howard, P. W.; Corcoran, K. E.; Jenkins, T. C.; Kelland, L. R.; Thurston, D. E. *Bioorg. Med. Chem. Lett.* 2001, 11, 2859.
66. Gregson, S. J.; Howard, P. W.; Thurston, D. E. (2003) *Bioorg. Med. Chem. Lett.,* 13, 2277.
67. Case, D. A., Darden, T. A., Cheatham III, T. E., Simmerling, C. L., Wang, J., Duke, R. E., Luo, R., Walker, R. C., Zhang, W., Merz, K. M., Roberts, B., Wang, B., Hayik, S., Roitberg, A., Seabra, G., Kolossviry, I., Wong, K. F., Paesani, F., Vanicek, J., Liu, J., Wu, X., Brozell, S. R., Steinbrecher, T., Gohlke, H., Cai, Q., Ye, X., Wang, J., Hsieh, M.-J., Cui, G., Roe, D. R., Mathews, D. H., Seetin, M. G., Sagui, C., Babin, V., Luchko, T., Gusarov, S., Kovalenko, A., Kollman, P. A. (2010) AMBER 11, University of California, San Francisco, 2010.
68. Perez, A., Marchan, I., Svozil, D., Sponer, J., Cheatham, T. E., 3rd, Laughton, C. A., and Orozco, M. (2007) *Biophys J* 92, 3817-3829.
69. Ryckaert, J.-P., Ciccotti, G., and Berendsen, H. J. C. (1977) *Journal of Computational Physics* 23, 327-341.
70. Wang, H., and Laughton, C. A. (2009) *Phys Chem Chem Phys* 11, 10722-10728.
71. Wuts, P. G. M. and Greene, T. W., Protective Groups in Organic Synthesis, 4th Edition, Wiley-Interscience, 2007.
72. Kocienski, P., *Protective Groups,* 3rd Edition, Thieme (2005).
73. Kang, G. D.; Howard, P. W.; Thurston, D. E. (2003) *Chem. Commun.,* 14, 1688.
74. Howard, P. W.; Gregson, S. J.; WO 2005/085251.
75. Howard, P. W., Thurston, D. E.; Wells, G. WO 2007/039752.
76. Howard, P. W., Thurston, D. E.; Rahman, K. M. WO 2013/164593.
77. Sugasawa, T., Toyoda, T., Adachi, M., Sasakura, K., U.S. Pat. No. 4,160,784.
78. Dong, Q.; Anderson, C. E.; Ciufolini, M. A. (1995) Tetrahedron Lett., 36, 5681.
79. David E. Bergbreiter, David P. Rainville *J. Org. Chem.*, (1976) 41, 3031-3033.
80. Evans, R. W., Zbieg, J. R., Zhu, S., Li, W., MacMillan, D. W. C. 2013) *J. Am. Chem. Soc.* 135, 16074-16077.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents. All documents cited herein are incorporated by reference.

The invention claimed is:

1. A compound of formula (I):

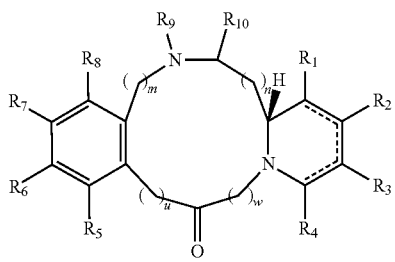

and salts or solvates thereof, wherein:

the dotted lines indicates the optional presence of a double bond between one or more of C1 and C2, C2 and C3, and C3 and C4;

$R_4$ is selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2R$, $CO_2H$, COR, CN;

$R_5$, $R_6$ and $R_8$ are independently selected from H, R, OH, OR, SH, SR, $NH_2$, NHR, NRR', $CO_2H$, $CH_2$—$CO_2H$, $CO_2R$, $CH_2$—$CO_2R$, $NO_2$, $Me_3Sn$ and halo;

each R and R' is independently selected from optionally substituted $C_{1-12}$ alkyl, $C_{3-20}$ heterocyclyl, $C_{3-20}$ heteroaryl, $C_{4-32}$ heteroaralkyl, $C_{5-20}$ aryl groups and $C_{6-32}$ aralkyl;

and either:
(i) $R_9$ and $R_{10}$ together form a double bond;
(ii) $R_9$ is H and $R_{10}$ is OH; or
(iii) $R_9$ is H and $R_{10}$ is $OR^A$ and $R^A$ is $C_{1-6}$ alkyl;

wherein each of m, n, u and w may be 0 or 1; and with the proviso that the compound of formula (I) is a compound according to (a), (b), (c) or (d) wherein:

(a) the compound is a dimer with each monomer being the same or different and being of formula (I) to give a dimer of formula:

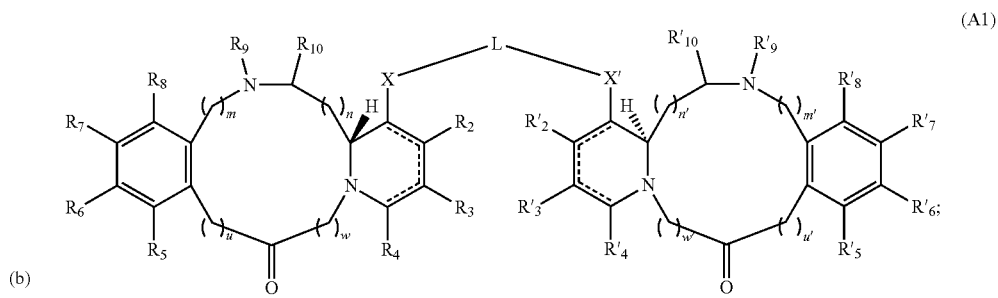

(A1)

(b)

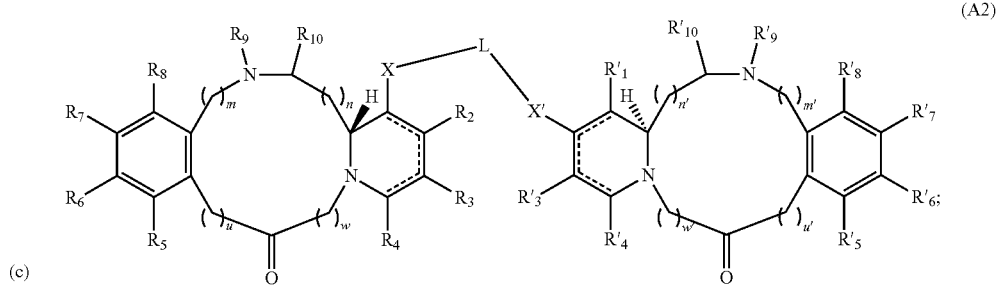

(A2)

(c)

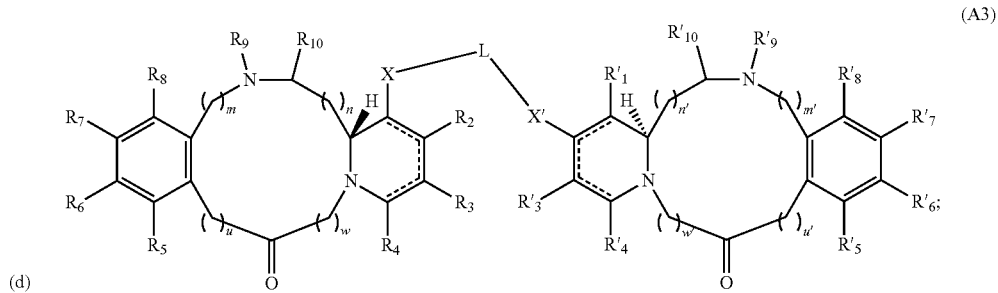

(A3)

(d)

-continued
(e) 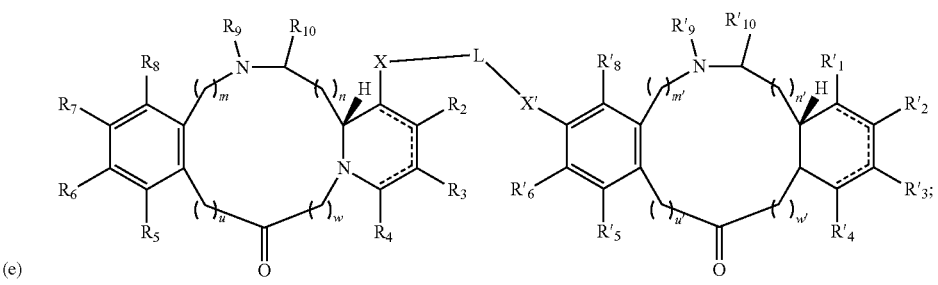 (A4)
(f) 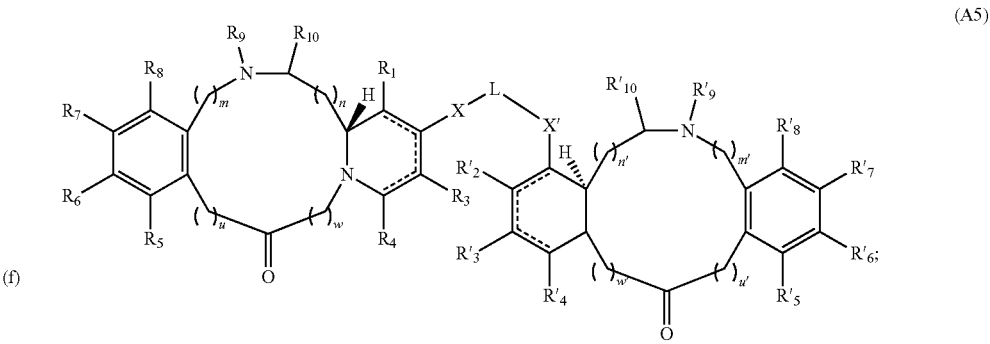 (A5)
(g) 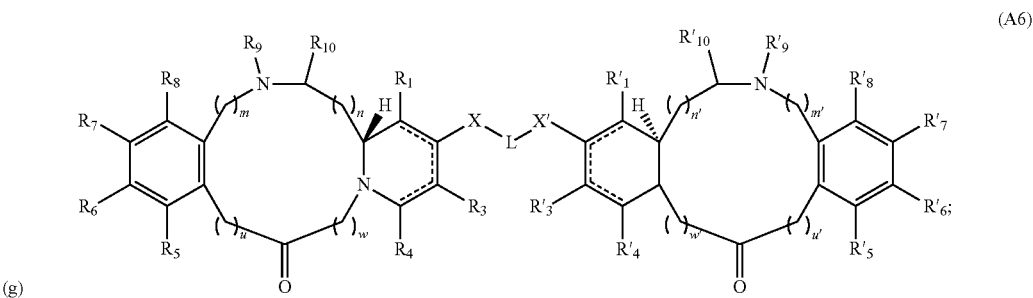 (A6)
(h) 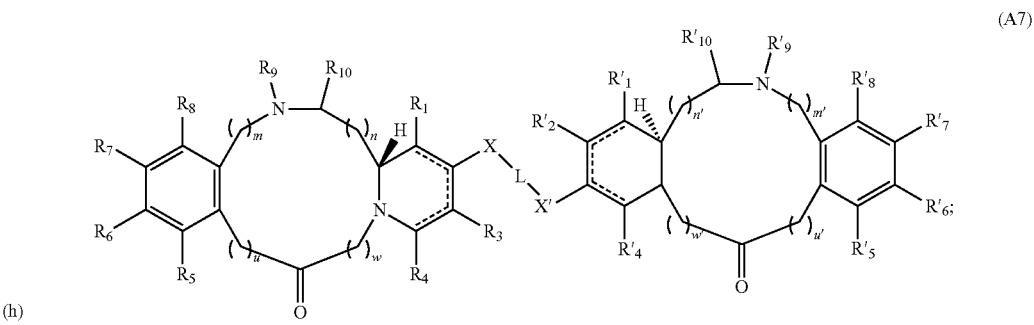 (A7)
(i) 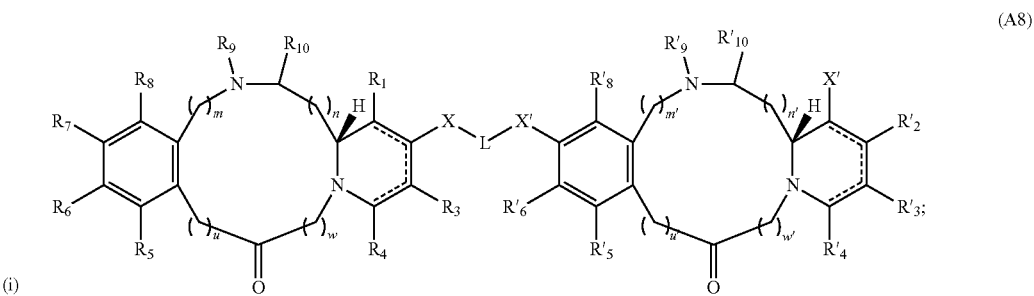 (A8)

-continued
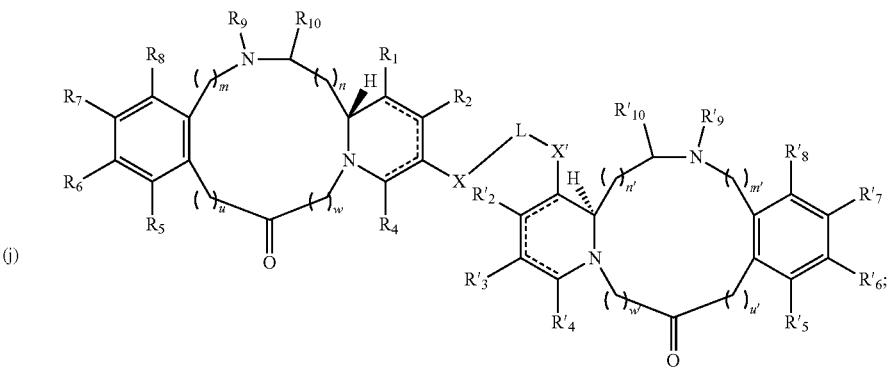
(j) (A9)
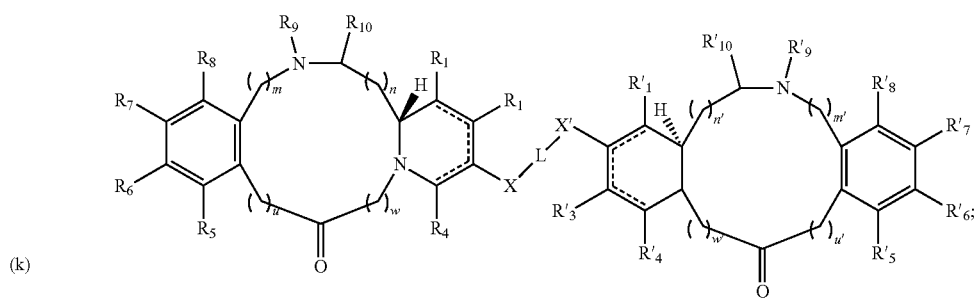
(k) (A10)
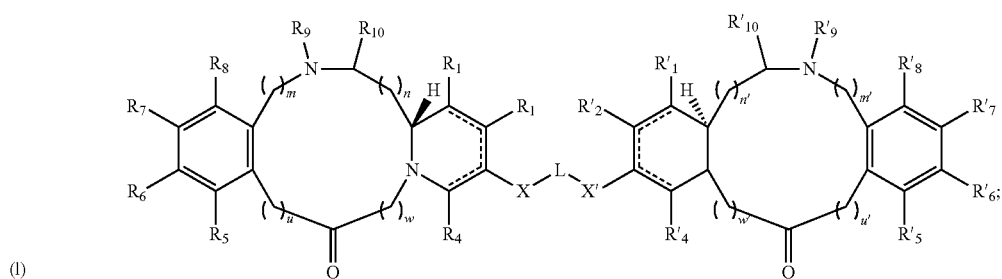
(l) (A11)
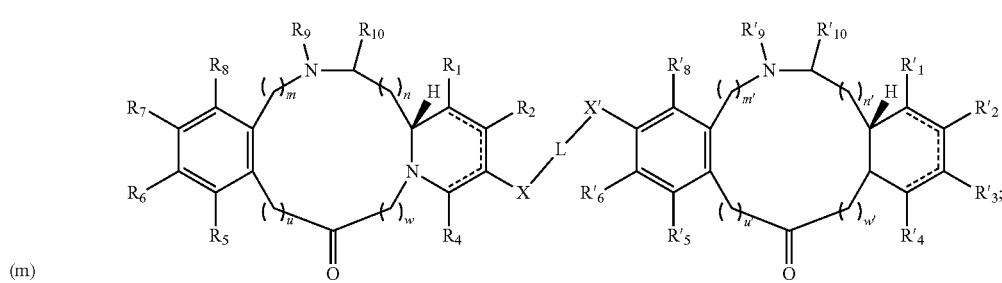
(m) (A12)
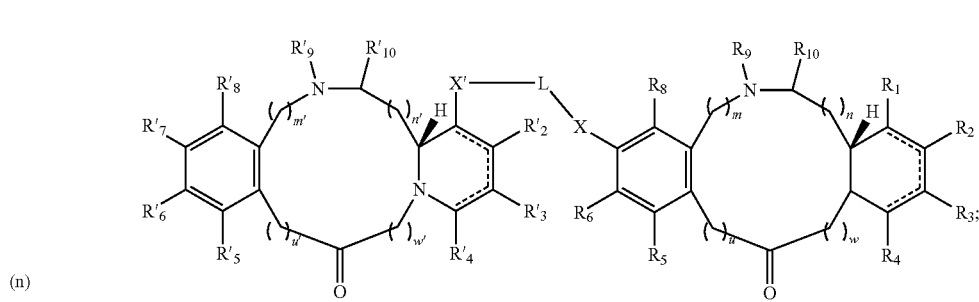
(n) (A13)

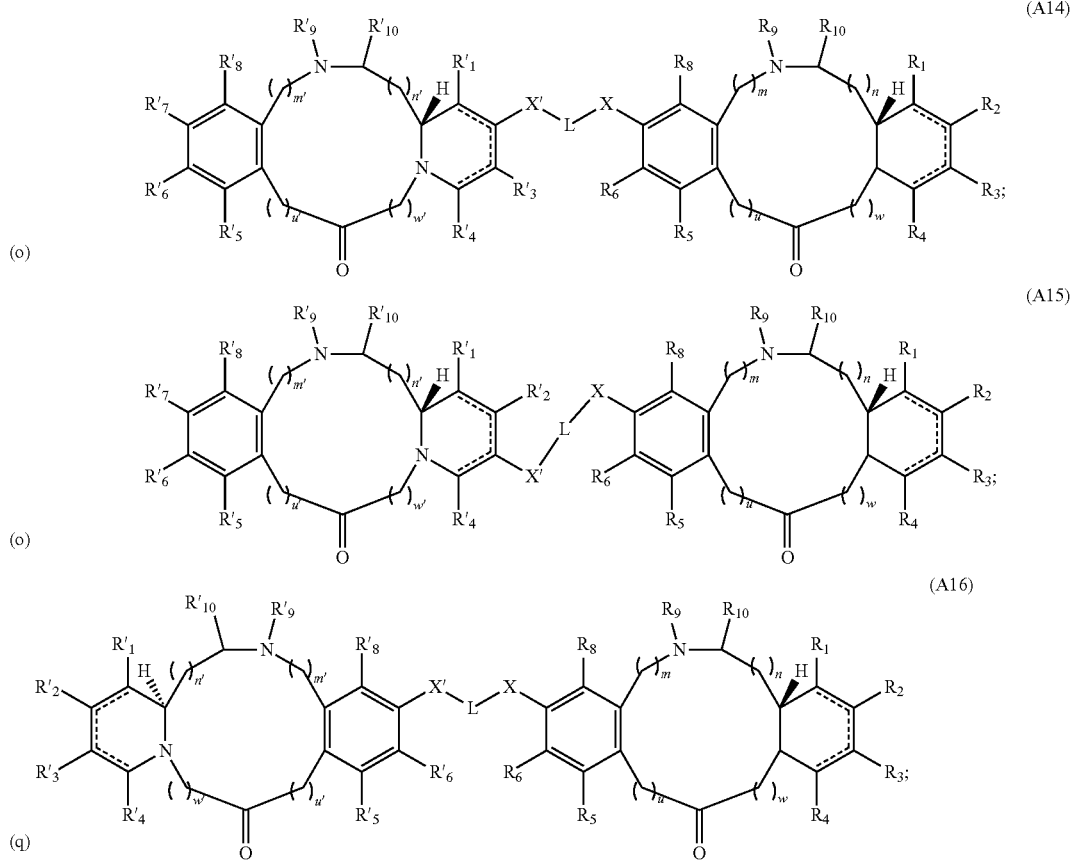

where one of R₁, R₂, R₃ and R₇ of the first monomer and one of R'₁, R'₂, R'₃ and R'₇ of the second monomer form together a bridge having the formula —X-L-X'— linking the monomers and m+n+u+w=1;

where the remaining groups m', n', u', w', R'₄, R'₅, R'₆, R'₈, R'₉ and R'₁₀ are independently selected from groups with the same meanings as for m, n, u, w, R₄, R₅, R₆, R₈, R₉ and R₁₀ respectively;

and the remaining of R₁, R₂ and R₃ of the first monomer and the remaining of R'₁, R'₂ and R'₃ of the second monomer that do not form the bridge are independently selected from H, R, OH, OR, NH₂, NHR, NRR', CH₂—OR, =O, =CH—R, =CH₂, CH₂—CO₂R, CH₂—CO₂H, CH₂—SO₂R, O—SO₂R, CO₂R, CO₂H, COR, CN, (C₁₋₁₂ alkylene)-C(O)NR", R''' and (C₂₋₁₂ alkenylene)-C(O)NR'R" and halo;

and the remaining of R₇ of the first monomer and R'₇ of the second monomer that do not form the bridge are independently selected from H, R, OH, OR, NH₂, NHR, NRR', CH₂—OR, CH₂—CO₂R, CH₂—CO₂H, CH₂—SO₂R, O—SO₂R, CO₂R, CO₂H, COR, CN, (C₁₋₁₂ alkylene)-C(O)NR",R''' and (C₂₋₁₂ alkenylene)-C(O)NR'R" and halo;

or (b) the compound is a dimer with each monomer being the same or different and being of formula (I) to give a dimer of formula (A1), (A2), (A3), (A5), (A6), (A7), (A9), (A10) or (A11); where the remaining groups m', n', u', w', R'₄, R'₅, R'₆, R'₈, R'₉ and R'₁₀ are independently selected from groups with the same meanings as for m, n, u, w, R₄, R₅, R₆, R₈, R₉ and R₁₀ respectively;

where one of R₁, R₂ and R₃ of the first monomer and one of R'₁, R'₂, and R'₃ of the second monomer form together a bridge having the formula —X-L-X'— linking the monomers and m=n=u=w=0;

and the remaining of R₁, R₂ and R₃ of the first monomer and the remaining of R'₁, R'₂ and R'₃ of the second monomer that do not form the bridge are independently selected from H, R, OH, OR, NH₂, NHR, NRR', CH₂—OR, =O, =CH—R, =CH₂, CH₂—CO₂R, CH₂—CO₂H, CH₂—SO₂R, O—SO₂R, CO₂R, CO₂H, COR, CN, (C₁₋₁₂ alkylene)-C(O)NR", R''' and (C₂₋₁₂ alkenylene)-C(O)NR'R" and halo;

and that R₇ of the first monomer and R'₇ of the second monomer are independently selected from H, R, OH, OR, NH₂, NHR, NRR', CH₂—OR, CH₂—CO₂R, CH₂—CO₂H, CH₂—SO₂R, O—SO₂R, CO₂R, CO₂H, COR, CN, (C₁₋₁₂ alkylene)-C(O)NR",R''' and (C₂₋₁₂ alkenylene)-C(O)NR'R" and halo;

or (c) one of R₁, R₂ and R₃ has the formula:
-X-L-X'-D; or
-(CH₂)𝑓—O—R₁₄;
wherein R₁₄ is selected from H and R;
f is 0 or 1;
and m+n+u+w=0 or 1;
and the remaining of R₁, R₂ and R₃ are independently selected from H, R, OH, OR, NH₂, NHR, NRR', CH₂—OR, =O, =CH—R, CH₂—CO₂R, CH₂—

$CO_2H$, $CH_2$—$SO_2R$, O—$SO_2R$, $CO_2R$, $CO_2H$, COR, CN, ($C_{1-12}$ alkylene)-C(O)NR'''R''' and ($C_{2-12}$ alkenylene)-C(O)NR'R'' and halo;

and $R_7$ is selected from H, R, OH, OR, $NH_2$, NHR, NRR', $CH_2$—OR, $CH_2$—$CO_2R$, $CH_2$—$CO_2H$, $CH_2$—$SO_2R$, O—$SO_2R$, $CO_2R$, $CO_2H$, COR, CN, ($C_{1-12}$ alkylene)-C(O)NR'',R''' and ($C_{2-12}$ alkenylene)-C(O)NR'R'' and halo;

or (d) $R_7$ has the formula:
-X-L-X'-D; or
-$(CH_2)_g$—O—$R_{15}$;
wherein $R_{15}$ is selected from H and R;
g is 0 or 1;
and m+n+u+w=1;
and $R_1$, $R_2$ and $R_3$ are independently selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2R$, $CO_2H$, COR, CN, ($C_{1-12}$ alkylene)-C(O)NR'',R''' and ($C_{2-12}$ alkenylene)-C(O)NR'R'' and halo;

wherein:

X is selected from O, S, NR'', =CR''—, CR''R''', CR''R'''O, C(=O), C(=O)NR'', NR''C(=O), O—C(O) and C(O)—O;

L is selected from an amino acid, a peptide chain having from 2 to 6 amino acids, an alkylene chain containing from 1 to 12 carbon atoms which may contain one or more carbon-carbon double or triple bonds, a paraformaldehyde chain $(OCH_2)_{1-12}$—, a polyethylene glycol chain —$(OCH_2CH_2)_{1-6}$—, which chains may be interrupted by one or more hetero-atoms and/or $C_{3-20}$ heteroaryl and/or $C_{5-20}$ aryl groups;

X' is selected from O, S, NR'', =CR''—, CR''R''', CR''R'''O, C(=O), C(=O)NR', NR''C(=O), O—C(O) and C(O)—O or is absent; and D has the formula (II) or (III):

p is 0 or 1;
q is 1, 2, 3, 4, 5 or 6;
r is 0 or 1;
t is 0 or 1
$Y_3$ is N or CH;
$Y_4$ is N or CH; wherein at least one of $Y_3$ and $Y_4$ is CH;
$R_{13}$ is H, Z—R'', Z—$CO_2R$'', Z—C(=O)—NH—$(CH_2)_{1-6}$—NR''R''', and Z—C(=O)—NH—$(CH_2)_{1-6}$—C(=NH)NR''R''';

Z is absent or is selected from $C_{3-20}$ heteroaryl, $C_{1-6}$ alkyl substituted $C_{3-20}$ heteroaryl, —$(CH_2)_k$—$C_{3-20}$ heterocyclyl, and —O—$(CH_2)_k$—$C_{3-20}$ heterocyclyl group;

k is 0, 1, 2, 3 or 4;
each R'' and R''' is independently selected from H, and optionally substituted $C_{1-12}$ alkyl;
$R_{11}$ is an optionally substituted $C_{3-20}$ heteroaryl; and
$R_{12}$ is an optionally substituted $C_{3-20}$ heteroaryl.

2. A compound of formula (I) according to claim 1, wherein m=n=u=w=0 and wherein the compound is represented by formula (IV):

3. A compound of formula (I) according to claim 1, wherein m=n=u=0 and w=1 and wherein the compound is represented by formula (VIII):

4. A compound of formula (I) according to claim 1, wherein $R_5$ is H.

5. A compound of formula (I) according to claim 1, wherein $R_6$ is selected from H, R, OH, OR and halo.

6. A compound of formula (I) according to claim 1, wherein $R_8$ is H.

7. A compound of formula (I) according to claim 1, wherein X is selected from O, =CR''—, C(=O)NR'' and NR''C(=O).

8. A compound of formula (I) according to claim 1, wherein X' is selected from O, =CR''—, C(=O)NR'' and NR''C(=O).

9. A compound of formula (I) according to claim 1, wherein L is an alkylene chain containing from 1 to 12 carbon atoms which may contain one or more carbon-carbon double or triple bonds.

10. A compound of formula (I) according to claim 1, wherein $R_2$ is selected from H, $CH_2$—$CO_2R$, $CH_2$—$CO_2H$, $CH_2OH$, $CH_2OR$.

11. A compound of formula (I) according to claim 1, wherein D has the formula (II) or (III) and $R_{11}$ is selected from N-methylpyrrolylene, furanylene, thiophenylene, N-methylimidazolylene, oxazolylene, thiazolylene, indolylene, N-methylindolylene, benzofuranylene, benzothiophenylene, benzimidazolylene, N-methylbenzoimidazolylene, benzooxazolylene and benzothiazolylene.

12. A compound of formula (I) according to claim 1, wherein D has the formula (II) or (III) and $R_{12}$ is selected from N-methylpyrrolylene, furanylene, thiophenylene, N-methylimidazolylene, oxazolylene, thiazolylene, indolylene, N-methylindolylene, benzofuranylene, benzothiophenylene, benzimidazolylene, N-methylbenzoimidazolylene, benzooxazolylene and benzothiazolylene.

13. A compound of formula (I) according to claim 1, wherein D has the formula (II) or (III), Z is absent and $R_{13}$ is $CO_2R$''.

14. A compound of formula (I) according to claim 1, wherein the compound of formula (I) is:

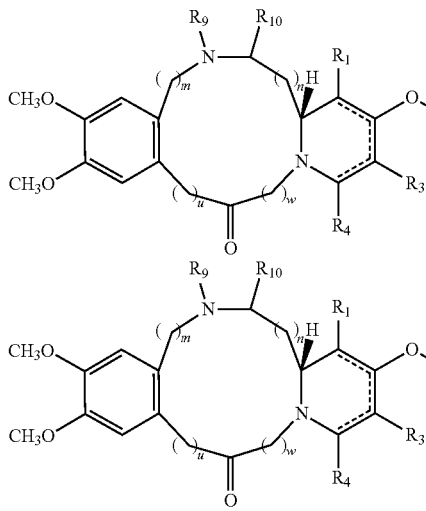

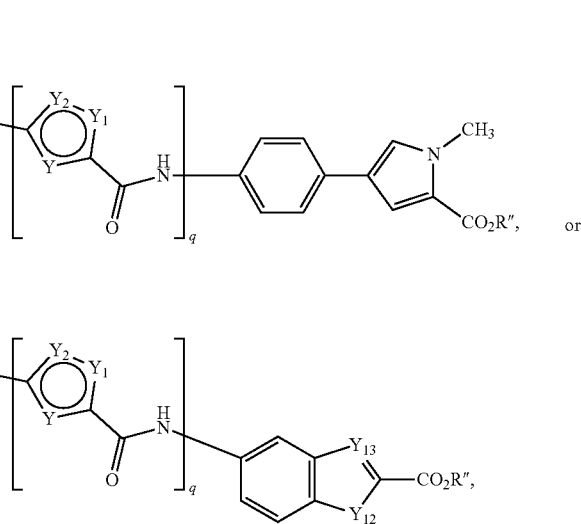

wherein q is selected from 1, 2, 3, 4, 5 or 6; L is an alkylene chain containing from 1 to 12 carbon atoms; Y, $Y_1$ and $Y_2$ are CH, N—$CH_3$ and CH or are N, N—$CH_3$ and CH; $Y_{12}$ is selected from O, S, NH and N—$CH_3$; $Y_{13}$ is selected from CH and N; and R" is selected from H and $C_{1-6}$ alkyl.

15. A compound of formula (I) according to claim 1, wherein the compound is a dimer with each monomer being the same and being of formula (I).

16. A compound of formula (I) according to claim 1, wherein the compound has the following structure:

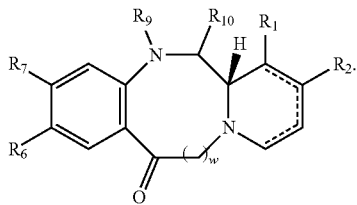

and salts or solvates thereof, wherein:
the dotted lines indicates the optional presence of a double bond between one or more of C1 and C2, C2 and C3, and C3 and C4;
$R_6$ is selected from H, $C_{1-12}$ alkyl, $C_{2-12}$ alkenyl, OH, O—$C_{1-12}$ alkyl, $OCH_2Ph$, $NH_2$, $NH(C_{1-12}$ alkyl), =O, =CH—$C_{1-12}$ alkyl, =$CH_2$, $CO_2H$, C(O)—O—$C_{1-12}$ alkyl;
and either:
  (i) $R_9$ and $R_{10}$ together form a double bond;
  (ii) $R_9$ is H and $R_{10}$ is OH; or
  (iii) $R_9$ is H and $R_{10}$ is O—$C_{1-6}$ alkyl;
wherein w may be 0 or 1; and
  (a) the compound is a dimer with each monomer being the same or different and being of formula (I) where one of $R_1$, $R_2$ and $R_7$ of the first monomer and one of $R'_1$, $R'_2$ and $R'_7$ of the second monomer form together a bridge having the formula —X-L-X'— linking the monomers and w=1;
  and the remaining of $R_1$ and $R_2$ of the first monomer and the remaining of $R'_1$, and $R'_2$ of the second monomer that do not form the bridge are independently selected from H, $C_{1-12}$ alkyl, $C_{2-12}$ alkenyl, OH, O—$C_{1-12}$ alkyl, $NH_2$, $NH(C_{1-12}$ alkyl), =O, =CH—$C_{1-12}$ alkyl, =$CH_2$, $CO_2H$ and C(O)—O—$C_{1-12}$ alkyl;
  and the remaining of $R_7$ of the first monomer and $R'_7$ of the second monomer that do not form the bridge are independently selected from H, $C_{1-12}$ alkyl, $C_{2-12}$ alkenyl, OH, O—$C_{1-12}$ alkyl, $OCH_2Ph$, $NH_2$, $NH(C_{1-12}$ alkyl), $CO_2H$ and C(O)—O—$C_{1-12}$ alkyl;
or
  (b) the compound is a dimer with each monomer being the same or different and being of formula (I) where one of RI and $R_2$ of the first monomer and one of $R'_1$ and $R'_2$ of the second monomer form together a bridge having the formula —X-L-X'— linking the monomers and w=0;
  and the remaining of $R_1$, and $R_2$ of the first monomer and the remaining of $R'_1$ and $R'_2$ of the second monomer that do not form the bridge are independently selected from H, $C_{1-12}$ alkyl, $C_{2-12}$ alkenyl, OH, O—$C_{1-12}$ alkyl, $NH_2$, $NH(C_{1-12}$ alkyl), =O, —CH—$C_{1-12}$ alkyl, =$CH_2$, $CO_2H$ and C(O)—O—$C_{1-12}$ alkyl;
  and that $R_7$ of the first monomer and $R'_7$ of the second monomer are independently selected from H, $C_{1-12}$ alkyl, $C_{2-12}$ alkenyl, OH, O—$C_{1-12}$ alkyl, $OCH_2Ph$, $NH_2$, $NH(C_{1-12}$ alkyl), $CO_2H$ and C(O)—O—$C_{1-12}$ alkyl;
or
  (c) one of $R_1$ and $R_2$ has the formula: —X-L-X'-D; or —$(CH_2)_f$—O—$R_{14}$;
  wherein $R_{14}$ is selected from H and $C_{1-12}$ alkyl;
  f is 0 or 1;
  and w is o or 1;
  and the remaining of $R_1$ and $R_2$ is selected from H, $C_{1-12}$ alkyl, $C_{2-12}$ alkenyl, OH, O—$C_{1-12}$ alkyl, $NH_2$, $NH(C_{1-12}$ alkyl), =O, =CH—$C_{1-12}$ alkyl, =$CH_2$, $CO_2H$ and C(O)—O—$C_{1-12}$ alkyl;
  and $R_7$ is selected from H, $C_{1-12}$ alkyl, $C_{2-12}$ alkenyl, OH, O—$C_{1-12}$ alkyl, $OCH_2Ph$, $NH_2$, $NH(C_{1-12}$ alkyl), $CO_2H$ and C(O)—O—$C_{1-12}$ alkyl;

or (d) $R_7$ has the formula:
—X-L-X'-D;
or
$(CH_2)_g$—O—$R_{15}$;
wherein $R_{15}$ is selected from H and $C_{1-12}$ alkyl;
g is 0 or 1;
and m+n+u+w=1;
and $R_1$ and $R_2$ are independently selected from H, $C_{1-12}$ alkyl, $C_{2-12}$ alkenyl, OH, O—$C_{1-12}$ alkyl, $NH_2$, $NH(C_{1-12}$ alkyl), =O, =CH—$C_{1-12}$ alkyl, =$CH_2$, $CO_2H$ and C(O)—O—$C_{1-12}$ alkyl;
wherein:
X is selected from O, =CH—, C(=O)NH and NHC(=O);
L is selected from a peptide chain having from 2 to 6 amino acids, an alkylene chain containing from 1 to 12 carbon atoms which may contain one or more carbon-carbon double or triple bonds, —$(OCH_2)_{1-12}$—, and —$OCH_2CH_2)_{1-6}$—;
X' is selected from O, =CH—, C(=O)NH and NHC(=O) or is absent; and
D is selected from formula (D1):

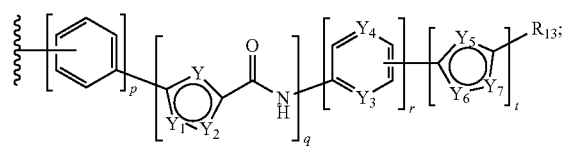

formula (D2):

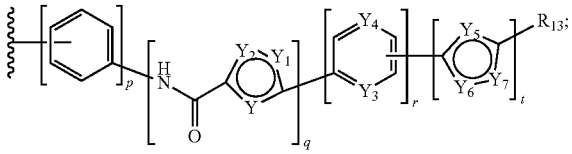

formula (D3):

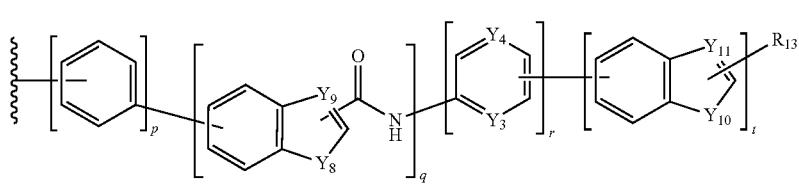

and formula (D4):

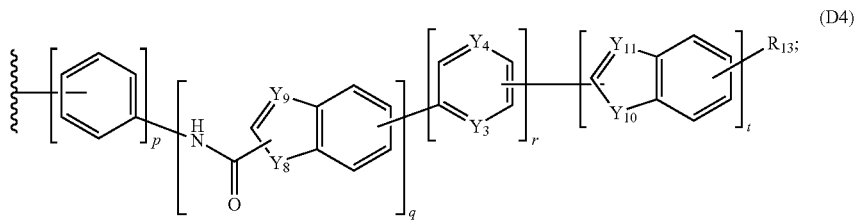

p is 0 or 1;
q is 1, 2, 3, 4, 5 or 6;
r is o or 1;
t is o or 1;
Y, $Y_1$ and $Y_2$ are selected from CH, CH and N—$CH_3$; CH, N—$CH_3$ and CH; N, CH and N—$CH_3$; N, N—$CH_3$ and CH; CH, S and CH; CH, CH and S; N, S and CH; N, CH and S; N, O and CH; N, CH and O; CH, CH and O; CH O and CH; COH, N—$CH_3$ and CH; and COH, CH and N—$CH_3$;
$Y_3$ is N or CH;
$Y_4$ is N or CH; wherein at least one of $Y_3$ and $Y_4$ is CH;
$Y_5$, $Y_6$ and $Y_7$ are selected from CH, CH and N—$CH_3$; CH, N—$CH_3$ and CH; N, CH and N—$CH_3$; N, N—$CH_3$ and CH; CH, S and CH; CH, CH and S; N, S and CH; N, CH and S; N, O and CH; N, CH and O; CH, CH and O; CH O and CH; COH, N—$CH_3$ and CH; and COH, CH and N—$CH_3$;
$Y_8$ is selected from O, S, NH and N—$CH_3$;
$Y_9$ is selected from CH and N;
$Y_{10}$ is selected from O, S, NH and N—$CH_3$;
$Y_{11}$ is selected from CH and N;
$R_{13}$ is H, Z—R", Z—$CO_2$R", Z—C(=O)—NH—$(CH_2)_{1-6}$—NR"R''', and Z—C(=O)—NH—$(CH_2)_{1-6}$—C(=NH)NR"R''';
Z is absent or is selected from benzofuranylene, benzothiophenylene, indolylene, N-methyl indolylene, N-methylbenzimidazolylene, benzoxazolylene and benzothiazolylene;
k is 0, 1, 2, 3 or 4; and
each R" and R''' is independently selected from H, and $C_{1-12}$ alkyl.

17. A compound of formula (I) according to claim 1, wherein the compound has the following structure:

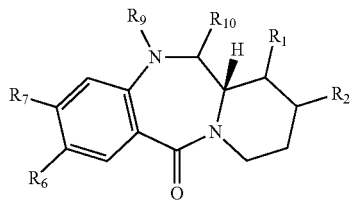

or is a dimer with the following structure:

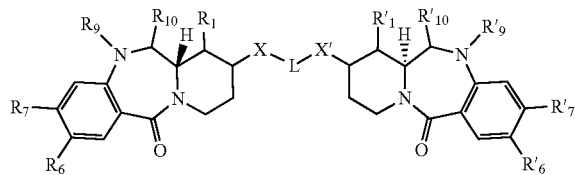

and salts or solvates thereof, wherein:

$R_1$ and $R'_1$ are independently selected from H, $C_{1-12}$ alkyl, $C_{2-12}$ alkenyl, OH, O—$C_{1-12}$ alkyl, $NH_2$, $NH(C_{1-12}$ alkyl), =O, =CH—$C_{1-12}$ alkyl, =$CH_2$, $CO_2H$ and C(O)—O—$C_{1-12}$ alkyl;

$R_6$, $R_7$, $R'_6$, and $R'_7$ are independently selected from H, $C_{1-12}$ alkyl, O—$C_{1-12}$ alkyl, $OCH_2Ph$;

and either:
(i) $R_9$ and $R_{10}$ together form a double bond, and $R'_9$ and $R'_{10}$ together form a double bond;
(ii) $R_9$ is H and $R_{10}$ is OH, and $R'_9$ is H and $R'_{10}$ is OH; or
(iii) $R_9$ is H and $R_{10}$ is $OR^A$ and $R^A$ is $C_{1-6}$ alkyl, and $R'_9$ is H and $R'_{10}$ is O—$C_{1-6}$ alkyl;

wherein:
$R_2$ has the formula:
—X-L-X'-D;
or is:
—$(CH_2)_f$—O—$R_{14}$;
$R_{14}$ is selected from H and $C_{1-12}$ alkyl;
f is 0 or 1;
X is selected from O, =CH—, C(=O)NH and NHC(=O);
L is selected from a peptide chain having from 2 to 5 amino acids; an alkylene chain containing from 1 to 11 carbon atoms which may contain one or more carbon-carbon double or triple bonds; —$(OCH_2)_{1-12}$— and —$(OCH_2CH_2)_{1-5}$—;
X' is selected O, =CH—, C(=O)NH and NHC(=O) or is absent;

D is:

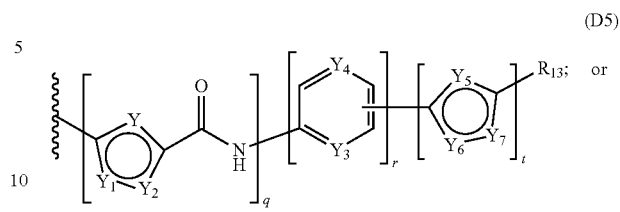

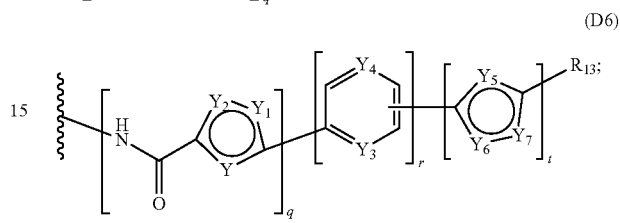

q is 1, 2, 3, 4, 5 or 6;
r is 0 or 1;
t is 0 or 1
Y, $Y_1$ and $Y_2$ are selected from CH, CH and N—$CH_3$; CH, N—$CH_3$ and CH; N, CH and N—$CH_3$; N, N—$CH_3$ and CH;
$Y_3$ is N or CH;
$Y_4$ is N or CH; wherein at least one of $Y_3$ and $Y_4$ is CH;
$Y_5$, $Y_6$ and $Y_7$ are selected from CH, CH and N—$CH_3$; CH, N—$CH_3$ and CH; N, CH and N—$CH_3$; N, N—$CH_3$ and CH;
$R_{13}$ is H, Z—H, Z—$C_{1-6}$ alkyl, Z—$CO_2H$ and Z—$CO_2C_{1-6}$ alkyl; and
Z is absent or is selected from benzofuranylene, benzothiophenylene, indolylene, N-methyl indolylene, N-methylbenzimidazolylene, benzoxazolylene and benzothiazolylene.

18. A pharmaceutical composition comprising a compound of claim 1 and a pharmaceutically acceptable carrier or diluent.

19. A method of treating breast cancer in a subject, the method comprising administering to the subject a therapeutically effective amount of a compound of claim 1.

* * * * *